(12) United States Patent
Beyer, Jr. et al.

(10) Patent No.: US 8,022,184 B2
(45) Date of Patent: *Sep. 20, 2011

(54) IFBM'S TO PROMOTE THE SPECIFIC ATTACHMENT OF TARGET ANALYTES TO THE SURFACE OF ORTHOPEDIC IMPLANTS

(76) Inventors: Wayne F. Beyer, Jr., Bahama, NC (US); Robin Hyde-DeRuyscher, Chapel Hill, NC (US); Paul T. Hamilton, Cary, NC (US); Ray Edward Benson, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/871,231

(22) Filed: Aug. 30, 2010

(65) Prior Publication Data

US 2010/0317829 A1 Dec. 16, 2010

Related U.S. Application Data

(62) Division of application No. 12/488,183, filed on Jun. 19, 2009, now Pat. No. 7,812,119, which is a division of application No. 11/152,974, filed on Jun. 15, 2005, now Pat. No. 7,572,766.

(60) Provisional application No. 60/580,019, filed on Jun. 16, 2004, provisional application No. 60/651,338, filed on Feb. 9, 2005, provisional application No. 60/651,747, filed on Feb. 10, 2005.

(51) Int. Cl.
*C07K 14/00* (2006.01)
(52) U.S. Cl. ...................................... 530/351
(58) Field of Classification Search .................. 530/351
See application file for complete search history.

(56) References Cited

U.S. PATENT DOCUMENTS

2002/0151708 A1 10/2002 Guerriero

OTHER PUBLICATIONS

Buslepp, et al. T Cell Activity Correlates with Oligomeric Peptide-Major Histocompatibility Complex Binding on T Cell Surface, JBC, vol. 276, No. 50, pp. 47320-47328, 2001.
Higa et al. Sialogogic activity in rat of peptides analogous to Tyr-sub P in which subst have been made in the N-term amino acids, Archives of Oral Biology, 2001, 46: 313-321.
Kirsch et al. Isolation of recombinant BMP receptor IA ectodomain and its 2:1 complex with BMP-2, FEBS Letters, 2000, 468: 215-219.
Loftus et al. Differential Contact of Disparate Class I/Peptide Complexes as a Basis for Epitopte Cross-Recognition by T Cell Receptor, J. Immunology, 1997, 158: 3651-3658.
Feb. 1, 2011, Second Exam Report for Canadian Patent Appn No. 2569864.
Jan. 12, 2011, European Search Report for EP Appn No. 10177135.0.
Jun. 23, 2010, European Search Report for EP Appn No. 09173344.

*Primary Examiner* — Karen Carlson
(74) *Attorney, Agent, or Firm* — Laura L. Kiefer

(57) ABSTRACT

The present invention provides an improved coating for surfaces of medical implants. The coating comprises at least one interfacial biomaterial (IFBM) which is comprised of at least one binding module that binds to the surface of an implant or implant-related material ("implant module") and at least one binding module that selectively binds to a target analyte or that is designed to have a desired effect ("analyte module"). The modules are connected by a linker. In some embodiments, the IFBM coating acts to promote the recognition and attachment of target analytes to surface of the device. The IFBM coating improves the performance of implanted medical devices, for example, by promoting osteointegration of the implant.

4 Claims, 13 Drawing Sheets

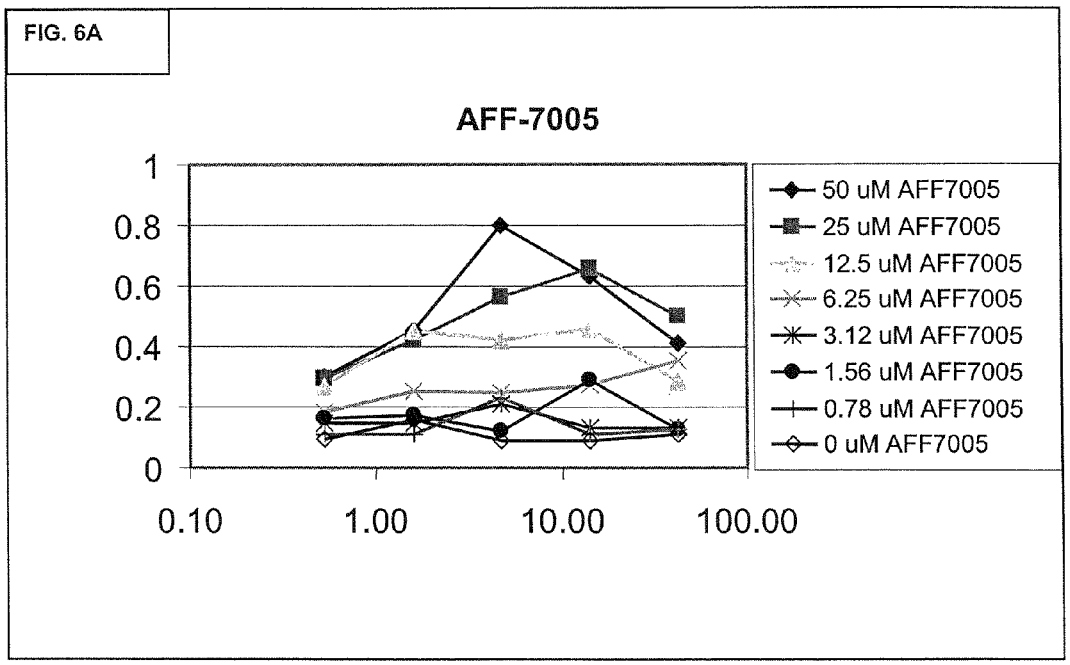
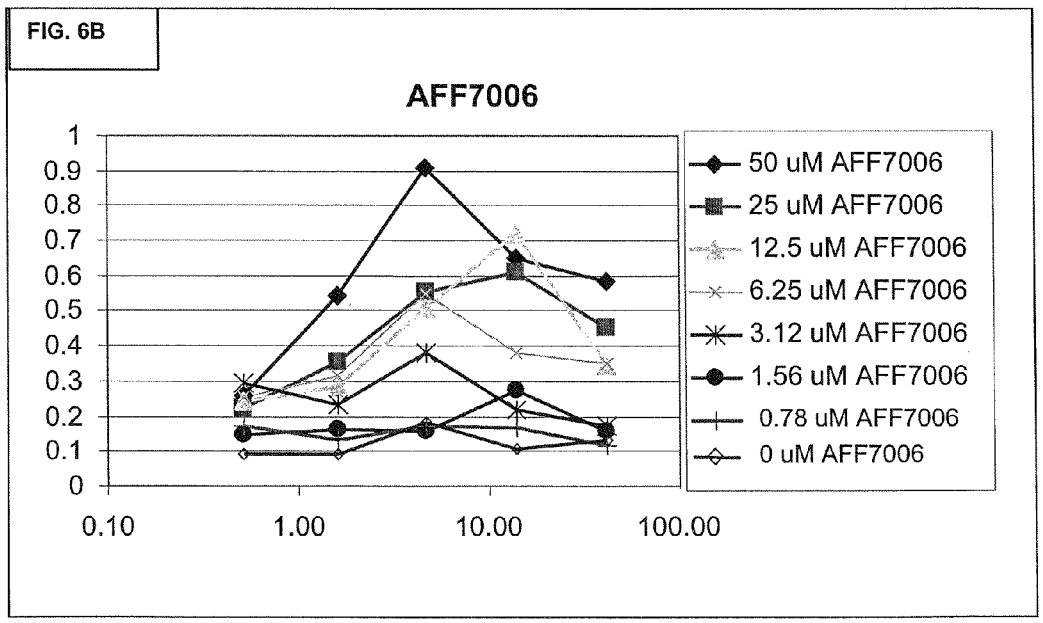

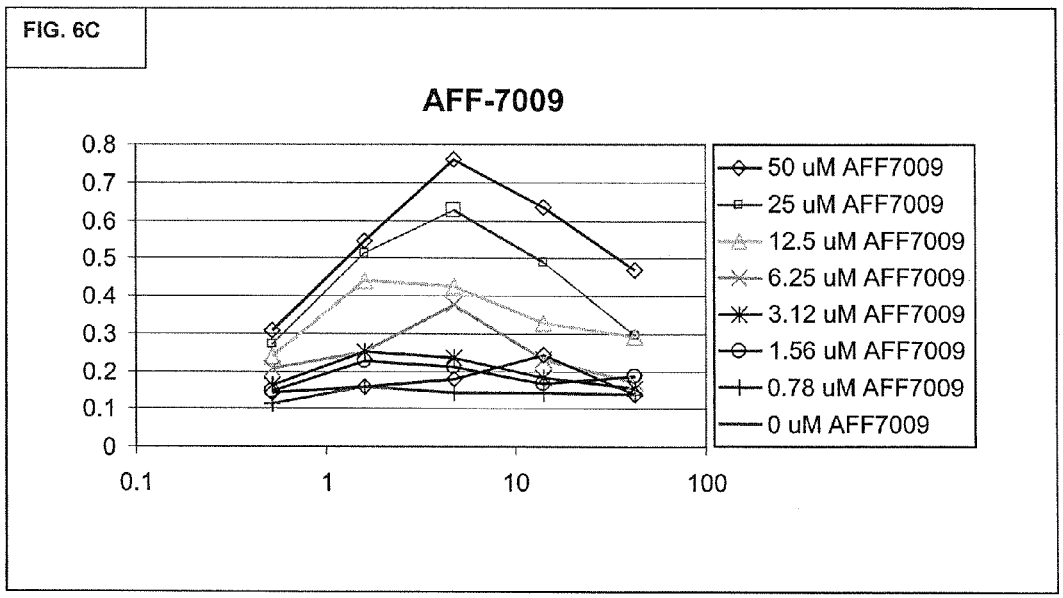
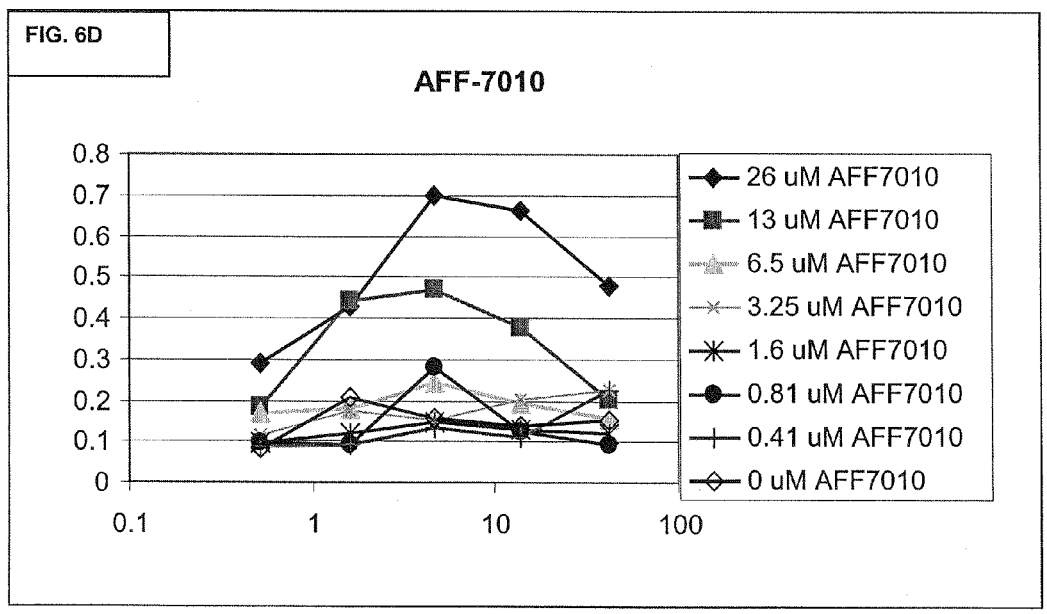

Identification of Motif 1

```
G2  G4  G7  G11 G11 G15 A14 W31 E17 A13 F36 S14 S16 L34 S13 G16 S6  R7  V12
A2  L2  V6  E5  S8  S5  F5  S7  S12 W3  A7  A11 E11 M6  A5  G5  A3
D2  V2  E5  V5  A5  A3  Y2  D6  V7  I1  E5  G8  T4  A7  E4  V5  A3
P2  D1  S4  A4  V2  V2  Y2  G2  G4  W2  T2  E1  T2  R4  S5  V4  E3  S2
V1  E1  A3  S3  W2  E3  V1  G1  V2  W2  E1  R4  A3  W2  T4  A2  T2
W1  T1  T2  D2  Q2  V3  T2  R2  R2  E1  K3  L1  E1  V3  H1  D2  S2  R2
K1  R1  D1  P2  D1  D1  G1  E1  Q2  F1  K1  L2  L1  V3  G1  R1  G1  N2  D1
        F1  M1  E1  H1  L1  A1          D1      V1      D1      P1  H1  D1  E1
        L1  R1  M1  Y1  T1  R1          T1              Y1          Y1  W1  L1
        N1  Q1  T1  P1  R1              N1                              Q1  M1
        Q1      P1      N1                                              Q1
        P1
```

Motif 1a: W-X-X-F-X-X-L

Consensus: G-G-G-A-W-E-A-F-S-S-L-S-G-S-R-V

FIG. 7

```
-Xho I-                                                              -Xba I-
  S   S   G   A   W   E   S   F   S   S   L   S   G   S   S
TCG AGT GGT GCT TGG GAG TCT TTT TCG TCA CTG AGT GGA T
    CA CCA CGA ACC CTC AGA AAA AGC AGT GAC TCA CCT AGA TC
```

FIG. 8

Identification of Motif 2

| G7 | G5 | A3 | L9 | G6 | F14 | P18 | L17 | K10 | G18 | E4 | V6 | V8 | E5 | G5 | W4 | A4 |
|----|----|----|----|----|-----|-----|-----|-----|-----|----|----|----|----|----|----|----|
| E4 | D2 | S3 | V8 | R2 | L3  | I1  | R6  |     | Q3  | P4 | I2 | S3 | A3 | A2 | D2 |    |
| S2 | E2 | G2 | G1 | S2 | W1  |     | S1  |     | D2  | T4 | M2 | D2 | V3 | K2 | E2 |    |
| A1 | K1 | D2 |    | A1 |     |     | T1  |     | I2  | L3 | Q2 | G2 | D2 | P2 | P2 |    |
| F1 | L1 | P2 |    | E1 |     |     |     |     | T2  | W1 | A1 | K1 | Q1 | V2 | V2 |    |
| M1 | N1 | F1 |    | H1 |     |     |     |     |     | A1 | L1 | P1 | T1 | G1 | H1 |    |
| P1 | P1 | R1 |    | N1 |     |     |     |     |     | R1 | W1 | T1 | W1 | M1 | K1 |    |
| V1 | R1 | T1 |    | P1 |     |     |     |     |     | S1 | Y1 | W1 |    | T1 | F1 |    |
|    | S1 | V1 |    | V1 |     |     |     |     |     | V1 |    |    |    |    | G1 |    |
|    | V1 | W1 |    | W1 |     |     |     |     |     | W1 |    |    |    |    |    |    |
|    | W1 | Y1 |    | Y1 |     |     |     |     |     |    |    |    |    |    |    |    |
|    | Y1 |    |    |    |     |     |     |     |     |    |    |    |    |    |    |    |

Motif: (L/V)-X-F-P-L-(K/R)-G

Consensus: G-G-A-L-G-F-P-L-K-G-E-V-V-E-G-W-A

FIG. 10

IFBM'S TO PROMOTE THE SPECIFIC ATTACHMENT OF TARGET ANALYTES TO THE SURFACE OF ORTHOPEDIC IMPLANTS

CROSS-REFERENCE TO RELATED APPLICATIONS

This application is a divisional application of U.S. Non-provisional application Ser. No. 12/488,183, filed on Jun. 19, 2009 now U.S. Pat. No. 7,812,119, which is a divisional application of U.S. Non-provisional application Ser. No. 11/152,974, filed on Jun. 15, 2005, now U.S. Pat. No. 7,572, 766, which claims priority to U.S. Provisional Application No. 60/580,019, filed Jun. 16, 2004; U.S. Provisional Application No. 60/651,338, filed Feb. 9, 2005; and U.S. Provisional Application No. 60/651,747, filed Feb. 10, 2005; each of which is hereby incorporated in its entirety by reference herein.

FIELD OF THE INVENTION

The present invention provides materials and methods for coating surfaces of medical devices with interfacial biomaterials that promote the specific recognition and attachment of the target analyte to the surface of the device.

BACKGROUND OF THE INVENTION

Orthopedic implants are used for a variety of joint replacements and to promote bone repair in humans and animals. According to medical industry analysts, there are now over 800,000 hip and knee joint replacements performed in human patients each year in the U.S. In addition, hundreds of thousands of human patients undergo surgical procedures in which orthopedic implants are used, for example, to treat various types of bone fractures or to relieve severe back pain.

With all of these procedures, there is a need for controlled, directed, rapid healing. Individuals undergoing joint replacement often experience uncomplicated healing and restoration of function. Unfortunately, there is a high rate of complications, including "late failures." The revision surgery rate for human total joint replacement varies between 10 to 20% (Malchau et al. (2002) "Prognosis of total hip replacement: Update of results and risk-ratio analysis for revision and re-revision from the Swedish National Hip Arthroplasty Registry, 1979-2000," scientific exhibition at the 69th Annual Meeting of the American Academy of Orthopaedic Surgeons, Dallas, Tex., Feb. 13-17, 2002; Fitzpatrick et al. (1998) Health Technol. Assess. 2:1-64; Mahomed et al. (2003) J. Bone Joint Surg. Am. 85-A:27-32)). The majority of these revision surgeries are made necessary by failure at the implant-bone interface.

Orthopedic implants are made of materials which are relatively inert ("alloplastic" materials), typically metallic, ceramic, or plastic materials. Previous approaches to improve the outcomes of orthopedic implant surgeries have mainly focused on physical changes to the implant surface that result in increased bone formation. These approaches include using implants with porous metallic surfaces to promote bone ingrowth and spraying implants with hydroxyapatite plasma. Approaches using dental implants have also included the use of topographically-enhanced titanium surfaces in which surface roughness is imparted by a method such as grit blasting, acid etching, or oxidation. While these techniques have improved the outcomes of orthopedic implant surgeries, there is still considerable room for further improvement.

Tissue response to an alloplastic material is known to be influenced by cell adhesion to the material's surface, and much research has been directed to improving cell adhesion to alloplastic materials. Cell adhesion between cells in vivo is known to be controlled primarily by the binding of short, exposed protein domains in the extracellular matrix to cell surface receptors (LeBaron & Athanasiou (2000) Tissue Eng. 6: 85-103; Yamada (1997) Matrix Biol. 16: 137-141). Notably, a class of receptors known as integrins has been implicated in cell adhesion to implant surfaces. Integrins and their target ligands have been shown to stimulate osteoblast adhesion and proliferation as well as bone formation (see, e.g., Kantlehner et al. (2000) Chem Bio Chem 1: 107-114; Sarmento et al. (2004) J. Biomed. Mater. Res. 69A: 351-358; Hayashibara et al. (2004) J. Bone Mineral Res. 19: 455-462. Integrins may be useful in targeting cell adhesion to implants and in this manner may improve integration of implants into adjacent bone.

Other research has shown that the local expression of growth factors and cytokines can enhance tissue reactions at alloplastic implant surfaces. For example, Cole et. al. ((1997) Clin. Orthop. 345: 219-228) have shown that growth factors can promote the integration of an implant into adjacent bone ("osteointegration") as well as increase the rate of bone formation next to the implant surface. See also U.S. Pat. No. 5,344,654. Growth factors that stimulate new bone production ("osteoinductive proteins") include, but are not limited to, platelet-derived growth factor (PDGF), insulin-like growth factors 1 and 2 (IGF-1 and IGF-2), vascular endothelial growth factor (VEGF), fibroblast growth factor (FGF), transforming growth factor (TGF-β), bone morphogenic proteins (BMP), and associated family members.

The most effective osteoinductive proteins are the bone morphogenetic proteins (BMPs). The BMPs are members of the TGF-β superfamily that share a set of conserved cysteine residues and a high level of sequence identity overall. Over 15 different BMPs have been identified, and most BMPs stimulate the cascade of events that lead to new bone formation (see U.S. Pat. Nos. 5,013,649; 5,635,373; 5,652,118; and 5,714, 589; also reviewed by Reddi and Cunningham (1993) J. Bone Miner. Res. 8 Supp. 2: S499-S502; Issack and DiCesare (2003) Am. J. Orthop. 32: 429-436; and Sykaras & Opperman (2003) J. Oral Sci. 45: 57-73). This cascade of events that leads to new bone formation includes the migration of mesenchymal stem cells, the deposition of osteoconductive matrix, the proliferation of osteoprogenitor cells, and the differentiation of progenitor cells into bone-producing cells. Much research has been directed to the use of BMPs on or near implants in order to promote osteointegration of the implants (see, e.g.: Friedlander et al. (2001) J. Bone Joint Surg. Am. 83-A Suppl. 1 (Pt. 2): S151-58; Einhorn (2003) J. Bone Joint Surg. Am. 85-A Suppl. 3: 82-88; Burkus et al. (2002) J. Spinal Disord. Tech. 15(5): 337-49). However, one of the critical issues that remains unresolved is the method of grafting or immobilizing an active BMP or other active biomolecule onto the surface of an implant.

It has been shown that the presentation of BMPs is critical for producing desired bone formation next to an implant device. Approaches to improving implants have been modeled in view of the natural process of bone formation. In human bone, collagen serves both as a scaffold for bone formation and as a natural carrier for BMPs. Demineralized bone has been used successfully as a bone graft material; the main components of demineralized bone are collagen and BMPs (see U.S. Pat. No. 5,236,456). Many matrix systems have been developed that are designed to encourage bone formation by steadily releasing growth factors and other bioactive molecules as the matrix degrades. The efficiency of BMP release from polymer matrixes depends on matrix characteristics such as the affinity of BMP for the matrix, resorbtion rate, density, and pore size. Materials used in such matrix systems include organic polymers which readily hydrolyze in the body into inert monomers. Such organic polymers include polylactides, polyglycolides, polyanhydrides, and poly-orthoesters (see U.S. Pat. Nos. 4,563,489; 5,629,009; and 4,526,909). Other materials described as being useful in BMP-containing matrices include polylactic and polyglycolic acid copolymers, alginate, poly(ethylene glycol), poly-oxyethylene oxide, carboxyvinyl polymer, and poly (vinyl alcohol) (see U.S. Pat. No. 5,597,897). Natural matrix proteins have also been used to deliver BMPs to bone areas; these natural proteins include collagen, glycosaminoglycans, and hyaluronic acid, which are enzymatically digested in the body (see U.S. Pat. Nos. 4,394,320; 4,472,840; 5,366,509; 5,606,019; 5,645,591; and 5,683,459).

Even with the use of a polymer matrix to retain BMP at the site of repair, it has been found that supraphysiological levels of BMP are required in order to promote healing due to the rapid diffusion of growth factors out of the matrix. For example, with a collagen sponge delivery system, only 50% of the BMP added to the sponge is retained after two days (Geiger et al. (2003) Adv. Drug Del. Rev. 55: 1613-1629). The high initial dose of BMPs required to maintain physiological levels of BMP for the necessary period of time makes BMP treatment more expensive and may lead to detrimental side effects such as ectopic bone formation or allergic reactions, or the formation of neutralizing antibodies.

Similar problems exist with other implants such as tendon and ligament replacements, skin replacements, vascular prostheses, heart pacemakers, artificial heart valves, breast implants, penile implants, stents, catheters, shunts, nerve growth guides, intraocular lenses, wound dressings, and tissue sealants. As with orthopedic implants, surgery involving these implants often gives rise to similar problems with the slow healing of wounds and, where desirable, improper integration of the implant into surrounding tissue.

Thus, there remains a need for the development of cost-effective methods for grafting active biomolecules to the surface of materials used as implants or in conjunction with implants in order to promote post-surgical healing and, where desirable, integration of the implant into surrounding tissues, such as, for example, adjacent bone.

SUMMARY OF THE INVENTION

The present invention provides an improved coating for surfaces of medical implants. The coating comprises at least one interfacial biomaterial (IFBM) which is comprised of at least one binding module that binds to the surface of an implant or implant-related material ("implant module") and at least one binding module that binds to a target analyte or that is designed to have a desired effect ("analyte module"). The modules are connected by a linker. In some embodiments, the IFBM coating acts to promote the recognition and attachment of target analytes to surface of the device. The IFBM coating improves the performance of implanted medical devices by promoting osteointegration of the implant, accelerating healing, and/or reducing inflammation at the site of the implant.

BRIEF DESCRIPTION OF THE DRAWINGS

FIGS. 6A, 6B, 6C, and 6D show the results of an experiment described in Example 4 which demonstrates that the binding of BMP to collagen via an IFBM is dependent on both the amount of BMP put into the sponge and also on the amount of IFBM present. Absorbance (vertical axis) is shown as a function of BMP concentration (horizontal axis).

FIG. 7 shows the results of an analysis of all the peptide sequences from Tables 3 and 4 that bind BMP-2 and contain Motif 1 (see Example 3). The figure shows for each analyzed position the number of times each amino acid was found in that position in the peptide sequences analyzed; for example, "G2" in position 1 means that Glycine was found two times in that position.

FIG. 8 shows the oligonucleotide cassette which was designed to express a peptide (SEQ ID NO: 74) containing the core binding Motif 1a in the context of a peptide sequence which also contained consensus residues identified for other positions in the sequence (see Example 3). The nucleotide sequences shown in the figure are also set forth in SEQ ID NO: 75 and SEQ ID NO: 76.

FIG. 10 shows the results of an analysis of all the peptide sequences from Tables 3 and 5 that bind BMP-2 and contain Motif 2. The figure shows for each analyzed position the number of times each amino acid was found in that position in the peptide sequences analyzed; for example, "G7" in position 1 means that Glycine was found seven times in that position. Also shown are a consensus sequence derived from an alignment of the peptides from Tables 3 and 5 that contain Motif 2 (SEQ ID NO: 93). This sequence represents the predominant amino acid found at each position after all the peptides are aligned. Among the sequences examined, the most conserved amino acids form a core binding motif designated "Motif 2a" (SEQ ID NO: 94).

DETAILED DESCRIPTION OF THE INVENTION

Figure 1:
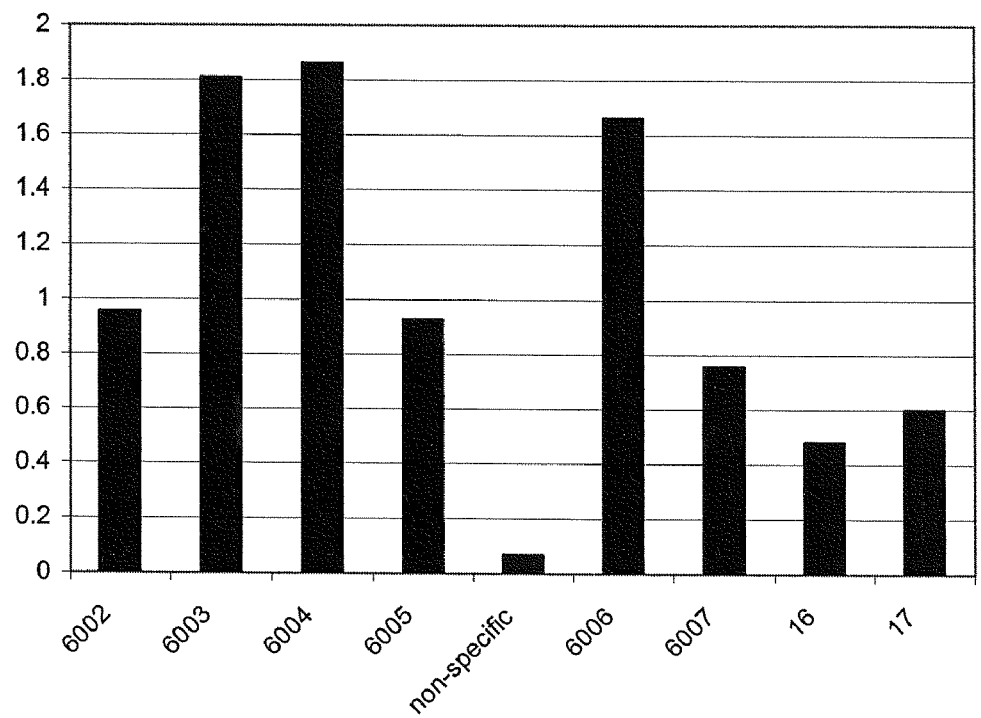
FIG. 1 shows a comparison of the binding of phage that display representative titanium-binding peptides to titanium beads (see Example 1). Signal of assay for binding to titanium beads (vertical axis) is shown for various phage (horizontal axis).

The present invention provides an improved coating for surfaces of medical devices to promote the attachment of peptides, proteins, drugs, or cells to the device. The coating is an interfacial biomaterial (IFBM) that comprises multiple binding modules that are linked. The IFBM comprises at least one binding module which binds to the surface of the implant ("implant module") and at least one binding module that binds to a target analyte or has a desired effect ("analyte module"). Exemplary binding modules comprise the peptide sequences provided, for example, in the sequence listing (SEQ ID NOs: 1-74 and 77-558). The modules are connected by a linker. In some embodiments, the binding of the binding module of an IFBM to the surface of an implant is non-covalent. Similarly, in some embodiments, the binding of an analyte module to a target analyte is non-covalent. According to one embodiment, the implant module and the analyte module comprise two separate peptide molecules such that the implant module binds to an implant material and the analyte module binds specifically to a growth factor or cell. In some embodiments, the implant module and the analyte module are linked by a central macromolecule. These binding modules typically bind non-covalently to the implant material or target analyte, respectively. In embodiments where the analyte module does not bind to a target analyte but rather has a desired effect, the analyte module may, for example, simulate the action of a growth factor by acting to recruit cells to the location of the implant. The IFBM selection method and structure are described in U.S. patent application Ser. No. 10/300,694, filed Nov. 20, 2002 and published on Oct. 2, 2003 as publication number 20030185870, which is herein incorporated by reference.

By "binds specifically" or "specific binding" is intended that the implant module or analyte module binds to a selected implant material or to a selected analyte. In some embodiments, a module that binds specifically to a particular implant material or analyte binds to that material or analyte at least 10%, 20%, 30%, 40%, 50%, 60%, 70%, 80%, 90%, 100%, 200%, 300%, 400%, 500%, or a higher percentage more than the module binds to an appropriate control such as, for example, a different material that is used in implants, a material that is not used in implants, or a protein typically used for such purposes such as bovine serum albumin. By "analyte" is intended any substance or moiety that improves osteointegration of an implant or promotes or accelerates healing of the surrounding tissues following implant surgery. Suitable analytes which are binding targets for analyte modules include, but are not limited to, growth factors such as bone morphogenic proteins (BMPs, such as, for example, BMP-7 and BMP-2), vascular endothelial growth factor (VEGF), platelet-derived growth factor (PDGF), transforming growth factor-β (TGF-β), insulin growth factor-1 (IGF-1), insulin growth factor-2 (IGF-2), fibroblast growth factor (FGF), nerve growth factor (NGF), and placental growth factor. Suitable analytes also include hormones, enzymes, cytokines, and other bioactive substances or moieties which are useful in obtaining the goals of the invention; that is, to promote osteointegration of an implant and/or to improve healing of surrounding tissues following implant surgery. Suitable analytes also include cells, for example, osteoblasts, chondrocytes, stem cells, progenitor cells, platelets, and other cells which perform roles in osteointegration and healing. In some embodiments, analyte modules can comprise peptide sequences that bind cells or have bioactivity through binding to cells or receptors such as, for example, the peptide sequences RGD, YIGSR, and IKVAV, which are known in the art to have particular biological activities. See, e.g., Hersel et al. (2003) *Biomaterials* 24: 4385-4415; Grant et al. (1990) *Ann. N.Y. Acad. Sci.* 588: 61-72; Hosokawa et al. (1999) *Dev. Growth Differ.* 41: 207-216. In some embodiments, analyte modules comprise peptide sequences which bind to and/or mimic the effect of BMP-2, such as the exemplary sequences set forth in SEQ ID NOs: 11-28, 44-74, or 77-94. An analyte module that binds to cells can comprise a peptide that comprises a general cell attachment sequence that binds to many different cell types, or it can comprise a peptide that binds to a specific cell type such as an osteoblast, a chondrocyte, an osteoprogenitor cell, or a stem cell.

The term "implant" generally refers to a structure that is introduced into a human or animal body to restore a function of a damaged tissue or to provide a new function. An implant device can be created using any biocompatible material to which binding agents can specifically bind as disclosed herein. Representative implants include but are not limited to: hip endoprostheses, artificial joints, jaw or facial implants, tendon and ligament replacements, skin replacements, bone replacements and artificial bone screws, bone graft devices, vascular prostheses, heart pacemakers, artificial heart valves, breast implants, penile implants, stents, catheters, shunts, nerve growth guides, intraocular lenses, wound dressings, and tissue sealants. Implants are made of a variety of materials that are known in the art and include but are not limited to: a polymer or a mixture of polymers including, for example, polylactic acid, polyglycolic acid, polylactic acid-polyglycolic acid copolymers, polyanhidrides, polyorthoesters, polystyrene, polycarbonate, nylon, PVC, collagen (including, for example, processed collagen such as cross-linked collagen), glycosaminoglycans, hyaluronic acid, alginate, silk, fibrin, cellulose, and rubber; plastics such as polyethylene (including, for example, high-density polyethylene (HDPE)), PEEK (polyetheretherketone), and polytetrafluoroethylene; metals such as titanium, titanium alloy, stainless steel, and cobalt chromium alloy; metal oxides; non-metal oxides; silicone; bioactive glass; ceramic material such as, for example, aluminum oxide, zirconium oxide, and calcium phosphate; other suitable materials such as demineralized bone matrix; and combinations thereof. The term "polymer" as used herein refers to any of numerous natural and synthetic compounds of usually high molecular weight consisting of up to millions of repeated linked units, each a relatively simple molecule. The term "implant" as used herein includes implant-related materials that are associated with the implant and are also introduced into a human or animal body in conjunction with the implant.

In one embodiment of the invention, an IFBM creates a binding interface that mediates the attachment of growth factors to the surface of an implant. In some embodiments, implants prepared according to the methods of the invention will have growth factors specifically attached to the surface of the implant; the rate of diffusion of the growth factor away from the site of the implant can vary depending on the affinity of the analyte module for the growth factor in question and thus implants can be prepared with varying rates of diffusion of growth factors. In embodiments involving the attachment of growth factors to the surface of an implant, the growth factor will have a positive effect such as, for example, accelerating the healing process, reducing the amount of growth factor required for healing, and minimizing the side effects caused by using supraphysiological doses of the growth factor. Growth factors of particular interest either as analyte modules or as factors that bind to analyte modules include, for example, BMP-2, BMP-7, PDGF, FGF, and TGFβ.

Thus, the present invention provides methods for preparing an implant to be surgically placed into a patient wherein the device is coated with a layer comprising at least one IFBM. In some embodiments, the method comprises the steps of: (a) applying an IFBM coating to the implant, wherein the IFBM comprises an implant module that specifically binds to the implant and an analyte module that specifically binds a growth factor; (b) applying the growth factor to the surface of the implant by dipping, spraying, or brushing a solution containing the growth factor onto the implant; (c) placing the implant into a subject using appropriate surgical techniques which will be known to those of skill in the art.

Alternatively, a method for coating an implant so that the implanted device promotes growth factor attachment comprises the steps of: (a) applying an IFBM coating to the implant, wherein the IFBM comprises an implant module that specifically binds the implant and an analyte module that specifically binds growth factor at an implant site; and (b) placing the implant in a subject at the implant site; whereby growth factor produced in the host binds to the implant via the IFBM. The enhanced presence of growth factor at the implant site enhances healing of adjacent tissue and integration of the implant into the adjacent tissue.

In one embodiment of the invention, an IFBM mediates cell attachment to the surface of an implant. By enhancing cell adhesion and tissue integration, the IFBMs of the invention can accelerate healing and improve the function of the implanted device. Thus, in accordance with the present invention, a method for preparing an implant to be surgically placed into a patient can comprise: (a) applying an IFBM coating to the implant, wherein the IFBM comprises at least one implant module that specifically binds the implant and at least one analyte module that specifically binds to at least one type of cell; and (b) placing the implant in a subject at the implant site, whereby cells bind to the IFBM coating on the implant.

In some embodiments, a method for preparing an implant comprises: (a) applying an IFBM coating to the implant, wherein the IFBM comprises at least one implant module that specifically binds the implant and at least one analyte module that specifically binds at least one type of cell; and (b) applying cells to the surface of the implant, for example, by dipping the implant into a solution containing the cells or brushing a solution containing the cells onto the implant. The implant may then be placed into a subject (i.e., a human patient or an animal patient). By "patient" as used herein is intended either a human or an animal patient.

In another embodiment of the invention, an implant is coated with more than one type of IFBM in order to provide a coating with multiple functionalities. For example, an implant coating can comprise a first IFBM having an analyte module that binds a cell and a second IFBM having an analyte module that binds a growth factor. A coating comprising these IFBMs would bind both cells and growth factor to the surface of the implant. In some embodiments, these IFBMs would be intermingled in the coating so that the bound growth factor is in close proximity to the bound cells. In one embodiment, a coating comprises an IFBM that binds to mesenchymal stem cells and an IFBM that binds to the growth factor BMP-2; the BMP-2 would trigger the differentiation of the stem cells into osteoblasts. In other embodiments, an implant coating can comprise a mixture of at least two different IFBMs which differ in either or both their implant module and their analyte module. In another embodiment, a coating comprises a multifunctional IFBM which has two analyte modules, one of which binds to a cell and one of which binds to a growth factor.

Binding modules (i.e., implant modules and/or analyte modules) may be peptides, antibodies or antibody fragments, polynucleotides, oligonucleotides, complexes comprising any of these, or various molecules and/or compounds. Binding modules which are peptides may be identified as described in U.S. patent application Ser. No. 10/300,694, filed Nov. 20, 2002 and published on Oct. 2, 2003 as publication number 20030185870. In some embodiments, binding modules may be identified by screening phage display libraries for binding to materials including biocompatible materials (i.e., "biomaterials") such as titanium, stainless steel, cobalt-chrome alloy, polyurethane, polyethylene or silicone.

In some embodiments of the invention, the analyte module is a bioactive peptide or binds to a bioactive peptide. These bioactive peptides may be fragments of native proteins that retain the biological effect of the native protein, as is well-known in the art. For example, TP508 is a synthetic peptide derived from thrombin which represents amino acids 183-200 of human thrombin and has been shown to accelerate fracture healing (see, e.g., Wang et al. (2002) *Trans ORS* 27: 234). TP508 function is believed to be mediated by an RGD sequence within the peptide that binds to integrins present on the cell surface (see, e.g., Tsopanoglou et al. (2004) *Thromb Haemost.* 92(4):846-57.) Similarly, P-15 is a 15 amino acid peptide derived from Type I collagen that represents the cell-binding domain of collagen (see, e.g., Yang et al. (2004) *Tissue Eng.* 10(7-8): 1148-59). P-15 has been shown to enhance new bone formation (see, e.g., Scarano et al. (2003). *Implant Dent.* 12(4): 318-24.). Bioactive peptides can also be fragments of growth factors. For example, Saito et al. (*J Biomed Mater Res A*. 2005 72A(1): 77-82) have shown that a synthetic peptide representing amino acids 73-92 of BMP-2 retains BMP-2 biological activities including binding to a BMP-2 receptor, activating gene expression and inducing ectopic bone formation.

Any implant module may be combined with any analyte module to create an IFBM of the invention so long as the desired activity is provided; that is, so long as the IFBM specifically binds to a suitable implant and has a suitable effect conferred by the analyte module, i.e., the ability to bind to BMP-2. One of skill in the art will appreciate that a variety of types and numbers of implant modules may be combined with a variety of types and numbers of analyte modules to create an IFBM of the invention. Thus, for example, one or more implant modules may be linked with one or more analyte modules to create an IFBM. One of skill will be able to select suitable implant module(s) and analyte module(s) depending on the material of which an implant is made and the desired activity to be conferred by the analyte module(s).

The term "antibody" as used herein includes single chain antibodies. Thus, an antibody useful as a binding module may be a single chain variable fragment antibody (scFv). A single chain antibody is an antibody comprising a variable heavy and a variable light chain that are joined together, either directly or via a peptide linker, to form a continuous polypeptide. The term "single chain antibody" as used herein encompasses an immunoglobulin protein or a functional portion thereof, including but not limited to a monoclonal antibody, a chimeric antibody, a hybrid antibody, a mutagenized antibody, a humanized antibody, and antibody fragments that comprise an antigen binding site (e.g., $F_{ab}$ and $F_v$ antibody fragments).

Phage display technology is well-known in the art. Using phage display, a library of diverse peptides can be presented to a target substrate, and peptides that specifically bind to the substrate can be selected for use as binding modules. Multiple serial rounds of selection, called "panning," may be used. As is known in the art, any one of a variety of libraries and panning methods can be employed to identify a binding module that is useful in the methods of the invention. For example, libraries of antibodies or antibody fragments may be used to identify antibodies or fragments that bind to particular cell populations or to viruses (see, e.g., U.S. Pat. Nos. 6,174,708; 6,057,098; 5,922,254; 5,840,479; 5,780,225; 5,702,892; and 5,667,988). Panning methods can include, for example, solution phase screening, solid phase screening, or cell-based screening. Once a candidate binding module is identified, directed or random mutagenesis of the sequence may be used to optimize the binding properties of the binding module. The terms "bacteriophage" and "phage" are synonymous and are used herein interchangeably.

A library can comprise a random collection of molecules. Alternatively, a library can comprise a collection of molecules having a bias for a particular sequence, structure, or conformation. See, e.g., U.S. Pat. Nos. 5,264,563 and 5,824,483. Methods for preparing libraries containing diverse populations of various types of molecules are known in the art, and numerous libraries are also commercially available. Methods for preparing phage libraries can be found, for example, in Kay et al. (1996) *Phage Display of Peptides and Proteins* (San Diego, Academic Press); Barbas (2001) *Phage Display: A Laboratory Manual* (Cold Spring Harbor Laboratory Press, Cold Spring Harbor, N.Y.)

A binding module (i.e., implant module or analyte module) that is a peptide comprises about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90, 100, 200, or up to 300 amino acids. Peptides useful as a binding module can be linear, branched, or cyclic, and can include non-peptidyl moieties. The term "peptide" broadly refers to an amino acid chain that includes naturally occurring amino acids, synthetic amino acids, genetically encoded amino acids, non-genetically encoded amino acids, and combinations thereof. Peptides can include both L-form and D-form amino acids.

A peptide useful as a binding module can be subject to various changes, substitutions, insertions, and deletions where such changes provide for certain advantages in its use. Thus, the term "peptide" encompasses any of a variety of forms of peptide derivatives including, for example, amides, conjugates with proteins, cyclone peptides, polymerized peptides, conservatively substituted variants, analogs, fragments, chemically modified peptides, and peptide mimetics. Any peptide that has desired binding characteristics can be used in the practice of the present invention.

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a peptide having an amino acid residue sequence substantially identical to a sequence of a reference peptide in which one or more residues have been conservatively substituted with a functionally similar residue such that the "conservatively substituted variant" will bind to the same binding partner with substantially the same affinity as the parental variant and will prevent binding of the parental variant. In one embodiment, a conservatively substituted variant displays a similar binding specificity when compared to the reference peptide. The phrase "conservatively substituted variant" also includes peptides wherein a residue is replaced with a chemically derivatized residue.

Examples of conservative substitutions include the substitution of one non-polar (hydrophobic) residue such as isoleucine, valine, leucine or methionine for another; the substitution of one aromatic residue such as tryptophan, tyrosine, or phenylalanine for another; the substitution of one polar (hydrophilic) residue for another such as between arginine and lysine, between glutamine and asparagine, between glycine, alanine, threonine and serine; the substitution of one basic residue such as lysine, arginine or histidine for another; or the substitution of one acidic residue such as aspartic acid or glutamic acid for another.

While exemplary peptide sequences for use as binding modules in IFBMs of the invention are disclosed herein (e.g., in the sequence listing in SEQ ID NOs: 1-74 and 77-558), one of skill will appreciate that the binding or other properties conferred by those sequences may be attributable to only some of the amino acids comprised by the sequences. Peptides which are binding modules of the present invention also include peptides having one or more substitutions, additions and/or deletions of residues relative to the sequence of an exemplary peptide sequence as disclosed herein, so long as the desired binding properties of the binding module are retained. Thus, binding modules of the invention include peptides that differ from the exemplary sequences disclosed herein by about 1, 2, 3, 4, 5, 6, 7, 8, 9, 10, 11, 12, 13, 14, 15, 16, 17, 18, 19, or 20 amino acids, but that retain the ability of the corresponding exemplary sequence to bind to a particular material or to act as an analyte module. A binding module of the invention that differs from an exemplary sequence disclosed herein will retain at least 25%, 50%, 75%, or 100% of the activity of a binding module comprising an entire exemplary sequence disclosed herein as measured using an appropriate assay.

That is, binding modules of the invention include peptides that share sequence identity with the exemplary sequences disclosed herein of at least 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater sequence identity. Sequence identity may be calculated manually or it may be calculated using a computer implementation of a mathematical algorithm, for example, GAP, BESTFIT, BLAST, FASTA, and TFASTA in the Wisconsin Genetics Software Package of Genetics Computer Group, Version 10 (available from Accelrys, 9685 Scranton Road, San Diego, Calif., 92121, USA). The scoring matrix used in Version 10 of the Wisconsin Genetics Software Package is BLOSUM62 (see Henikoff and Henikoff (1989) *Proc. Nat'l. Acad. Sci. USA* 89: 10915). Alignments using these programs can be performed using the default parameters.

A peptide can be modified, for example, by terminal-$NH_2$ acylation (e.g., acetylation, or thioglycolic acid amidation) or by terminal-carboxylamidation (e.g., with ammonia or methylamine). Terminal modifications are useful to reduce susceptibility by proteinase digestion, and to therefore prolong a half-life of peptides in solutions, particularly in biological fluids where proteases can be present.

Peptide cyclization is also a useful modification because of the stable structures formed by cyclization and in view of the biological activities observed for such cyclic peptides. Methods for cyclizing peptides are described, for example, by Schneider & Eberle (1993) *Peptides. 1992: Proceedings of the Twenty-Second European Peptide Symposium*, Sep. 13-19, 1992, Interlaken, Switzerland, Escom, Leiden, The Netherlands.

Optionally, a binding module peptide can comprise one or more amino acids that have been modified to contain one or more halogens, such as fluorine, bromine, or iodine, to facilitate linking to a linker molecule. As used herein, the term "peptide" also encompasses a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), an N-modified bond (—NRCO—), and a thiopeptide bond (CS—NH). See e.g., Garbay-Jaureguiberry et al. (1992) *Int. J. Pept. Protein Res.* 39: 523-527; Tung et al. (1992) *Pept. Res.* 5: 115-118; Urge et al. (1992) *Carbohydr. Res.* 235: 83-93; Corringer et al. (1993) *J. Med. Chem.* 36: 166-172; Pavone et al. (1993) *Int. J. Pept. Protein Res.* 41: 15-20.

Representative peptides that specifically bind to surfaces of interest (including titanium, stainless steel, collagen, and poly glycolic acid (PGA)) and therefore are suitable for use as binding modules in IFBMs of the invention are set forth in the sequence listing and are further described herein below. While exemplary peptide sequences are disclosed herein, one of skill will appreciate that the binding properties conferred by those sequences may be attributable to only some of the amino acids comprised by the sequences. Thus, a sequence which comprises only a portion of an exemplary sequence disclosed herein may have substantially the same binding properties as the full-length exemplary sequence. Thus, also useful as binding modules are sequences that comprise only 3, 4, 5, 6, 7, 8, 9, 10, 11, or 12 of the amino acids in a particular exemplary sequence, and such amino acids may be contiguous or non-contiguous in the exemplary sequence. Such amino acids may be concentrated at the amino-terminal end of the exemplary peptide (for example, 4 amino acids may be concentrated in the first 5, 6, 7, 8, 9, 10, 11, or 12 amino acids of the peptide) or they may be dispersed throughout the exemplary peptide but nevertheless be responsible for the binding properties of the peptide. For example, a peptide that specifically binds to BMP-2 may comprise all or part of a sequence motif such as that described in Example 3 and set forth in SEQ ID NO:27 or 28. Thus, a peptide that specifically binds to BMP-2 may have a sequence that conforms to each requirement of the sequence motif as set forth in SEQ ID NO:27 or 28, or it may have a sequence that conforms to 1, 2, 3, 4, 5, 6, 7, 8, 9, or 10 of the requirements of the sequence motif. The sequence motif set forth in SEQ ID NO:27 can be described as having four "requirements" which limit the amino acids that are present at positions 1, 4, 6, and 7. A peptide that specifically binds to BMP-2 may have a sequence as set forth in SEQ ID NO:11 which conforms to all four of those requirements, or it may have a sequence as set forth in SEQ ID NO:21 which conforms to three of those four requirements. Both of these types of sequences are provided by the present invention.

In some embodiments, the IFBM has been constructed so as to mimic the biological effects of protein growth factors. In these embodiments, the analyte module comprises a peptide which comprises an amino acid sequence which binds to the BMP receptor BMPRI and also comprises an amino acid sequence which binds to the BMP receptor BMPRII (see, for example, Example 6). These receptors are well-known in the art and are also commercially available (for example, from R&D Systems, Minneapolis, Minn., Cat. Nos. 315-BR and 811-BR). In these embodiments, the analyte module has BMP activity as measured, for example, by techniques known in the art and described in Example 6. While the invention is not bound by any particular mechanism of operation, it is believed that by binding to each of BMPRI and BMPRII, the analyte module will encourage the heterodimerization of these receptors, thereby triggering signaling via the BMP-SMAD pathway. In this manner, an IFBM could be constructed and used to coat the surface of an implant so as to trigger signaling via the BMP-SMAD pathway without the addition of BMP itself. Generally, in the native BMP-SMAD pathway, heterodimerization of the BMP type I and type II receptors is required for signaling (see, e.g., Chen et al. (2004) *Growth Factors* 22: 233-241). Dimerization brings the cytoplasmic domains of the type I and type II receptors into proximity, allowing the constitutively active type II receptor kinase to phosphorylate the type I receptor. The phosphorylation of the cytoplasmic domain of the type I receptor activates its latent kinase activity which in turn activates Smad proteins. After release from the receptor, the phosphorylated Smad proteins associate with Smad4 and this complex is translocated into the nucleus to function with other proteins as transcription factors and regulate responsive genes (Chen et al. (2004) *Growth Factors* 22: 233-241). Collectively, this can be referred to as the downstream Smad or BMP-SMAD signal transduction pathway and genes activated thereby. Proteins produced as a result of activation of the Smad or BMP-SMAD pathway can be referred to as Smad-activated downstream protein products.

Binding modules of the present invention that are peptides can be synthesized by any of the techniques that are known to those skilled in the art of peptide synthesis. Representative techniques can be found, for example, in Stewart & Young (1969) *Solid Phase Peptide Synthesis*, (Freeman, San Francisco, Calif.); Merrifield (1969) *Adv. Enzymol. Relat. Areas Mol. Biol.* 32: 221-296; Fields & Noble (1990) *Int. J. Pept. Protein Res.* 35: 161-214; and Bodanszky (1993) *Principles of Peptide Synthesis,* 2nd Rev. Ed. (Springer-Verlag, Berlin). Representative solid phase synthesis techniques can be found in Andersson et al. (2000) *Biopolymers* 55: 227-250, references cited therein, and in U.S. Pat. Nos. 6,015,561; 6,015,881; 6,031,071; and 4,244,946. Peptide synthesis in solution is described in Schröder & Lübke (1965) *The Peptides* (Academic Press, New York, N.Y.). Appropriate protective groups useful for peptide synthesis are described in the above texts and in McOmie (1973) *Protective Groups in Organic Chemistry* (Plenum Press, London). Peptides, including peptides comprising non-genetically encoded amino acids, can also be produced in a cell-free translation system, such as the system described by Shimizu et al. (2001) *Nat Biotechnol* 19: 751-755. In addition, peptides having a specified amino acid sequence can be purchased from commercial sources (e.g., Biopeptide Co., LLC of San Diego, Calif.), and PeptidoGenics of Livermore, Calif.).

The binding modules are connected by at least one linker to form an IFBM of the invention. In some embodiments, IFBMs consisting of binding modules which are peptides are synthesized as a single continuous peptide; in these embodiments, the linker is simply one of the bonds in the peptide. In other embodiments of the invention, a linker can comprise a polymer, including a synthetic polymer or a natural polymer. Representative synthetic polymers which are useful as linkers include but are not limited to: polyethers (e.g., polyethylene glycol; PEG), polyesters (e.g., polylactic acid (PLA) and polyglycolic acid (PGA), polyamides (e.g., nylon), polyamines, polyacrylic acids, polyurethanes, polystyrenes, and other synthetic polymers having a molecular weight of about 200 daltons to about 1000 kilodaltons. Representative natural polymers which are useful as linkers include but are not limited to: hyaluronic acid, alginate, chondroitin sulfate, fibrinogen, fibronectin, albumin, collagen, and other natural polymers having a molecular weight of about 200 daltons to about 20,000 kilodaltons. Polymeric linkers can comprise a diblock polymer, a multi-block copolymer, a comb polymer, a star polymer, a dendritic polymer, a hybrid linear-dendritic polymer, or a random copolymer.

A linker can also comprise a mercapto(amido)carboxylic acid, an acrylamidocarboxylic acid, an acrlyamido-amidotriethylene glycolic acid, and derivatives thereof. See, for example, U.S. Pat. No. 6,280,760. Where a linker comprises a peptide, the peptide can include sequences known to have particular biological functions, such as YGD and GSR.

Methods for linking a linker molecule to a binding domain will vary according to the reactive groups present on each molecule. Protocols for linking using reactive groups and molecules are known to one of skill in the art. See, e.g., Goldman et al. (1997) *Cancer Res.* 57: 1447-1451; Cheng (1996) *Hum. Gene Therapy* 7: 275-282; Neri et al. (1997) *Nat. Biotechnol.* 19: 958-961; Nabel (1997) *Current Protocols in Human Genetics*, vol. on CD-ROM (John Wiley & Sons, New York); Park et al. (1997) *Adv. Pharmacol.* 40: 399-435; Pasqualini et al. (1997) *Nat. Biotechnol.* 15: 542-546; Bauminger & Wilchek (1980) *Meth. Enzymol.* 70: 151-159; U.S. Pat. Nos. 6,280,760 and 6,071,890; and European Patent Nos. 0 439 095 and 0 712 621.

The surfaces of medical devices are coated by any suitable method, for example, by dipping, spraying, or brushing the IFBM onto the device. The coating may be stabilized, for example, by air drying or by lyophilization. However, these treatments are not exclusive, and other coating and stabilization methods may be employed. Suitable methods are known in the art. See, e.g., Harris et al. (2004) *Biomaterials* 25: 4135-4148 and U.S. patent application Ser. No. 10/644,703, filed Aug. 19, 2003 and published on May 6, 2004 with Publication No. 20040087505.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

EXPERIMENTAL

Example 1

Isolation of Peptides that Bind Titanium

Ten different phage display libraries were screened for binding to titanium beads. Titanium ($Ti_6Al_4V$) beads of approximately 5/32 of an inch diameter were washed with 70% ethanol, 40% nitric acid, distilled water, 70% ethanol, and acetone to remove any surface contaminants. One titanium bead was placed per well of 96-well polypropylene plate (Nunc).

Nonspecific binding sites on the titanium and the surface of the polypropylene were blocked with 1% bovine serum albumin (BSA) in phosphate-buffered saline (PBS; Sigma Chemical Co., St. Louis, Mo., Cat. # P-3813). The plate was incubated for 1 hour at room temperature with shaking at 50 rpm. The wells were then washed 5 times with 300 μl of PBS. Each library was diluted in PBS+1% BSA and was added at a concentration of $10^{10}$ pfu/ml in a total volume of 250 μl. After a 3-hour incubation at room temperature and shaking at 50 rpm, unbound phage were removed by washing 3 time with 300 μl of Phosphate Buffered Saline-Tween™ 20 (PBS-T; Sigma Chemical Co., St. Louis, Mo., Cat. # P-3563). To recover the phage bound to the titanium beads, bound phage were released by treating with 50 mM glycine, pH 2 for 10 minutes followed by a 10 minute treatment with 100 mM ethanolamine, pH 12. The eluted phage were pooled, neutralized with 200 μl of 200 mM $NaPO_4$ pH 7. The eluted phage and the beads were added directly to *E. coli* DH5αF' cells in 2xYT media. The mixture was incubated overnight in a 37'C shaker at 210 rpm. Phage supernatant was then harvested after spinning at 8500×g for 10 minutes. Second and third rounds of selection were performed in a similar manner to that of the first round, using the 50 μl of amplified phage from the previous round as input diluted with 200 μl of PBS+1% BSA. The fourth round of selection was carried out in a similar fashion; however, the washes were modified. After a 4 hour binding reaction, the beads were washed five times with PBS-T (Sigma Chemical Co., St. Louis, Mo., Cat. # P-3563), the beads were moved to a clean polypropylene plate with 2 ml wells, 1 ml of PBS+1% BSA was added to each well and the washing was incubated overnight at room temperature with shaking at 50 rpm. The next morning the phage were eluted and amplified in the same manner described for rounds 1-3. Individual clonal phage were then isolated and tested by plating out dilutions of phage pools to obtain single plaques.

To detect phage that specifically bound to titanium, conventional ELISAs were performed using an anti-M13 phage antibody conjugated to HRP, followed by the addition of chromogenic agent ABTS. Relative binding strengths of the phage were determined by testing serial dilutions of the phage for binding to titanium in an ELISA.

The DNA sequence encoding peptides that specifically bound titanium was determined. The sequence encoding the peptide insert was located in the phage genome and translated to yield the corresponding amino acid sequence displayed on the phage surface.

Representative peptides that specifically bind titanium are listed in Table 1 and are set forth as SEQ ID NOs:1-8. The binding of phage displaying these peptides to titanium beads is shown in FIG. 1.

TABLE 1

Titanium Binding Peptides

| Clone Number | Synthetic Peptide Number | Displayed Peptide | SEQ. ID. NO. |
|---|---|---|---|
| AP06-22 | AFF-6002 | SSHKHPVTPRFFVVESR | 1 |
| AP06-23 | AFF-6003 | SSCNCYVTPNLLKHKCYKICSR | 2 |
| AP06-24 | AFF-6004 | SSCSHNHHKLTAKHQVAHKCSR | 3 |
| AP06-25 | AFF-6005 | SSCDQNDIFYTSKKSHKSHCSR | 4 |
| AP06-26 | AFF-6006 | SSSSDVYLVSHKHHLTRHNSSR | 5 |
| AP06-27 | AFF-6007 | SSSDKCHKHWYCYESKYGGSSR | 6 |
| AP06-28 | | HHKLKHQMLHLNGG | 7 |
| AP06-29 | | GHHHKKDQLPQLGG | 8 |

Figure 2:
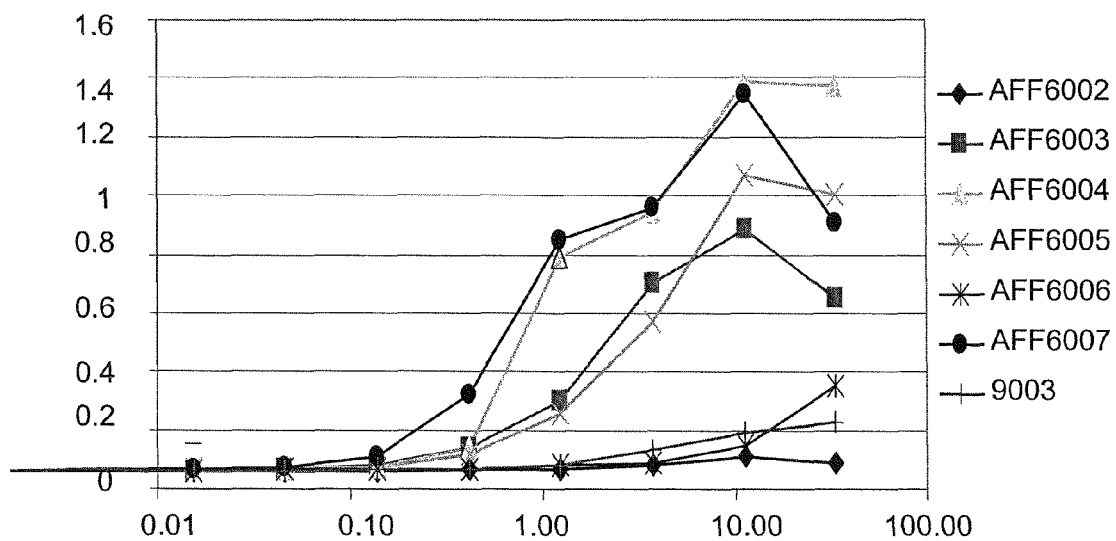
FIG. 2 shows a comparison of the binding of peptides with a C-terminal biotin residue to titanium (see Example 1). Absorbance (vertical axis) is shown as a function of peptide concentration ($\mu M$, on the horizontal axis).

The displayed peptides were then synthesized with a C-terminal biotin residue and tested for binding to titanium. Results are shown in FIG. 2. Briefly, peptide stock solutions were made by dissolving the powder in 100% DMSO to make a 1 mM solution of peptide. Serial dilutions of the peptide were made in PBS-T. Titanium beads blocked with 1% non-fat dry milk in PBS were incubated with various concentrations of peptide for 1 hour at room temperature with shaking. The beads were washed 3 times with PBS-T. Streptavidin-alkaline phosphatase (SA-AP) from USB (United States Biochemical, catalog #11687) was added (1:1000 in PBS-T) and incubated 1 hour at room temperature with shaking The beads were washed 3 times with PBS-T and the amount of peptide: SA-AP was determined by adding PNPP (Sigma-Aldrich, Inc., SigmaFast tablets, catalog #N1891) and allowing the color to develop for about 10 minutes. Quantitation was carried out by transferring the solution to a clear microtiter plate and reading the absorbance at 405 nm on a Molecular Dynamics Plate Reader. The peptide "9003" is known in the art. This peptide was identified by phage display as binding to the enzyme hexokinase; it serves as a negative control for this experiment (see, e.g., Hyde-DeRuyscher et al. (2000) *Chem. Biol.* 7: 17-25).

Example 2

Role of Cysteine Residues in Titanium-Binding Peptide 6007

To explore the role of the cysteine residues and disulfide formation in the binding of peptide 6007 to titanium, a peptide was synthesized AFF6010 (Table 2) in which the cysteine residues present in the titanium-binding peptide AFF6007 were changed to serine residues. The sequence of peptide AFF6010 (SSSDKSHKHWYSYESKYGGSGSSGK) is set forth in SEQ ID NO:9, while the sequence of peptide AFF6007 (SSSDKCHKHWYCYESKYGGSGSSGK) is set forth in SEQ ID NO:10. The peptides AFF6007 and AFF6010 were then conjugated to biotin and compared for binding to titanium beads as follows.

Titanium beads were blocked with 1% BSA in PBS for 30 minutes at room temperature. Stock solutions of peptide AFF6007 and AFF6010 were prepared by dissolving 1-2 mg peptide in water. The final concentration of each peptide was determined using the optical density at 280 nm and the extinction coefficient of each peptide. AFF6007 and AFF6010 were prepared at 200 µM. A dilution series was then prepared for each peptide sample. Each peptide underwent a threefold dilution in 1% BSA in PBS.

The peptides were incubated with the titanium beads for 1 hour at room temperature. Beads were then washed two times with PBS/Tween™ 20. Streptavidin-alkaline phosphatase was then added to the beads at 1:500 for 30 minutes at room temperature. Beads were washed two times with PBS/Tween™ 20. PNPP was used to develop the assay and the absorbance was recorded at 405 nm.

Figure 3:
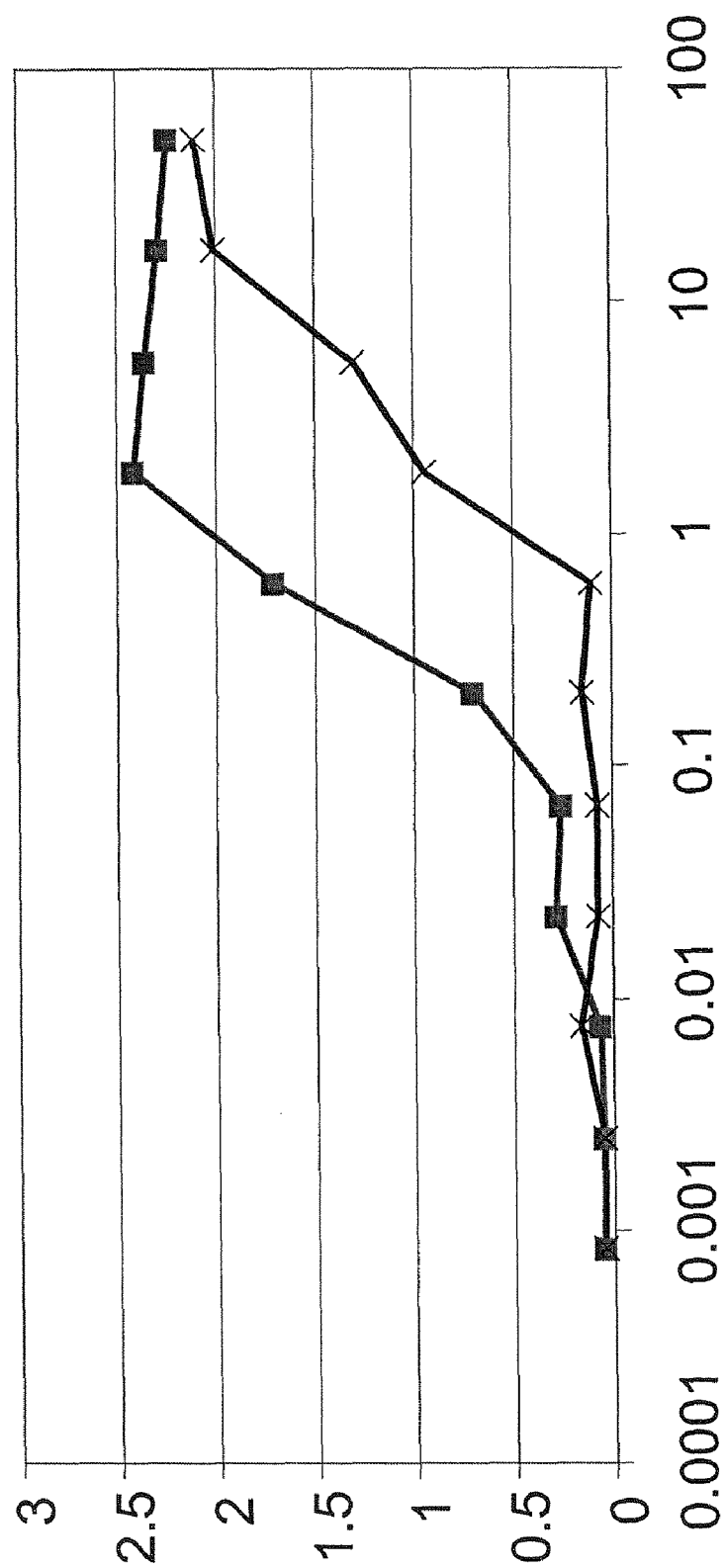
FIG. 3 shows a comparison of binding to titanium of two peptides (see Example 2). A405 nm signal (vertical axis) is shown as a function of peptide concentration ($\mu M$, on the horizontal axis). The lines shown on the graph from top to bottom join data points for peptides AFF6007 and AFF6010, respectively.

The results, which are shown in FIG. 3, demonstrate that peptides AFF6007 and AFF6010 both bind to titanium. An estimate of the relative affinity of a peptide for titanium can be made by determining the concentration of peptide that gives one-half the maximal signal (Table 2). The complete elimination of the cysteine residues in AFF6007 decreases the affinity of the peptide for titanium by about 10-fold but does not eliminate it (Table 2). Therefore, the cysteine residues are not required for binding to titanium but do increase the affinity of the peptide for titanium.

TABLE 2

Relative Affinity of Titanium-binding Peptides

| Sample | [peptide] ½ maximal signal |
|---|---|
| AFF6007 | 0.35 µM |
| AFF6010 | 3 µM |

Example 3

Peptides that Specifically Bind to Bone Morphogenic Protein 2 ("BMP-2")

Isolation and Analysis of Peptides

Ten different phage display libraries were screened for binding to BMP-2. BMP-2 (Medtronic) was biotinylated with NHS-biotin (Pierce) to produce a labeled protein with an average of one biotin per protein molecule. This protein was immobilized on streptavidin (SA) coated plates and used as target for phage display. As an alternative method to display the protein, BMP-2 was also linked to sepharose beads using NHS-succinimide chemistry according to the instructions of the manufacturer (Amersham-Pharmacia, Ref. No. 18-1022-29, entitled "Coupling through the Primary Amine of a Ligand to NHS-activated Sepharose 4 Fast Flow," pp. 105-108) and the beads were used as a solid phase to separate free from unbound phage. After 3 rounds of selection, individual clones from each format were tested for binding to BMP-2 on SA coated plates utilizing a conventional ELISA using an anti-M13 phage antibody conjugated to HRP, followed by the addition of chromogenic agent ABTS.

The DNA sequence encoding peptides that specifically bound to BMP-2 was determined. The sequence encoding the peptide insert was located in the phage genome and translated to yield the corresponding amino acid sequence displayed on the phage surface. Representative peptides that specifically bind BMP-2 are listed in Table 3 and are set forth as SEQ ID NOs:11-26. In some embodiments, an exemplary binding module of the invention comprises only that portion of the sequence shown in uppercase letters.

TABLE 3

Peptides that Specifically Bind to BMP-2

| Clone Number | Synthetic Peptide Number | Sequence | SEQ. ID. NO. |
|---|---|---|---|
| AP02-45 | AFF-2011 | ssDWGVVASAWDAFEALDAsr | 11 |
| AP02-46 | | ssGADFGYGSWVSFSALSAsr | 12 |
| AP02-47 | | srGEASGWEAFSALEAAVVsr | 13 |
| AP02-48 | AFF-2006 | srSSDSAFSSFSALEGSVVsr | 14 |
| AP02-49 | | srDGAGAAAWGAFSALASEsr | 15 |
| AP02-50 | AFF-2007 | srGGEAAAGAWVSFSALESsr | 16 |
| AP02-51 | | srVSGVAAWEAFAGLSVSSsr | 17 |
| AP02-52 | AFF-2010 | srDGGSFSAFSSLVWAADSsr | 18 |
| AP02-53 | | ssVAGDVGSSWAAFASLAAsr | 19 |
| AP02-54 | AFF-2008 | ssWEVFSSLESGSVGAGAGsr | 20 |
| AP02-55 | | ssSSGAVSSFESLSGSVVSsr | 21 |
| AP02-56 | | srEGVAWEAFGALSSFAADsr | 22 |
| AP02-57 | | ssWGLASEASFFSFSALSSsr | 23 |
| AP02-58 | | srEGAAWDSFFALSGGSAAsr | 24 |
| AP02-59 | AFF-2012 | ssSVDLYFPLKGDVVsr | 25 |
| AP02-60 | AFF-2009 | ssFEPLRFPLKGVPVsr | 26 |

The peptides that were identified fall into 2 different "sequence clusters". Each sequence cluster contains a common sequence motif. For the first sequence cluster of BMP-binding peptides, the common motif (designated "Motif 1" and set forth in SEQ ID NO:27) is Aromatic-X-X-Phe-X-"Small"-Leu (Aromatic=Trp, Phe, or Tyr; X=any amino acid; "Small"=Ser, Thr, Ala, or Gly). Motif 1 is at least partially found in SEQ ID NOs:11-24 as shown in Table 3 above. The second sequence cluster motif (also set forth in SEQ ID NO:28) comprises the sequence (Leu or Val)-X-Phe-Pro-Leu-(Lys or Arg)-Gly. This motif, designated Motif 2, is found in SEQ ID NOs:25 and 26 as shown in Table 3 above. Exemplary binding modules also comprise sequences which meet the requirements of this or other sequence motifs identified herein (i.e., which contain a sequence which falls within these motifs).

Additional experiments were conducted to determine additional characteristics of sequences that bind to BMP-2. Specifically, in order to determine whether there were additional preferred amino acids surrounding these motifs, further screening was conducted. Focused libraries were designed and cloned into the mAEK phage display vector and the resultant phage were screened for binding to BMP-2, as further discussed below. The focused library for Motif 1 was designed to express peptides containing the following sequence: X-X-X-X-X-(W/L/C/Y/F/S)-X-X-(W/L/C/Y/F/S)-X-(A/G/N/S/T)-(L/F/I/M/V)-X-X-X-X-X, where X represents any of the 20 naturally occurring amino acids and positions in parentheses are restricted to the amino acids listed within the parentheses. These peptides were encoded by oligonucleotides comprising the sequence 5'-GATCCTC-GAGNNNKNNKNNKNNKNNKTNBNNKNNK-TNBNNKRSYNTKNNKN NKNNKNNKNNKTCTA-GAGCGCTACG 3' (where "N" is any of the 4 nucleotides A, G, C, or T; "K" is G or T; "R" is A or G; "S" is C or G; "B" is C, G, or T; and "Y" is C or T). The focused library for Motif 2 was designed to express peptides containing the following sequence: X-X-X-(L/F/I/M/V)-X-(W/L/C/Y/F/S)-(P/S/T/A)-(L/F/I/M/V)-(I/M/T/N/K/S/R)-X-X-X-X-X-X-X-X. These peptides were encoded by oligonucleotides comprising the sequence 5'-GATCCTCGANNNKNNKNNKNT-KNNKTNBNCKNTKANKNNKNNKNNKNNKNN KNN-KNNKNNKTCTAGAGCGCTACG 3'.

The following is provided as an exemplary library construction scheme for the Motif 1 focused library. As will be appreciated by one of skill in the art, a similar strategy can be used for other libraries. To produce the focused library for Motif 1, an oligonucleotide comprising the sequence above flanked by appropriate restriction enzyme sites was synthesized. This oligonucleotide contained the sequence 5'-GATC <u>CTCGAG</u>NNNKNNKNNKNNKNNKTNBNNKNNKTNB NNKRSYNTKNNKNNKN NKNNKNNK<u>TCTAGA</u> GCGC TACG-3'. In this sequence, the underlined sequences CTC-GAG and TCTAGA represent the XhoI and XbaI restriction enzyme sites used to clone the library into the phage vector. A short primer is annealed to the oligonucleotide and the complementary strand synthesized using a DNA polymerase. The resulting double-stranded DNA molecule is digested with XhoI and XbaI and cloned into the phage display vector. The ligated DNA is transformed into an appropriate bacterial host and amplified to generate the phage library.

The focused libraries for Motif 1 and Motif 2 were screened for binding to BMP-2 using biotinylated BMP-2 immobilized on streptavidin-coated plates as described above. After two rounds of selection on BMP-2, the libraries had been enriched for phage displaying peptides that bind to BMP-2. The pools of enriched phage were plated onto a lawn of bacterial cells to isolate individual phage. Individual phage clones were tested for binding to BMP-2 using an ELISA-type assay and an anti-M13 phage antibody conjugated to HRP (Amersham Biosciences # 27-9421-01), followed by addition of the chromogenic reagent ABTS (Sigma Chemical Co., St. Louis, Mo., Cat. # A3219).

The DNA sequence encoding peptides that specifically bound to BMP-2 was determined. The sequence encoding the peptide insert was located in the phage genome and translated to yield the corresponding amino acid sequence displayed on the phage surface.

Representative peptides from the motif-based focused libraries that specifically bind BMP-2 are listed in Tables 4 and 5 and are set forth as SEQ ID NOs:44-71 and 77-92. In some embodiments, an exemplary binding module of the invention comprises only that portion of the sequence shown in uppercase letters, or comprises only a sequence falling within a motif or a consensus sequence identified based on these sequences (i.e., comprises a sequence falling within the scope of Motif 1, Motif 1a, or Motif 2, or comprises the consensus sequence identified in SEQ ID NO:72, 74, or 93).

TABLE 4

BMP Binding Peptides from Motif 1 Focused Library

| Clone ID | Sequence | SEQ. ID NO. |
|---|---|---|
| AP02-01 | ssAPLTESEAWRGFSKLEVsr | 44 |
| AP02-02 | ssSMPVGWDSWRGLEWSDRsr | 45 |
| AP02-03 | ssEGRGGWNSWEAFRELVVsr | 46 |
| AP02-04 | ssGGGGAWESWRGLSGVELsr | 47 |
| AP02-05 | srNVEGSWESFAGLSHVREsr | 48 |
| AP02-06 | srEDGGRWESFLGLSAVEVsr | 49 |
| AP02-07 | ssVEGSAWSAFKSLSSEGVsr | 50 |
| AP02-08 | srVEGGAWQALAGLTVERVsr | 51 |
| AP02-09 | ssPPKHAWGSFDALGGQVVsr | 52 |
| AP02-10 | ssERGVGWEVFLAMEGARMsr | 53 |
| AP02-11 | ssSSSGTWQAFTGLSGERVsr | 54 |
| AP02-12 | ssSPGGGSGGWDAFYSLVGsr | 55 |
| AP02-13 | ssGGGGGGEGFSSLSGNGRsr | 56 |
| AP02-14 | ssTGGGSWEEFKAMTPSWTsr | 57 |
| AP02-15 | ssEGSGLWDSFSSLSVHEVsr | 58 |
| AP02-16 | ssGVTQESASWSSFRTLAVsr | 59 |
| AP02-17 | ssSKVAPSGEWRSFATLEVsr | 60 |
| AP02-18 | ssEAGRGWEGFKALEGYQVsr | 61 |
| AP02-19 | ssLGQTGWEAFESLSGTRGsr | 62 |
| AP02-20 | ssVAWDAFTVFESLEGVATsr | 63 |
| AP02-21 | ssEVVEPWEWWVALERAGGsr | 64 |
| AP02-22 | srVAAVSWEFFGSLSSAGVsr | 65 |
| AP02-23 | ssADLGVSGSWEGFALMRGsr | 66 |
| AP02-24 | ssVGQMGWEAFESLSGTGGsr | 67 |
| AP02-25 | ssGQGETWEWFAGMRGSVAsr | 68 |
| AP02-26 | ssYFDVFSSMTGTRAAGSWsr | 69 |
| AP02-27 | ssAYSVFSSLRADNSGGAVsr | 70 |
| AP02-44 | ssGGIASLKYDVVKTWEsr | 71 |

TABLE 5

BMP-Binding Peptides from Motif-2 Focused Library

| Clone ID | Sequence | SEQ. ID. NO.: |
|---|---|---|
| AP02-28 | ssEGVGGFPLKGIPQEAWAsr | 77 |
| AP02-29 | ssPSGVVFPLRGELLGVXKsr | 78 |
| AP02-30 | ssGGFVPFPLRGEVWDGVHsr | 79 |
| AP02-31 | ssEGSLSFPLKGQVYSGWGsr | 80 |
| AP02-32 | ssGKPLEFPLRGTLAEWPVsr | 81 |
| AP02-33 | srGEALGFPLTGQLMEAAEsr | 82 |
| AP02-34 | ssMWDVGFPLKGRWIDGADsr | 83 |
| AP02-35 | ssSNSLWFPLRGSTVEVGAsr | 84 |
| AP02-36 | ssGPALRLPLRGTVVSDVPsr | 85 |
| AP02-37 | ssADRVAWPLKGAPVWVKEsr | 86 |
| AP02-38 | ssGLALGLPIKGWTVSGKDsr | 87 |
| AP02-39 | ssGYTLGFPLSGQTIKDWPsr | 88 |
| AP02-40 | ssEGWVHFPLKGDVMGGPFsr | 89 |
| AP02-41 | ssGRYVSLPLKGEVVPQTAsr | 90 |
| AP02-42 | ssEGGVGFPLKGIPQEAWAsr | 91 |
| AP02-43 | srVDSVNFPLRGETVTSMVsr | 92 |

The results of an analysis of all the peptide sequences from Tables 3 and 4 that bind BMP-2 and contain Motif 1 was generated and is shown in FIG. 7. From an alignment of the 40 BMP-binding sequences that contain Motif 1, a consensus sequence can be derived (Gly-Gly-Gly-Ala-Trp-Glu-Ala-Phe-Ser-Ser-Leu-Ser-Gly-Ser-Arg-Val; SEQ ID NO: 72) that represents the predominant amino acid found at each position after all the peptides are aligned. Among the 40 sequences, the most conserved amino acids form a core binding motif which represents a subset of all sequences containing Motif 1. This motif, designated "Motif 1a," has the sequence Trp-X-X-Phe-X-X-Leu (SEQ ID NO: 73). While the invention is not bound by any particular mechanism of action, it is believed that in this motif, the Trp, Phe, and Leu residues on the peptide participate in specific interactions with the BMP-2 protein that are responsible for the binding of the peptide to BMP. On this basis, it was hypothesized that other peptides that contain this core binding motif will also bind to BMP.

Figure 9:
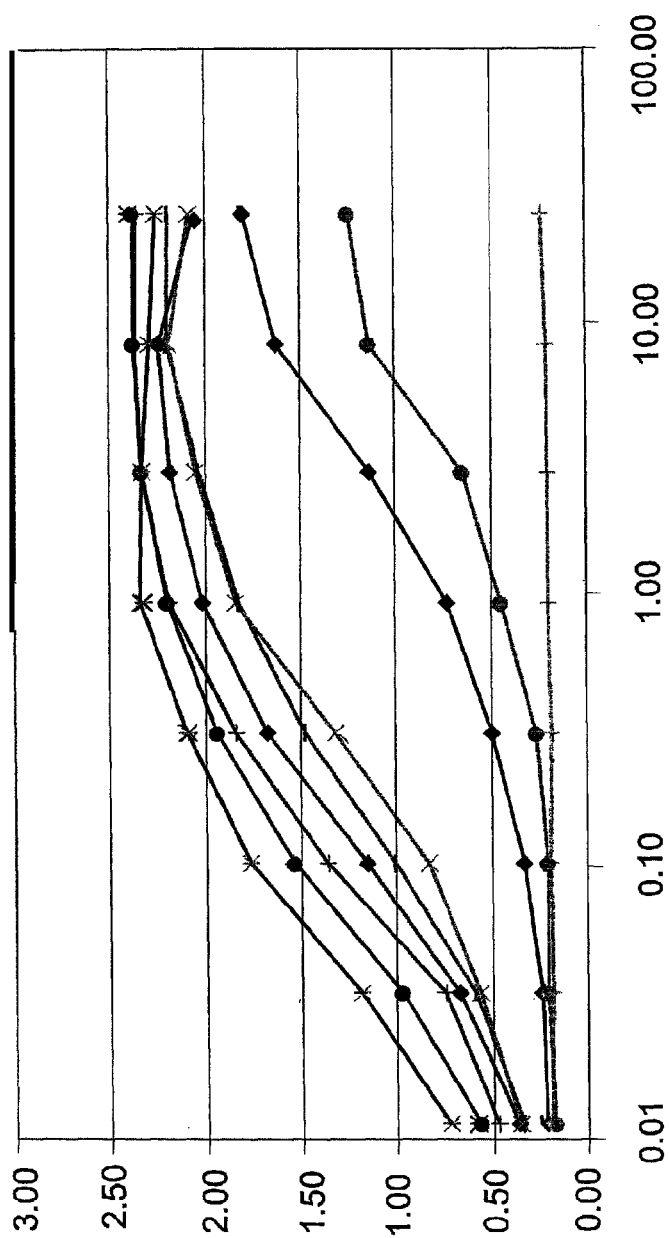
FIG. 9 shows results from a conventional ELISA performed to evaluate the relative affinity of BMP binding peptides (see Example 3). The signal from the ELISA (A405 nm reading) is presented on the vertical axis as a function of microliters of phage on the horizontal axis. At the data points corresponding to 0.10 microliters of phage, the lines shown on the graph from top to bottom join data points for: APO2-61, APO2-40, APO2-41, APO2-26, APO2-35, APO2-59, APO2-44, mAEK, and the no-phage control, respectively.

To test this idea, an oligonucleotide cassette was designed to express a peptide which contained this core binding Motif 1a in the context of a peptide sequence which also contained consensus residues identified for other positions in the sequence that flanked the core binding motif (see FIG. 8; SEQ ID NO: 74). Incidentally, none of the BMP-binding peptides previously isolated by phage display actually contain this exact sequence (see, e.g., Table 4). This oligonucleotide cassette was cloned into the mAEK phage display vector and the resulting phage, designated AP02-61, was tested for binding to BMP-2 and compared to other phage displaying BMP-binding peptides (results for some phage are shown in FIG. 9). At least one phage tested (designated AP02-37) showed binding at a level equivalent to or below that of the display vector mAEK. In some embodiments, an exemplary binding module of the invention comprises only that portion of the sequence shown in uppercase letters.

From an alignment of the peptides from Tables 3 and 5 that contain Motif 2, a consensus sequence can be derived (Gly-Gly-Ala-Leu-Gly-Phe-Pro-Leu-Lys-Gly-Glu-Val-Val-Glu-Gly-Trp-Ala; SEQ ID NO: 93; see FIG. 10) that represents the predominant amino acid found at each position after all the peptides are aligned. Among the sequences examined, the most conserved amino acids form a core binding motif designated "Motif 2a," which has the sequence Leu-X-Phe-Pro-Leu-Lys-Gly (SEQ ID NO: 94).

Motif 2 appears to be more restricted in sequence than Motif 1 in that Motif 2 imposes requirements on six positions whereas Motif 1 only imposes requirements on three positions. The Pro and Gly residues in Motif 2 appear to be required for binding since every Motif 2-containing BMP-binding peptide contains the Pro and Gly residues found in the core binding motif. Using the consensus sequence information for Motif 2, BMP-binding peptides can be designed by incorporating the Motif 2 core binding motif into the peptide sequence.

Production of Synthetic Peptides and BMP-2 Binding Assays

Figure 4:
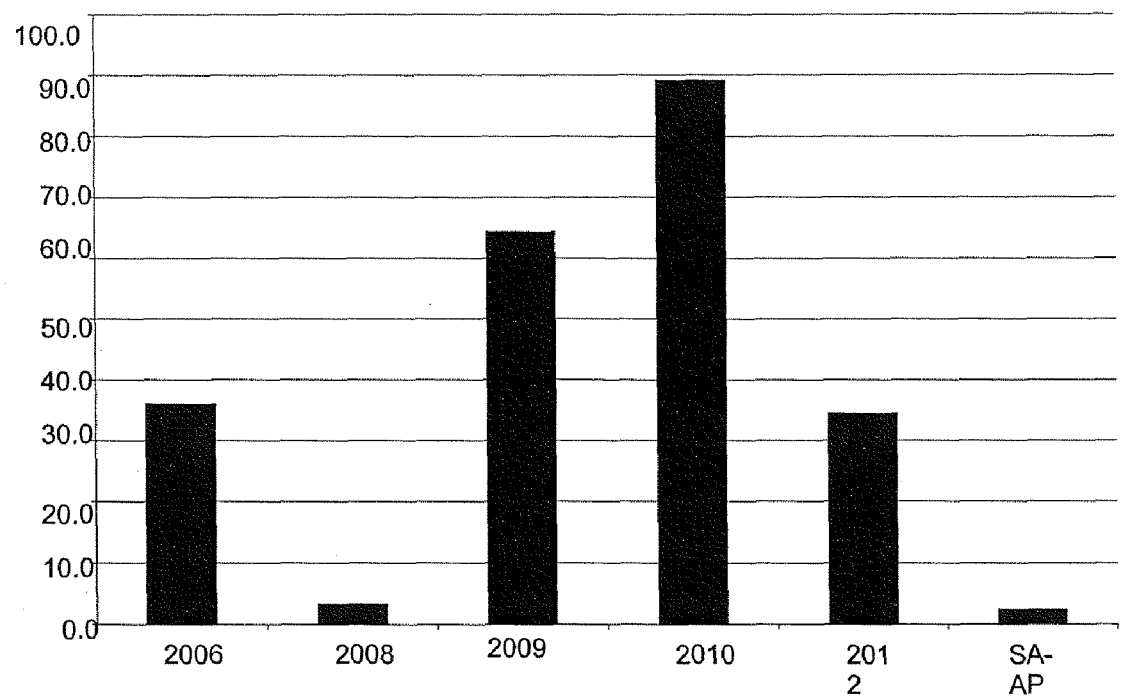
FIG. 4 shows a comparison of binding of various peptides to BMP-2 (see Example 3). Signal (rate AP) is shown for various peptides (identified on the horizontal axis).

A representative set of the displayed peptides were then synthesized with a C-terminal biotin residue and tested for binding to BMP-2. Results are shown in FIG. 4. Briefly, peptide stock solutions were made by dissolving the powder in 100% DMSO to make a 10 mM solution of peptide, water was then added for a final stock concentration of peptide of 1 mM in 10% DMSO. Serial dilutions of the peptide were made in PBS-T. A dilution series of BMP-2 with concentrations ranging from 100 nM to 0.1 nM was immobilized onto the wells of microtiter plates (Immulon-4® HBX from Dynex Technologies, Chantilly, Va.) and blocked with 1% BSA. These plates were incubated with various concentrations of peptide for 1 hour at room temperature with shaking. The beads were washed 3 times with PBS-T. Streptavidin-alkaline phosphatase (SA-AP) from USB (United States Biochemical, catalog #11687) was added (1:1000 in PBS-T) and incubated 1 hour at room temperature with shaking. The plates were washed 3 times with PBS-T and the amount of peptide:SA-AP was determined by adding PNPP (Sigma-Aldrich, Inc., SigmaFast tablets, catalog #N1891) and allowing the color to develop for about 10 minutes. Quantitation was carried out by reading the absorbance at 405 nm on a Molecular Dynamics Plate Reader. The results are summarized in FIG. 4.

Figure 11:
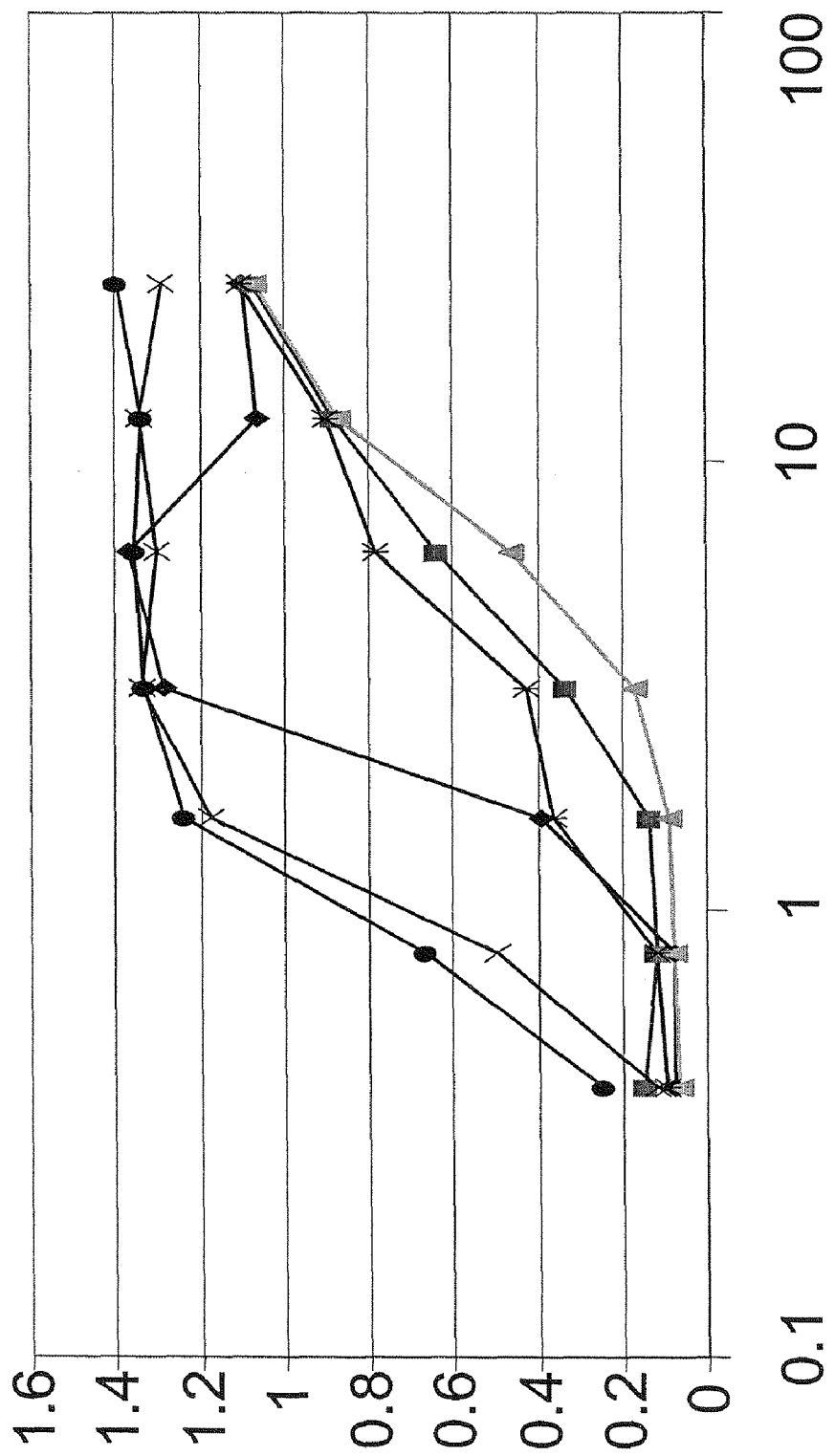
FIG. 11 shows representative results from an alternate assay for BMP-binding activity in which binding occurs in the solution phase (see Example 3). Absorbance at 405 nm (vertical axis) is shown as a function of picomoles of BMP (horizontal axis). These results were used to calculate the affinity of each BMP-binding peptide for BMP-2 (see Table 6). At the data point corresponding to one picomole of BMP, the lines shown on the graph from top to bottom join data points for: 2006, 2007, 2008, 2009, 2011, and 2012, respectively.
Figure 12:
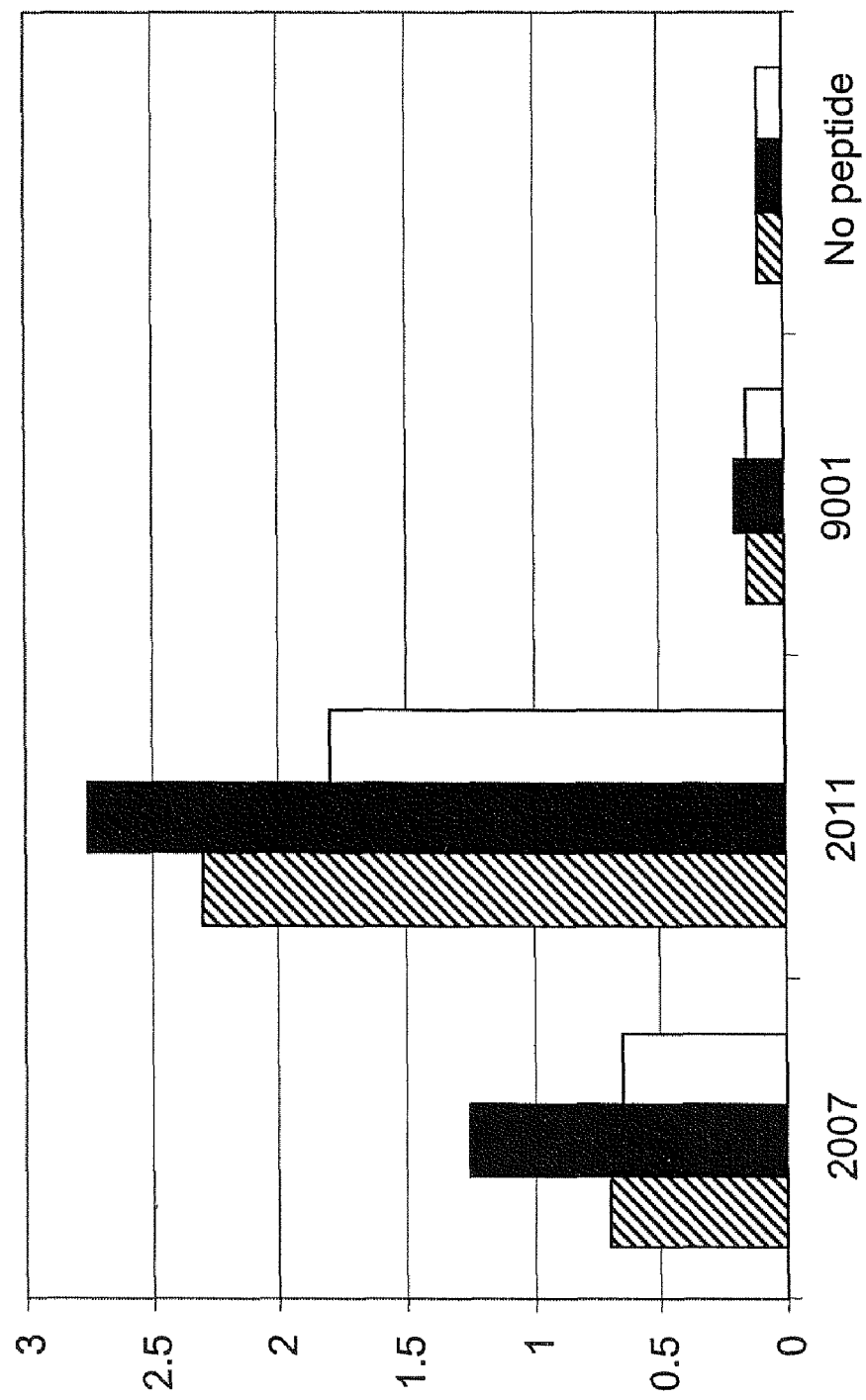
FIG. 12 shows results from an assay in which several peptides were tested for their ability to bind to BMP-2, BMP-4, and BMP-7 (see Example 3). The 2007 and 2011 peptides were originally identified as BMP-2 binding peptides, while the 9001 peptide was originally identified as binding to an unrelated target.

To confirm these BMP binding results, the peptides were also tested in an alternate assay format in which the peptide and BMP2 were allowed to bind in solution and then assayed. Briefly, the peptides were synthesized with a biotin group attached to the ε amino group of a lysine residue at the C-terminus of the peptide. The biotinylated peptides (0-12 pmoles) were mixed with BMP-2 (0-25 pmoles) in solution and allowed to incubate at 37° C. for 30 minutes in a polypropylene plate. The solutions were transferred to a streptavidin-coated plate and incubated for 1 hour at 37° C. to capture the biotinylated peptides. Plates were washed in TBS-Tween™ 20 and then incubated with an anti-BMP antibody (1:1000 dilution; R&D systems) for 1 hour at RT. After washing, an alkaline phosphatase-labeled secondary antibody was then added to the plate and incubated at RT for 30 minutes. The plates were washed with TBS-Tween™ 20 and the antibody binding was detected using the chromogenic AP substrate pNPP. Representative results are shown in FIG. 11. From this data, the affinity of each BMP-binding peptide for BMP-2 was calculated (Table 6).

TABLE 6

Estimated Affinity of BMP-binding Peptides for BMP-2

| Peptide | Estimated Affinity (nM) |
|---|---|
| 2012 | 9 |
| 2009 | 10 |
| 2006 | 21 |
| 2011 | 55 |
| 2007 | 79 |
| 2008 | 99 |

BMP-2 Binding Peptides Bind to Other BMP Proteins

Bone Morphogenetic Proteins (BMPs) are members of the TGF-beta superfamily which includes BMPs, Transforming Growth Factor-beta (TGF-β) and Growth/Differentiation factors (GDFs). The proteins in the TGF-β superfamily are very similar structurally. The folded structure of the protein backbone is almost identical among all the members of the family. Based on the similarity in structure between the BMPs, we tested the ability of some of the BMP-2-binding peptides to bind BMP-4 and BMP-7. Biotinylated peptides 2007 and 2011 were tested for binding to BMP-2, BMP-4, and BMP-7 as described above. Both 2007 and 2011 bound to all three BMPs while a peptide that binds to an unrelated target (AFF-9001) did not bind to any of the BMPs (FIG. 12).

Example 4

Generation of an IFBM that Immobilizes BMP-2 onto Collagen

To design a molecule with collagen and BMP-2 binding properties, an IFBM was created that comprised a peptide that binds to collagen and a peptide that binds to BMP-2. Examples of this "hybrid peptide" IFBM are shown in Table 7.

TABLE 7

IFBMs that bind to Collagen and BMP-2

| IFBM # | Peptides | Peptide Sequence | SEQ ID NO: |
|---|---|---|---|
| AFF 7005 | 2009-0016 | SSFEPLRFPLKGVPVSR*GSSGK*DVNSIWMSRVIEWTYDS-NH2 | 29 |
| AFF 7006 | 0016-2009 | DVNSIWMSRVIEWTYDS*GSSGK*SSFEPLRFPLKGVPVSR-NH2 | 30 |
| AFF 7007 | 2006-0016 | SRSSDSAFSSFSALEGSVVSR*GSSGK*DVNSIWMSRVIEWTYDS-NH2 | 31 |
| AFF 7008 | 0016-2006 | DVNSIWMSRVIEWTYDS*GSSGK*SRSSDSAFSSFSALEGSVVSR-NH2 | 32 |
| AFF 7009 | 2012-0016 | SSSVDLYFPLKGDVVSR*GSSGK*DVNSIWMSRVIEWTYDS-NH2 | 33 |
| AFF 7010 | 0016-2012 | DVNSIWMSRVIEWTYDS*GSSGK*SSSVDLYFPLKGDVVSR-NH2 | 34 |
| AFF 7014 | 2007-0016 | SRGGEAAAGAWVSFSALESSR*GSSGK*DVNSIWMSRVIEWTYDS-NH2 | 35 |
| AFF 7015 | 0016-2007 | DVNSIWMSRVIEWTYDS*GSSGK*SRGGEAAAGAWVSFSALESSR-NH2 | 36 |
| AFF 7016 | 2011-0016 | SSDWGVVASAWDAFEALDASR*GSSGK*DVNSIWMSRVIEWTYDS-NH2 | 37 |
| AFF 7017 | 0016-2011 | DVNSIWMSRVIEWTYDS*GSSGK*SSDWGVVASAWDAFEALDASR-NH2 | 38 |

As shown in Table 7, each IFBM contains the collagen binding domain from AFF0016 followed by a short linker sequence which is then linked to a BMP binding sequence from the above example in a "hybrid peptide." These molecules were synthesized in both orientations to assess the effect of N- or C-terminal locations on the ability of the IFBM to bind to collagen or BMP-2.

To determine if these IFBM's increased the amount of BMP retained by a collagen sponge, we mixed the IFBM with BMP, added the mixture to a sponge, allowed them to bind for 1.5 hours, washed the sponge and detected the bound BMP with anti-BMP antibodies. Briefly, stock IFBM solutions were prepared by weighing 1-2 mg peptide and solubilizing in water. The final peptide concentration was determined by analyzing the peptide absorbance at 280 nm and the extinction coefficient. For each row, 20 µL of peptide were added to each well of a polypropylene microtiter plate. BMP was then added to each of these wells in a threefold dilution series, starting with 32 µM BMP. The IFBM and BMP were allowed to mix at room temperature for 30 minutes.

To each well, a 2/16" diameter collagen sponge (Medtronic) was added. The collagen and peptide solutions were allowed to incubate for 1.5 hours at room temperature. Sponges were then rinsed three times with 200 µL Medtronic buffer at 2200 rpm for 1 minute. To each sponge, a primary antibody directed at BMP (diluted 1:1000; R&D Systems #MAB3552) was added for 1 hour at room temperature. A secondary antibody conjugated to alkaline phosphatase (1:5000) was then incubated in the system for 0.5 hour at room temperature. PNPP was used to develop the system and absorbances were read at 405 nm. Results are shown in FIG. 5.

Figure 5:
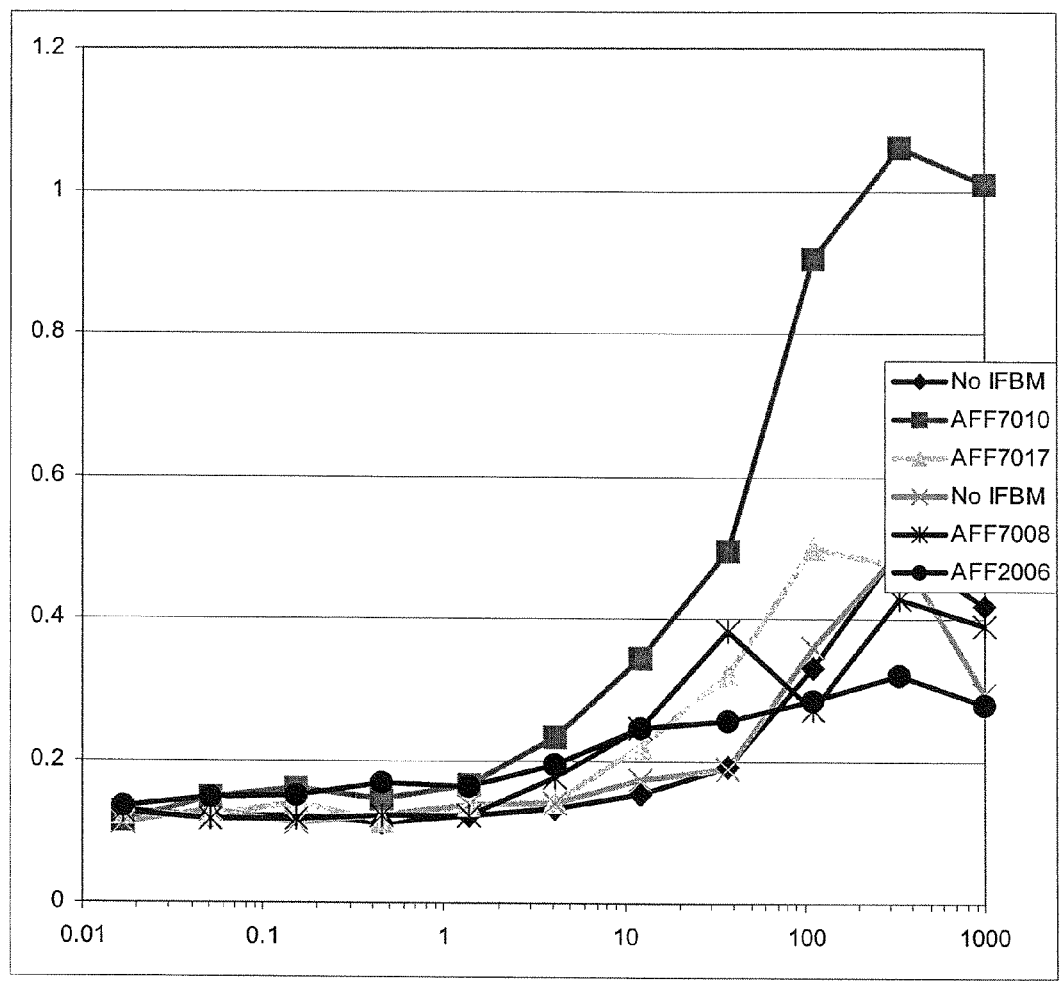
FIG. 5 shows the effect of BMP on the binding of IFBMs to a collagen sponge (see Example 4). Signal (vertical axis) is shown as a function of BMP concentration in nM (horizontal axis).

The results shown in FIG. 5 demonstrate that IFBM AFF7010 retains more BMP on the sponge than the sponges without IFBM. IFBM AFF7008 and AFF7017 increase the amount of BMP on the sponge when compared to no IFBM, but to a lesser extent than AFF7010. The increased retention of BMP to the sponge is not seen by adding AFF2006, a BMP-binding peptide that does not contain a collagen-binding sequence.

To show that this effect is dose dependent not only on the amount of BMP put onto the sponge but also on the amount of IFBM present, a series of two-dimensional dose response curves was obtained in which the concentrations of both the IFBM and BMP were varied. These results are shown in the FIGS. 6A-6D and demonstrate that the binding of BMP to the collagen sponge is dependent on both BMP concentration and IFBM concentration. Increasing the concentration of the IFBM (AFF7005, AFF7006, AFF7009, or AFF7010) leads to a larger amount of BMP-2 that is retained on the collagen.

Example 5

Peptides that Bind to Stainless Steel

Selection of stainless steel-binding peptides was performed as described above for the titanium-binding peptides except that 5/32 inch stainless steel beads were used instead of titanium beads. The stainless steel binding peptides that were isolated are shown in Table 8. In some embodiments, an exemplary binding module of the invention comprises only that portion of the sequence shown in uppercase letters.

TABLE 8

Stainless Steel Binding Peptides

| Phage Designation | Peptide Sequence | SEQ ID NO: |
|---|---|---|
| AP08-03 | ssSSYFNLGLVKHNHVRHHDSsr | 39 |
| AP08-02 | ssCHDHSNKYLKSWKHQQNCsr | 40 |
| AP08-01 | ssSCKHDSEFIKKHVHAVKKCsr | 41 |
| AP08-04 | ssSCHHLKHNTHKESKMHHECsr | 42 |
| AP08-06 | ssVNKMNRLWEPLsr | 43 |

Example 6

Peptides that Bind to Teflon

Selection of Teflon (GoreTex®; polytetrafuorethylene (PTFE))-binding peptides was performed as described above for the titanium-binding peptides except that sections of GoreTex fabric were used instead of titanium beads. The Teflon-binding peptides that were isolated are shown in Table 9. In some embodiments, an exemplary binding module of the invention comprises only that portion of the sequence shown in uppercase letters.

TABLE 9

Teflon Binding Peptides

| Clone Number | Peptide Sequence | SEQ. ID. NO.: |
|---|---|---|
| AP16-01 | ssCWSRFRLFMLFCMFYLVSsr | 95 |
| AP16-02 | srCIKYPFLYCCLLSLFLFSsr | 96 |

Example 7

Isolation of Peptides that Specifically Bind to BMPRI and/or BMPRII

Identification of peptides that bind to BMPRI and/or BMPRII: In order to identify peptides that specifically bind to Bone Morphogenic Protein Receptor I (BMPRIA) and/or Bone Morphogenic Protein Receptor II ("BMPRII"), phage display libraries are screened to identify phage encoding peptides that bind to the extracellular domains of each receptor. The extracellular domains of these receptors are known in the art (Rosenweig et al. (1995) *Proc. Nat'l. Acad. Sci. USA* 92: 7632-7636; Ten Dijke et al. (1994) *J. Biol. Chem.* 269: 16985-16988). Various phage libraries are screened. Where appropriate, a phage library can be selected that is designed around a specific amino acid motif or that was made with a particular amino acid bias. BMPRIA and BMPRII (R&D Systems, Cat. Nos. 315-BR/CF and 811-BR) are dissolved in carbonate coating buffer (100 mM NaHCO$_3$, pH 9.6); 100 µl of this solution is added to the wells of a 96-well Immulon®-4 microtiter plate (Dynex Technologies, Chantilly, Va.). The plate is incubated overnight at 4° C. and then the nonspecific binding sites on the surface of the polystyrene are blocked with 1% Bovine Serum Albumin (BSA) in carbonate coating buffer. The plate is then incubated for an hour at room temperature with shaking at 50 rpm. The wells are then washed 5 times with 300 µl of PBS-T (Sigma Chemical Co., St. Louis, Mo., Cat. # P-3563). Each library is diluted in PBS-T and added at a concentration of 1010 pfu/ml in a total volume of 100 ul. The plates are then incubated at room temperature with shaking at 50 rpm for 3 hours; unbound phage is then removed with 5 washes of PBS-T. Bound phage are recovered by denaturation with 0.1 M glycine buffer pH 2.2 (see *Phage Display of Peptides and Proteins: A Laboratory Manual*, 1996, eds. Kay et al. (Academic Press, San Diego, Calif.)). Eluted phage are neutralized with phosphate buffer and then added to *E. coli* DH5α cells in 2×YT media. This mixture is incubated overnight at 37° C. in a shaker at 210 rpm. Phage supernatant is harvested by centrifuging at 8500×g for 10 minutes. Second and third rounds of selection are performed similarly to the first round of selection using the phage from the previous round of selection as the input phage. Phage display techniques are well known in the art, for example, as described in Sparks et al. (1996) "Screening phage-displayed random peptide libraries," pp. 227-253 in *Phage Display of Peptides and Proteins: A Laboratory Manual*, eds. Kay et al. (Academic Press, San Diego, Calif.).

To identify phage that specifically bind to BMPRIA or BMPRII, conventional ELISAs are performed using an anti-M13 phage antibody conjugated to horseradish peroxidase (HRP), followed by the addition of chromogenic agent ABTS (Sigma Chemical Co., St. Louis, Mo., Cat. # A3219). Relative binding strengths of the phage are determined by testing serial dilutions of the phage for binding to BMP receptors in an ELISA. The DNA encoding each selected peptide is isolated and sequenced to determine the amino acid sequence of the selected peptide.

These peptides are then linked together to create an analyte module that will bind to each of BMPRI and BMPRII, forming a heterodimer of these two receptors so as to induce signaling. Candidate peptides are synthesized and biotinylated and their binding to the BMP receptors confirmed. Briefly, the biotinylated peptides are synthesized with a linker between the BMP receptor binding sequence and the attached biotin moiety. This linker has the amino acid sequence GSSGK, which serves to separate the biotin moiety from the receptor binding portion of the peptide and which is flexible. Peptides are synthesized using solid-phase peptide synthetic techniques on a Rainin Symphony Peptide Synthesizer (Rainin Instrument Co., Emeryville, Calif.) using standard Fmoc chemistry. N-α-Fmoc-amino acids (with orthogonal side chain protecting groups) can be purchased from Novabiochem (Calbiochem-Novabiochem, Laufelfingen, Switzerland). After all residues are coupled, simultaneous cleavage and side chain deprotection will be achieved by treatment of a trifluoroacetic acid (TFA) cocktail. Crude peptide is precipitated with cold diethyl ether and purified by high-performance liquid chromatography on a Shimadzu Analytical/Semi-preparative HPLC unit on a Vydac C18 silica column (preparative 10 µm, 250 mm×22 mm; Grace Vydac Co., Hesperia, Calif.) using a linear gradient of water/acetonitrile containing 0.1% TFA. Homogeneity of the synthetic peptides is evaluated by analytical RP-HPLC (Vydac C18 silica column, 10 µm, 250 mm×4.6 mm) and the identity of the peptides is confirmed with MALDI-TOF-MS, for example, as performed commercially at the UNC-CH Proteomics Core Facility.

Generation of peptides that bind to BMPRI and/or BMPRII with high affinity: Peptides that are initially identified as binding to BMPRI and/or BMPRII may have low binding affinities, e.g., in the mid- to low-µM range, whereas it may be preferable that peptides for use in an IFBM have higher binding affinities, e.g., in the nM range. To identify such peptides, libraries of variants of the initially identified peptides are constructed and screened by affinity selection against BMPRI and/or BMPRII.

Determination of binding affinity is evaluated using procedures known in the art. For example, BMPRI, BMPRII, and appropriate control proteins are dissolved in carbonate coating buffer (100 mM $NaHCO_3$, pH 9.6) and added to the wells of a 96-well polypropylene plate. After incubation overnight at 4° C., the wells are blocked with 1% BSA in PBS-T. Each receptor and control is tested for binding over a range of peptide concentrations from 0 to 200 µM in sterile PBS (pH 7.2). The wells are then washed to remove unbound peptide and a streptavidin-alkaline phosphatase conjugate solution (SA-AP) from USB (United States Biochemical # 11687) is added to each well to quantify the amount of bound peptide. Streptavidin-alkaline phosphatase activity is measured using the chromogenic reagent p-nitrophenyl phosphate reagent (Sigma-Aldrich, Inc., SigmaFast tablets, catalog #N1891) and measuring absorbance at 405 nm. To determine a binding curve and rough $K_D$, absorbance is plotted as a function of the concentration for each peptide. The impact of other factors on binding can be assessed, such as for example, pH, temperature, salt concentration, buffer components, and incubation time.

To create and identify peptides that bind to BMPRI and/or BMPRII with higher affinity, phage libraries are created based on an amino acid motif identified among the initial peptides isolated as binding to BMPRI and/or BMPRII and screened further for peptides with improved binding properties. Such techniques are known in the art (see, for example, Hyde-DeRuyscher et al. (2000) *Chem Biol.* 7: 17-25; Dalby et al. (2000) *Protein Sci.* 9: 2366-2376).

Characterization of agonist activity of hybrid peptides comprising BMPRI-binding peptides and BMPRII-binding peptides: Synthetic peptides are chemically synthesized that comprise both a BMPRI-binding peptide and a BMPRII-binding peptide connected with a flexible linker (e.g., a linker having the sequence GSSGSSG). Alternatively, the two receptor-binding peptides may be linked through the α and ε amino groups of a lysine (e.g., as in Cwirla et al. (1997) *Science* 276: 1696-1699 or in Wrighton et al. (1997) *Nat. Biotechnol.* 15: 1261-1265). These peptides are about 40 amino acids in length and are readily synthesized and purified.

These peptides are then assayed for BMP activity such as, for example, the induction of alkaline phosphatase activity in mouse mesenchymal C3H10T1/2 cells as known in the art and described, for example, by Cheng et al. (2003) *J. Bone Joint Surg. Am.* 85-A: 1544-1552 and Ruppert et al. (1996) *Eur. J. Biochem.* 237: 295-302. Briefly, C3H10T1/2 cells are added to a 96-well plate ($3 \times 10^4$ cells per well in a volume of 2000 in Gibco® MEM/EBSS medium (Invitrogen Corp., Carlsbad, Calif., Cat #11095-080) with 10% FBS and appropriate antibiotics and antimycotics. Cells are permitted to adhere to the plate for at least 3 hours by incubating at 37° C. in a 5% $CO_2$ atmosphere. Media is then aseptically aspirated and BMP-2 or peptides are added at various concentrations in high-glucose Gibco® DMEM (Invitrogen Corp., Carlsbad, Calif., Cat. #11965-092) plus 2% FBS. Cells are incubated with the tested compounds for three days, at which time the media is aspirated and the cells are washed three times with 300 µl of PBS (Gibco® PBS, Cat. #14190-144, Invitrogen Corp., Carlsbad, Calif.). 100 µl of pNPP (p-Nitrophenyl Phosphate Sigma Fast Tablet Set Cat #N-1891) in $H_2O$ is added to each well and the color is allowed to develop for up to 18 hours at 37° C. before absorbance is read at 405 nm.

$EC_{50}$ values are then determined using methods known in the art. Typical $EC_{50}$ values for this assay for BMP-2 range between 1 µg/ml and 10 µg/ml (see, e.g., Wiemann et al. (2002) *J. Biomed. Mater. Res.* 62: 119-127). It is known in the art that BMP-2 isolated from different sources can show different levels of activity, and one of skill in the art can adjust procedures accordingly to take these differences into account to achieve the desired result. For example, it is known in the art that recombinant human BMP-2 ("rhBMP-2") prepared using CHO cells has activity which differs 5-10 fold from the activity of recombinant human BMP-2 prepared using *E. coli* (see, e.g., Zhao and Chen (2002), "Expression of rhBMP-2 in *Escherichia coli* and Its Activity in Inducing Bone Formation," in *Advances in Skeletal Reconstruction Using Bone Morphogenic Proteins*, ed. T. S. Lindholm).

Immobilization of hybrid peptides onto collagen: Hybrid peptides that show BMP activity are synthetically linked to a peptide that binds to collagen. Briefly, a peptide containing the collagen binding module and the BMPRI-binding module is synthesized with an orthogonal protecting group on an amino acid in the linker between the modules, such as Fmoc-Lys(Dde)-OH. The Dde protecting group on the ε amino group of the lysine side chain can be selectively removed and a BMPRII-binding peptide coupled to the ε amino group. Alternatively, a linear peptide can be synthesized that comprises the collagen-binding module, the BMPRI-binding module, and the BMPRII-binding module.

The collagen-bound hybrid peptide is then tested for its BMP activity, such as by assaying for the induction of alkaline phosphatase activity in mouse mesenchymal C3H10T1/2 cells while the hybrid peptide is bound to a collagen matrix. Briefly, 5-mm disks of collagen are washed with PBS and added to the cell-based BMP activity assay.

Example 8

Sterilization of Surfaces Coated with IFBMs

IFBM-coated surfaces were treated with electron-beam sterilization procedures and gamma sterilization procedures. The binding performance of the coated surfaces was assessed before and after the sterilization procedures. Assays were performed on polystyrene and titanium surfaces. For the polystyrene assay, a binding module ("AFF-0002-PS") was biotinylated and relative binding was assessed by exposing the binding module to streptavidin-conjugated alkaline phosphatase. The results showed that the amount of biotinylated peptide that was bound to the polystyrene surface was essentially identical before and after the sterilization procedures. Similar results were obtained for an assay of a binding module ("AFF-0006-Ti") on titanium; in this assay, the performance of the coated surface before sterilization was approximately equal to its performance after sterilization.

Example 9

Preliminary Toxicity Testing

A PEGylated polystyrene-binding peptide was coated onto various polystyrene surfaces and tested as follows for adverse effects including cytotoxicity, hemolysis, and coagulation. The procedures were performed in Albino Swiss Mice (*Mus musculus*). As further discussed below, none of the IFBMs tested showed any signs of toxicity.

To assay for acute systemic toxicity, polystyrene squares (each square 4×4 cm; a total of 60 $cm^2$) were incubated for 70-74 hours at 37° C. in 20 mL of one of two vehicles: 0.9% USP normal saline or cotton seed oil (National Formulary). Five mice were each injected systemically with either vehicle or vehicle-extract at a dose rate of 50 mL extract per kg body weight. Mice were observed for signs of toxicity immediately after injection and at 4, 24, 48, and 72 hours post-injection. None of the animals injected with the vehicle-extract showed a greater biological reaction than those that received vehicle alone.

Coated surfaces were assayed for partial thromboblastin time according to ISO procedure 10993-4 (International Organization for Standardization, Geneva, Switzerland). Briefly, fresh whole human blood was drawn into vacutainer tubes containing sodium citrate and were spun down to isolate plasma, which was stored on ice until use. Coated polystyrene squares (as described above) were then incubated in the plasma at a ratio of 4 $cm^2$ per 1 mL for 15 minutes at 37° C. in polypropylene tubes and agitated at 60 rpm. The plasma extract was then separated, placed on ice, and tested on a Cascade® M-4 manual hemostasis analyzer (Helena Laboratories, Beaumont, Tex.). Clotting time was not significantly different than that observed for pure plasma or the standard reference control.

Cytotoxicity was assayed in L-929 Mouse Fibroblast Cells as specified in ISO 10993-5. Briefly, 60.8 $cm^2$ of polystyrene-coated squares was extracted into 20.3 mL of Eagle's Minimum Essential Medium+5% FBS at 37° C. for 24 hours. Positive, negative and intermediate cell-line test dishes were incubated at 37° C. in a humidified 5% $CO_2$ atmosphere. Cultures were evaluated for cytotoxic effects by microscopic observation at 24, 48, and 72 hours. The positive control showed a strong cytotoxic reaction score of "4" while test cells maintained a healthy ("0" score) appearance across all time points (score of "0"). Intermediate control cells scored as "2" across all time points.

Hemolysis testing measures the ability of a material or material extract to cause red blood cells to rupture. The test performed was ASTM F-756 Direct Contact Method. Saline was used to extract leachable substances. Coated polystyrene surface was extracted and then added to citrated rabbit blood (3.2%, diluted with PBS to obtain a total blood hemoglobin concentration of 10 mg/ml). A score of 0.4% was observed which falls into the passing category of 0-2%. The negative control returned a score of 0.1% and the positive control returned a score of 12.2%.

That which is claimed:

1. A binding module comprising a polypeptide selected from the group consisting of SEQ ID NOs: 82-84, 86, 88-89, and 91-92, or a conservatively substituted variant thereof, wherein the binding module binds to a bone morphogenetic protein.

2. A binding module comprising a polypeptide that binds to bone morphogenetic protein-2, wherein the polypeptide comprises:
   (i) a sequence that is at least 70% identical to any one of the sequences set forth in SEQ ID NOs: 82-84, 86, 88-89, and 91-92;
   (ii) a sequence that is at least 75% identical to any one of the sequences set forth in SEQ ID NOs: 82-84, 86, 88-89, and 91-92;
   (iii) a sequence that is at least 80% identical to any one of the sequences set forth in SEQ ID NOs: 82-84, 86, 88-89, and 91-92;
   (iv) a sequence that is at least 85% identical to any one of the sequences set forth in SEQ ID NOs: 82-84, 86, 88-89, and 91-92;
   (v) a sequence that is at least 90% identical to any one of the sequences set forth in SEQ ID NOs: 82-84, 86, 88-89, and 91-92; or
   (vi) a sequence that is at least 95% identical to any one of the sequences set forth in SEQ ID NOs: 82-84, 86, 88-89, and 91-92.

3. The binding module of claim 1 or claim 2, wherein the bone morphogenetic protein is bone morphogenetic protein-2.

4. An isolated nucleic acid comprising a nucleotide sequence encoding an amino acid sequence selected from the group consisting of SEQ ID NOs: 82-84, 86, 88-89, and 91-92, or a conservatively substituted variant thereof.

* * * * *

SEQUENCE LISTING

<160> NUMBER OF SEQ ID NOS: 558

<210> SEQ ID NO 1
<211> LENGTH: 17
<212> TYPE: PRT
<213> ORGANISM: Artificial Sequence
<220> FEATURE:
<223> OTHER INFORMATION: isolated from phage display libraries

```
<400> SEQUENCE: 1

Ser Ser His Lys His Pro Val Thr Pro Arg Phe Phe Val Val Glu Ser
1               5                   10                  15

Arg

<210> SEQ ID NO 2
<211> LENGTH: 22
<212> TYPE: PRT
<213> ORGANISM: Artificial Sequence
<220> FEATURE:
<223> OTHER INFORMATION: isolated from phage display libraries

<400> SEQUENCE: 2

Ser Ser Cys Asn Cys Tyr Val Thr Pro Asn Leu Leu Lys His Lys Cys
1               5                   10                  15

Tyr Lys Ile Cys Ser Arg
            20

<210> SEQ ID NO 3
<211> LENGTH: 22
<212> TYPE: PRT
<213> ORGANISM: Artificial Sequence
<220> FEATURE:
<223> OTHER INFORMATION: isolated from phage display libraries

<400> SEQUENCE: 3

Ser Ser Cys Ser His Asn His His Lys Leu Thr Ala Lys His Gln Val
1               5                   10                  15

Ala His Lys Cys Ser Arg
            20

<210> SEQ ID NO 4
<211> LENGTH: 22
<212> TYPE: PRT
<213> ORGANISM: Artificial Sequence
<220> FEATURE:
<223> OTHER INFORMATION: isolated from phage display libraries

<400> SEQUENCE: 4

Ser Ser Cys Asp Gln Asn Asp Ile Phe Tyr Thr Ser Lys Lys Ser His
1               5                   10                  15

Lys Ser His Cys Ser Arg
            20

<210> SEQ ID NO 5
<211> LENGTH: 22
<212> TYPE: PRT
<213> ORGANISM: Artificial Sequence
<220> FEATURE:
<223> OTHER INFORMATION: isolated from phage display libraries

<400> SEQUENCE: 5

Ser Ser Ser Ser Asp Val Tyr Leu Val Ser His Lys His His Leu Thr
1               5                   10                  15

Arg His Asn Ser Ser Arg
            20

<210> SEQ ID NO 6
<211> LENGTH: 22
<212> TYPE: PRT
<213> ORGANISM: Artificial Sequence
<220> FEATURE:
<223> OTHER INFORMATION: isolated from phage display libraries
```

```
<400> SEQUENCE: 6

Ser Ser Ser Asp Lys Cys His Lys His Trp Tyr Cys Tyr Glu Ser Lys
1               5                   10                  15

Tyr Gly Gly Ser Ser Arg
            20

<210> SEQ ID NO 7
<211> LENGTH: 14
<212> TYPE: PRT
<213> ORGANISM: Artificial Sequence
<220> FEATURE:
<223> OTHER INFORMATION: isolated from phage display libraries

<400> SEQUENCE: 7

His His Lys Leu Lys His Gln Met Leu His Leu Asn Gly Gly
1               5                   10

<210> SEQ ID NO 8
<211> LENGTH: 14
<212> TYPE: PRT
<213> ORGANISM: Artificial Sequence
<220> FEATURE:
<223> OTHER INFORMATION: isolated from phage display libraries

<400> SEQUENCE: 8

Gly His His His Lys Lys Asp Gln Leu Pro Gln Leu Gly Gly
1               5                   10

<210> SEQ ID NO 9
<211> LENGTH: 25
<212> TYPE: PRT
<213> ORGANISM: Artificial Sequence
<220> FEATURE:
<223> OTHER INFORMATION: isolated from phage display libraries

<400> SEQUENCE: 9

Ser Ser Ser Asp Lys Ser His Lys His Trp Tyr Ser Tyr Glu Ser Lys
1               5                   10                  15

Tyr Gly Gly Ser Gly Ser Ser Gly Lys
            20                  25

<210> SEQ ID NO 10
<211> LENGTH: 25
<212> TYPE: PRT
<213> ORGANISM: Artificial Sequence
<220> FEATURE:
<223> OTHER INFORMATION: isolated from phage display libraries

<400> SEQUENCE: 10

Ser Ser Ser Asp Lys Cys His Lys His Trp Tyr Cys Tyr Glu Ser Lys
1               5                   10                  15

Tyr Gly Gly Ser Gly Ser Ser Gly Lys
            20                  25

<210> SEQ ID NO 11
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 11

Ser Ser Asp Trp Gly Val Val Ala Ser Ala Trp Asp Ala Phe Glu Ala
1               5                   10                  15

Leu Asp Ala Ser Arg
```

```
<210> SEQ ID NO 12
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 12

Ser Ser Gly Ala Asp Phe Gly Tyr Gly Ser Trp Val Ser Phe Ser Ala
1               5                   10                  15

Leu Ser Ala Ser Arg
            20

<210> SEQ ID NO 13
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 13

Ser Arg Gly Glu Ala Ser Gly Trp Glu Ala Phe Ser Ala Leu Glu Ala
1               5                   10                  15

Ala Val Val Ser Arg
            20

<210> SEQ ID NO 14
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 14

Ser Arg Ser Ser Asp Ser Ala Phe Ser Ser Phe Ser Ala Leu Glu Gly
1               5                   10                  15

Ser Val Val Ser Arg
            20

<210> SEQ ID NO 15
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 15

Ser Arg Asp Gly Ala Gly Ala Ala Ala Trp Gly Ala Phe Ser Ala Leu
1               5                   10                  15

Ala Ser Glu Ser Arg
            20

<210> SEQ ID NO 16
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 16

Ser Arg Gly Gly Glu Ala Ala Ala Gly Ala Trp Val Ser Phe Ser Ala
1               5                   10                  15

Leu Glu Ser Ser Arg
```

```
<210> SEQ ID NO 17
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 17

Ser Arg Val Ser Gly Val Ala Ala Trp Glu Ala Phe Ala Gly Leu Ser
1               5                   10                  15

Val Ser Ser Ser Arg
            20

<210> SEQ ID NO 18
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 18

Ser Arg Asp Gly Gly Ser Phe Ser Ala Phe Ser Ser Leu Val Trp Ala
1               5                   10                  15

Ala Asp Ser Ser Arg
            20

<210> SEQ ID NO 19
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 19

Ser Ser Val Ala Gly Asp Val Gly Ser Ser Trp Ala Ala Phe Ala Ser
1               5                   10                  15

Leu Ala Ala Ser Arg
            20

<210> SEQ ID NO 20
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 20

Ser Ser Trp Glu Val Phe Ser Ser Leu Glu Ser Gly Ser Val Gly Ala
1               5                   10                  15

Gly Ala Gly Ser Arg
            20

<210> SEQ ID NO 21
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 21

Ser Ser Ser Ser Gly Ala Val Ser Ser Phe Glu Ser Leu Ser Gly Ser
1               5                   10                  15

Val Val Ser Ser Arg
```

-continued

```
            20

<210> SEQ ID NO 22
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 22

Ser Arg Glu Gly Val Ala Trp Glu Ala Phe Gly Ala Leu Ser Ser Phe
1               5                   10                  15

Ala Ala Asp Ser Arg
            20

<210> SEQ ID NO 23
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 23

Ser Ser Trp Gly Leu Ala Ser Glu Ala Ser Phe Phe Ser Phe Ser Ala
1               5                   10                  15

Leu Ser Ser Ser Arg
            20

<210> SEQ ID NO 24
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 24

Ser Arg Glu Gly Ala Ala Trp Asp Ser Phe Phe Ala Leu Ser Gly Gly
1               5                   10                  15

Ser Ala Ala Ser Arg
            20

<210> SEQ ID NO 25
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 25

Ser Ser Ser Val Asp Leu Tyr Phe Pro Leu Lys Gly Asp Val Val Ser
1               5                   10                  15

Arg

<210> SEQ ID NO 26
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 26

Ser Ser Phe Glu Pro Leu Arg Phe Pro Leu Lys Gly Val Pro Val Ser
1               5                   10                  15

Arg
```

```
<210> SEQ ID NO 27
<211> LENGTH: 7
<212> TYPE: PRT
<213> ORGANISM: Artificial Sequence
<220> FEATURE:
<223> OTHER INFORMATION: consensus sequence from comparing peptides
      isolated from phage display libraries
<221> NAME/KEY: VARIANT
<222> LOCATION: (1)...(1)
<223> OTHER INFORMATION: Xaa at this position can be Trp, Phe, or Tyr
<221> NAME/KEY: VARIANT
<222> LOCATION: (2)...(3)
<223> OTHER INFORMATION: Xaa can be any amino acid
<221> NAME/KEY: VARIANT
<222> LOCATION: (5)...(5)
<223> OTHER INFORMATION: Xaa can be any amino acid
<221> NAME/KEY: VARIANT
<222> LOCATION: (6)...(6)
<223> OTHER INFORMATION: Xaa at this position can be Ser, Thr, Ala, or
      Gly

<400> SEQUENCE: 27

Xaa Xaa Xaa Phe Xaa Xaa Leu
1               5

<210> SEQ ID NO 28
<211> LENGTH: 7
<212> TYPE: PRT
<213> ORGANISM: Artificial Sequence
<220> FEATURE:
<223> OTHER INFORMATION: consensus sequence from comparing peptides
      isolated from phage display libraries
<221> NAME/KEY: VARIANT
<222> LOCATION: (1)...(1)
<223> OTHER INFORMATION: Xaa at this position can be Leu or Val
<221> NAME/KEY: VARIANT
<222> LOCATION: (2)...(2)
<223> OTHER INFORMATION: Xaa can be any amino acid
<221> NAME/KEY: VARIANT
<222> LOCATION: (6)...(6)
<223> OTHER INFORMATION: Xaa at this position can be Lys or Arg

<400> SEQUENCE: 28

Xaa Xaa Phe Pro Leu Xaa Gly
1               5

<210> SEQ ID NO 29
<211> LENGTH: 39
<212> TYPE: PRT
<213> ORGANISM: Artificial Sequence
<220> FEATURE:
<223> OTHER INFORMATION: IFBM

<400> SEQUENCE: 29

Ser Ser Phe Glu Pro Leu Arg Phe Pro Leu Lys Gly Val Pro Val Ser
1               5                   10                  15

Arg Gly Ser Ser Gly Lys Asp Val Asn Ser Ile Trp Met Ser Arg Val
            20                  25                  30

Ile Glu Trp Thr Tyr Asp Ser
        35

<210> SEQ ID NO 30
<211> LENGTH: 39
<212> TYPE: PRT
<213> ORGANISM: Artificial Sequence
<220> FEATURE:
<223> OTHER INFORMATION: IFBM

<400> SEQUENCE: 30

Asp Val Asn Ser Ile Trp Met Ser Arg Val Ile Glu Trp Thr Tyr Asp
```

```
                1               5                   10                  15
Ser Gly Ser Ser Gly Lys Ser Ser Phe Glu Pro Leu Arg Phe Pro Leu
                    20                  25                  30

Lys Gly Val Pro Val Ser Arg
            35
```

<210> SEQ ID NO 31
<211> LENGTH: 43
<212> TYPE: PRT
<213> ORGANISM: Artificial Sequence
<220> FEATURE:
<223> OTHER INFORMATION: IFBM

<400> SEQUENCE: 31

```
Ser Arg Ser Ser Asp Ser Ala Phe Ser Ser Phe Ser Ala Leu Glu Gly
1               5                   10                  15

Ser Val Val Ser Arg Gly Ser Ser Gly Lys Asp Val Asn Ser Ile Trp
                    20                  25                  30

Met Ser Arg Val Ile Glu Trp Thr Tyr Asp Ser
                35                  40
```

<210> SEQ ID NO 32
<211> LENGTH: 43
<212> TYPE: PRT
<213> ORGANISM: Artificial Sequence
<220> FEATURE:
<223> OTHER INFORMATION: IFBM

<400> SEQUENCE: 32

```
Asp Val Asn Ser Ile Trp Met Ser Arg Val Ile Glu Trp Thr Tyr Asp
1               5                   10                  15

Ser Gly Ser Ser Gly Lys Ser Arg Ser Ser Asp Ser Ala Phe Ser Ser
                    20                  25                  30

Phe Ser Ala Leu Glu Gly Ser Val Val Ser Arg
                35                  40
```

<210> SEQ ID NO 33
<211> LENGTH: 39
<212> TYPE: PRT
<213> ORGANISM: Artificial Sequence
<220> FEATURE:
<223> OTHER INFORMATION: IFBM

<400> SEQUENCE: 33

```
Ser Ser Ser Val Asp Leu Tyr Phe Pro Leu Lys Gly Asp Val Val Ser
1               5                   10                  15

Arg Gly Ser Ser Gly Lys Asp Val Asn Ser Ile Trp Met Ser Arg Val
                    20                  25                  30

Ile Glu Trp Thr Tyr Asp Ser
                35
```

<210> SEQ ID NO 34
<211> LENGTH: 39
<212> TYPE: PRT
<213> ORGANISM: Artificial Sequence
<220> FEATURE:
<223> OTHER INFORMATION: IFBM

<400> SEQUENCE: 34

```
Asp Val Asn Ser Ile Trp Met Ser Arg Val Ile Glu Trp Thr Tyr Asp
1               5                   10                  15

Ser Gly Ser Ser Gly Lys Ser Ser Ser Val Asp Leu Tyr Phe Pro Leu
                    20                  25                  30
```

```
Lys Gly Asp Val Val Ser Arg
        35
```

<210> SEQ ID NO 35
<211> LENGTH: 43
<212> TYPE: PRT
<213> ORGANISM: Artificial Sequence
<220> FEATURE:
<223> OTHER INFORMATION: IFBM

<400> SEQUENCE: 35

```
Ser Arg Gly Gly Glu Ala Ala Gly Ala Trp Val Ser Phe Ser Ala
1               5                   10                  15

Leu Glu Ser Ser Arg Gly Ser Ser Gly Lys Asp Val Asn Ser Ile Trp
                20                  25                  30

Met Ser Arg Val Ile Glu Trp Thr Tyr Asp Ser
        35                  40
```

<210> SEQ ID NO 36
<211> LENGTH: 43
<212> TYPE: PRT
<213> ORGANISM: Artificial Sequence
<220> FEATURE:
<223> OTHER INFORMATION: IFBM

<400> SEQUENCE: 36

```
Asp Val Asn Ser Ile Trp Met Ser Arg Val Ile Glu Trp Thr Tyr Asp
1               5                   10                  15

Ser Gly Ser Ser Gly Lys Ser Arg Gly Gly Glu Ala Ala Ala Gly Ala
                20                  25                  30

Trp Val Ser Phe Ser Ala Leu Glu Ser Ser Arg
        35                  40
```

<210> SEQ ID NO 37
<211> LENGTH: 43
<212> TYPE: PRT
<213> ORGANISM: Artificial Sequence
<220> FEATURE:
<223> OTHER INFORMATION: IFBM

<400> SEQUENCE: 37

```
Ser Ser Asp Trp Gly Val Val Ser Ala Trp Asp Ala Phe Glu Ala
1               5                   10                  15

Leu Asp Ala Ser Arg Gly Ser Ser Gly Lys Asp Val Asn Ser Ile Trp
                20                  25                  30

Met Ser Arg Val Ile Glu Trp Thr Tyr Asp Ser
        35                  40
```

<210> SEQ ID NO 38
<211> LENGTH: 43
<212> TYPE: PRT
<213> ORGANISM: Artificial Sequence
<220> FEATURE:
<223> OTHER INFORMATION: IFBM

<400> SEQUENCE: 38

```
Asp Val Asn Ser Ile Trp Met Ser Arg Val Ile Glu Trp Thr Tyr Asp
1               5                   10                  15

Ser Gly Ser Ser Gly Lys Ser Ser Asp Trp Gly Val Val Ala Ser Ala
                20                  25                  30

Trp Asp Ala Phe Glu Ala Leu Asp Ala Ser Arg
        35                  40
```

```
<210> SEQ ID NO 39
<211> LENGTH: 23
<212> TYPE: PRT
<213> ORGANISM: Artificial Sequence
<220> FEATURE:
<223> OTHER INFORMATION: isolated from phage display libraries

<400> SEQUENCE: 39

Ser Ser Ser Ser Tyr Phe Asn Leu Gly Leu Val Lys His Asn His Val
1               5                   10                  15

Arg His His Asp Ser Ser Arg
            20

<210> SEQ ID NO 40
<211> LENGTH: 22
<212> TYPE: PRT
<213> ORGANISM: Artificial Sequence
<220> FEATURE:
<223> OTHER INFORMATION: isolated from phage display libraries

<400> SEQUENCE: 40

Ser Ser Cys His Asp His Ser Asn Lys Tyr Leu Lys Ser Trp Lys His
1               5                   10                  15

Gln Gln Asn Cys Ser Arg
            20

<210> SEQ ID NO 41
<211> LENGTH: 23
<212> TYPE: PRT
<213> ORGANISM: Artificial Sequence
<220> FEATURE:
<223> OTHER INFORMATION: isolated from phage display libraries

<400> SEQUENCE: 41

Ser Ser Ser Cys Lys His Asp Ser Glu Phe Ile Lys Lys His Val His
1               5                   10                  15

Ala Val Lys Lys Cys Ser Arg
            20

<210> SEQ ID NO 42
<211> LENGTH: 23
<212> TYPE: PRT
<213> ORGANISM: Artificial Sequence
<220> FEATURE:
<223> OTHER INFORMATION: isolated from phage display libraries

<400> SEQUENCE: 42

Ser Ser Ser Cys His His Leu Lys His Asn Thr His Lys Glu Ser Lys
1               5                   10                  15

Met His His Glu Cys Ser Arg
            20

<210> SEQ ID NO 43
<211> LENGTH: 15
<212> TYPE: PRT
<213> ORGANISM: Artificial Sequence
<220> FEATURE:
<223> OTHER INFORMATION: isolated from phage display libraries

<400> SEQUENCE: 43

Ser Ser Val Asn Lys Met Asn Arg Leu Trp Glu Pro Leu Ser Arg
1               5                   10                  15

<210> SEQ ID NO 44
<211> LENGTH: 21
```

```
<212> TYPE: PRT
<213> ORGANISM: Artificial Sequence
<220> FEATURE:
<223> OTHER INFORMATION: isolated from phage display libraries

<400> SEQUENCE: 44

Ser Ser Ala Pro Leu Thr Glu Ser Glu Ala Trp Arg Gly Phe Ser Lys
1               5                   10                  15

Leu Glu Val Ser Arg
            20

<210> SEQ ID NO 45
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 45

Ser Ser Ser Met Pro Val Gly Trp Asp Ser Trp Arg Gly Leu Glu Trp
1               5                   10                  15

Ser Asp Arg Ser Arg
            20

<210> SEQ ID NO 46
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 46

Ser Ser Glu Gly Arg Gly Gly Trp Asn Ser Trp Glu Ala Phe Arg Glu
1               5                   10                  15

Leu Val Val Ser Arg
            20

<210> SEQ ID NO 47
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 47

Ser Ser Gly Gly Gly Gly Ala Trp Glu Ser Trp Arg Gly Leu Ser Gly
1               5                   10                  15

Val Glu Leu Ser Arg
            20

<210> SEQ ID NO 48
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 48

Ser Arg Asn Val Glu Gly Ser Trp Glu Ser Phe Ala Gly Leu Ser His
1               5                   10                  15

Val Arg Glu Ser Arg
            20

<210> SEQ ID NO 49
<211> LENGTH: 21
```

```
<212> TYPE: PRT
<213> ORGANISM: Artificial Sequence
<220> FEATURE:
<223> OTHER INFORMATION: isolated from phage display libraries

<400> SEQUENCE: 49

Ser Arg Glu Asp Gly Gly Arg Trp Glu Ser Phe Leu Gly Leu Ser Ala
1               5                   10                  15

Val Glu Val Ser Arg
            20

<210> SEQ ID NO 50
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 50

Ser Ser Val Glu Gly Ser Ala Trp Ser Ala Phe Lys Ser Leu Ser Ser
1               5                   10                  15

Glu Gly Val Ser Arg
            20

<210> SEQ ID NO 51
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 51

Ser Arg Val Glu Gly Gly Ala Trp Gln Ala Leu Ala Gly Leu Thr Val
1               5                   10                  15

Glu Arg Val Ser Arg
            20

<210> SEQ ID NO 52
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 52

Ser Ser Pro Pro Lys His Ala Trp Gly Ser Phe Asp Ala Leu Gly Gly
1               5                   10                  15

Gln Val Val Ser Arg
            20

<210> SEQ ID NO 53
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 53

Ser Ser Glu Arg Gly Val Gly Trp Glu Val Phe Leu Ala Met Glu Gly
1               5                   10                  15

Ala Arg Met Ser Arg
            20

<210> SEQ ID NO 54
<211> LENGTH: 21
```

```
<212> TYPE: PRT
<213> ORGANISM: Artificial Sequence
<220> FEATURE:
<223> OTHER INFORMATION: isolated from phage display libraries

<400> SEQUENCE: 54

Ser Ser Ser Ser Ser Gly Thr Trp Gln Ala Phe Thr Gly Leu Ser Gly
1               5                   10                  15

Glu Arg Val Ser Arg
            20

<210> SEQ ID NO 55
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 55

Ser Ser Ser Pro Gly Gly Gly Ser Gly Gly Trp Asp Ala Phe Tyr Ser
1               5                   10                  15

Leu Val Gly Ser Arg
            20

<210> SEQ ID NO 56
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 56

Ser Ser Gly Gly Gly Gly Gly Gly Glu Gly Phe Ser Ser Leu Ser Gly
1               5                   10                  15

Asn Gly Arg Ser Arg
            20

<210> SEQ ID NO 57
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 57

Ser Ser Thr Gly Gly Gly Ser Trp Glu Glu Phe Lys Ala Met Thr Pro
1               5                   10                  15

Ser Trp Thr Ser Arg
            20

<210> SEQ ID NO 58
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 58

Ser Ser Glu Gly Ser Gly Leu Trp Asp Ser Phe Ser Ser Leu Ser Val
1               5                   10                  15

His Glu Val Ser Arg
            20

<210> SEQ ID NO 59
<211> LENGTH: 21
```

```
<212> TYPE: PRT
<213> ORGANISM: Artificial Sequence
<220> FEATURE:
<223> OTHER INFORMATION: isolated from phage display libraries

<400> SEQUENCE: 59

Ser Ser Gly Val Thr Gln Glu Ser Ala Ser Trp Ser Ser Phe Arg Thr
1               5                   10                  15

Leu Ala Val Ser Arg
            20

<210> SEQ ID NO 60
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 60

Ser Ser Ser Lys Val Ala Pro Ser Gly Glu Trp Arg Ser Phe Ala Thr
1               5                   10                  15

Leu Glu Val Ser Arg
            20

<210> SEQ ID NO 61
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 61

Ser Ser Glu Ala Gly Arg Gly Trp Glu Gly Phe Lys Ala Leu Glu Gly
1               5                   10                  15

Tyr Gln Val Ser Arg
            20

<210> SEQ ID NO 62
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 62

Ser Ser Leu Gly Gln Thr Gly Trp Glu Ala Phe Glu Ser Leu Ser Gly
1               5                   10                  15

Thr Arg Gly Ser Arg
            20

<210> SEQ ID NO 63
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 63

Ser Ser Val Ala Trp Asp Ala Phe Thr Val Phe Glu Ser Leu Glu Gly
1               5                   10                  15

Val Ala Thr Ser Arg
            20

<210> SEQ ID NO 64
<211> LENGTH: 21
```

```
<212> TYPE: PRT
<213> ORGANISM: Artificial Sequence
<220> FEATURE:
<223> OTHER INFORMATION: isolated from phage display libraries

<400> SEQUENCE: 64

Ser Ser Glu Val Val Glu Pro Trp Glu Trp Trp Val Ala Leu Glu Arg
1               5                   10                  15

Ala Gly Gly Ser Arg
            20

<210> SEQ ID NO 65
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 65

Ser Arg Val Ala Ala Val Ser Trp Glu Phe Phe Gly Ser Leu Ser Ser
1               5                   10                  15

Ala Gly Val Ser Arg
            20

<210> SEQ ID NO 66
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 66

Ser Ser Ala Asp Leu Gly Val Ser Gly Ser Trp Glu Gly Phe Ala Leu
1               5                   10                  15

Met Arg Gly Ser Arg
            20

<210> SEQ ID NO 67
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 67

Ser Ser Val Gly Gln Met Gly Trp Glu Ala Phe Glu Ser Leu Ser Gly
1               5                   10                  15

Thr Gly Gly Ser Arg
            20

<210> SEQ ID NO 68
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 68

Ser Ser Gly Gln Gly Glu Thr Trp Glu Trp Phe Ala Gly Met Arg Gly
1               5                   10                  15

Ser Val Ala Ser Arg
            20

<210> SEQ ID NO 69
<211> LENGTH: 21
```

```
<212> TYPE: PRT
<213> ORGANISM: Artificial Sequence
<220> FEATURE:
<223> OTHER INFORMATION: isolated from phage display libraries

<400> SEQUENCE: 69

Ser Ser Tyr Phe Asp Val Phe Ser Ser Met Thr Gly Thr Arg Ala Ala
1               5                   10                  15

Gly Ser Trp Ser Arg
            20

<210> SEQ ID NO 70
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 70

Ser Ser Ala Tyr Ser Val Phe Ser Ser Leu Arg Ala Asp Asn Ser Gly
1               5                   10                  15

Gly Ala Val Ser Arg
            20

<210> SEQ ID NO 71
<211> LENGTH: 19
<212> TYPE: PRT
<213> ORGANISM: Artificial Sequence
<220> FEATURE:
<223> OTHER INFORMATION: isolated from phage display libraries

<400> SEQUENCE: 71

Ser Ser Gly Gly Ile Ala Ser Leu Lys Tyr Asp Val Val Lys Thr Trp
1               5                   10                  15

Glu Ser Arg

<210> SEQ ID NO 72
<211> LENGTH: 16
<212> TYPE: PRT
<213> ORGANISM: Artificial Sequence
<220> FEATURE:
<223> OTHER INFORMATION: consensus sequence from comparing peptides
      isolated from phage display libraries

<400> SEQUENCE: 72

Gly Gly Gly Ala Trp Glu Ala Phe Ser Ser Leu Ser Gly Ser Arg Val
1               5                   10                  15

<210> SEQ ID NO 73
<211> LENGTH: 7
<212> TYPE: PRT
<213> ORGANISM: Artificial Sequence
<220> FEATURE:
<223> OTHER INFORMATION: consensus sequence from comparing peptides
      isolated from phage display libraries
<221> NAME/KEY: VARIANT
<222> LOCATION: (2)...(3)
<223> OTHER INFORMATION: Xaa can be any amino acid
<221> NAME/KEY: VARIANT
<222> LOCATION: (5)...(6)
<223> OTHER INFORMATION: Xaa can be any amino acid

<400> SEQUENCE: 73

Trp Xaa Xaa Phe Xaa Xaa Leu
1               5

<210> SEQ ID NO 74
```

```
<211> LENGTH: 15
<212> TYPE: PRT
<213> ORGANISM: Artificial Sequence
<220> FEATURE:
<223> OTHER INFORMATION: consensus sequence from comparing peptides
      isolated from phage display libraries

<400> SEQUENCE: 74

Ser Ser Gly Ala Trp Glu Ser Phe Ser Ser Leu Ser Gly Ser Ser
1               5                   10                  15

<210> SEQ ID NO 75
<211> LENGTH: 40
<212> TYPE: DNA
<213> ORGANISM: Artificial Sequence
<220> FEATURE:
<223> OTHER INFORMATION: encoding consensus sequence

<400> SEQUENCE: 75
tcgagtggtg cttgggagtc tttttcgtca ctgagtggat                      40

<210> SEQ ID NO 76
<211> LENGTH: 40
<212> TYPE: DNA
<213> ORGANISM: Artificial Sequence
<220> FEATURE:
<223> OTHER INFORMATION: partial complement of SEQ ID NO:75

<400> SEQUENCE: 76
caccacgaac cctcagaaaa agcagtgact cacctagatc                      40

<210> SEQ ID NO 77
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 77

Ser Ser Glu Gly Val Gly Gly Phe Pro Leu Lys Gly Ile Pro Gln Glu
1               5                   10                  15

Ala Trp Ala Ser Arg
            20

<210> SEQ ID NO 78
<211> LENGTH: 21
<212> TYPE: PRT
<213> ORGANISM: Artificial Sequence
<220> FEATURE:
<223> OTHER INFORMATION: isolated from phage display libraries
<221> NAME/KEY: VARIANT
<222> LOCATION: (18)...(18)
<223> OTHER INFORMATION: Xaa can be any amino acid

<400> SEQUENCE: 78

Ser Ser Pro Ser Gly Val Val Phe Pro Leu Arg Gly Glu Leu Leu Gly
1               5                   10                  15

Val Xaa Lys Ser Arg
            20

<210> SEQ ID NO 79
<211> LENGTH: 21
<212> TYPE: PRT
<213> ORGANISM: Artificial Sequence
<220> FEATURE:
<223> OTHER INFORMATION: consensus sequence from comparing peptides
      isolated from phage display libraries
```

```
<400> SEQUENCE: 79

Ser Ser Gly Gly Phe Val Pro Phe Pro Leu Arg Gly Glu Val Trp Asp
1               5                   10                  15
Gly Val His Ser Arg
            20

<210> SEQ ID NO 80
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 80

Ser Ser Glu Gly Ser Leu Ser Phe Pro Leu Lys Gly Gln Val Tyr Ser
1               5                   10                  15
Gly Trp Gly Ser Arg
            20

<210> SEQ ID NO 81
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 81

Ser Ser Gly Lys Pro Leu Glu Phe Pro Leu Arg Gly Thr Leu Ala Glu
1               5                   10                  15
Trp Pro Val Ser Arg
            20

<210> SEQ ID NO 82
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 82

Ser Arg Gly Glu Ala Leu Gly Phe Pro Leu Thr Gly Gln Leu Met Glu
1               5                   10                  15
Ala Ala Glu Ser Arg
            20

<210> SEQ ID NO 83
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 83

Ser Ser Met Trp Asp Val Gly Phe Pro Leu Lys Gly Arg Trp Ile Asp
1               5                   10                  15
Gly Ala Asp Ser Arg
            20

<210> SEQ ID NO 84
<211> LENGTH: 21
<212> TYPE: PRT
<213> ORGANISM: Artificial Sequence
<220> FEATURE:
<223> OTHER INFORMATION: isolated from phage display libraries
```

```
<400> SEQUENCE: 84

Ser Ser Ser Asn Ser Leu Trp Phe Pro Leu Arg Gly Ser Thr Val Glu
1               5                   10                  15

Val Gly Ala Ser Arg
            20

<210> SEQ ID NO 85
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 85

Ser Ser Gly Pro Ala Leu Arg Leu Pro Leu Arg Gly Thr Val Val Ser
1               5                   10                  15

Asp Val Pro Ser Arg
            20

<210> SEQ ID NO 86
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 86

Ser Ser Ala Asp Arg Val Ala Trp Pro Leu Lys Gly Ala Pro Val Trp
1               5                   10                  15

Val Lys Glu Ser Arg
            20

<210> SEQ ID NO 87
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 87

Ser Ser Gly Leu Ala Leu Gly Leu Pro Ile Lys Gly Trp Thr Val Ser
1               5                   10                  15

Gly Lys Asp Ser Arg
            20

<210> SEQ ID NO 88
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 88

Ser Ser Gly Tyr Thr Leu Gly Phe Pro Leu Ser Gly Gln Thr Ile Lys
1               5                   10                  15

Asp Trp Pro Ser Arg
            20

<210> SEQ ID NO 89
<211> LENGTH: 21
<212> TYPE: PRT
<213> ORGANISM: Artificial Sequence
<220> FEATURE:
<223> OTHER INFORMATION: isolated from phage display libraries
```

```
<400> SEQUENCE: 89

Ser Ser Glu Gly Trp Val His Phe Pro Leu Lys Gly Asp Val Met Gly
1               5                   10                  15

Gly Pro Phe Ser Arg
            20

<210> SEQ ID NO 90
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 90

Ser Ser Gly Arg Tyr Val Ser Leu Pro Leu Lys Gly Glu Val Val Pro
1               5                   10                  15

Gln Thr Ala Ser Arg
            20

<210> SEQ ID NO 91
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 91

Ser Ser Glu Gly Gly Val Gly Phe Pro Leu Lys Gly Ile Pro Gln Glu
1               5                   10                  15

Ala Trp Ala Ser Arg
            20

<210> SEQ ID NO 92
<211> LENGTH: 21
<212> TYPE: PRT
<213> ORGANISM: Artificial Sequence
<220> FEATURE:
<223> OTHER INFORMATION: isolated from phage display libraries

<400> SEQUENCE: 92

Ser Arg Val Asp Ser Val Asn Phe Pro Leu Arg Gly Glu Thr Val Thr
1               5                   10                  15

Ser Met Val Ser Arg
            20

<210> SEQ ID NO 93
<211> LENGTH: 17
<212> TYPE: PRT
<213> ORGANISM: Artificial Sequence
<220> FEATURE:
<223> OTHER INFORMATION: consensus sequence from comparing peptides
      isolated from phage display libraries

<400> SEQUENCE: 93

Gly Gly Ala Leu Gly Phe Pro Leu Lys Gly Glu Val Val Glu Gly Trp
1               5                   10                  15

Ala

<210> SEQ ID NO 94
<211> LENGTH: 7
<212> TYPE: PRT
<213> ORGANISM: Artificial Sequence
<220> FEATURE:
<223> OTHER INFORMATION: consensus sequence from comparing peptides
      isolated from phage display libraries
```

```
<221> NAME/KEY: VARIANT
<222> LOCATION: (2)...(2)
<223> OTHER INFORMATION: Xaa can be any amino acid

<400> SEQUENCE: 94

Leu Xaa Phe Pro Leu Lys Gly
1               5

<210> SEQ ID NO 95
<211> LENGTH: 22
<212> TYPE: PRT
<213> ORGANISM: Artificial Sequence
<220> FEATURE:
<223> OTHER INFORMATION: isolated from phage display libraries

<400> SEQUENCE: 95

Ser Ser Cys Trp Ser Arg Phe Arg Leu Phe Met Leu Phe Cys Met Phe
1               5                  10                  15

Tyr Leu Val Ser Ser Arg
            20

<210> SEQ ID NO 96
<211> LENGTH: 22
<212> TYPE: PRT
<213> ORGANISM: Artificial Sequence
<220> FEATURE:
<223> OTHER INFORMATION: isolated from phage display libraries

<400> SEQUENCE: 96

Ser Arg Cys Ile Lys Tyr Pro Phe Leu Tyr Cys Cys Leu Leu Ser Leu
1               5                  10                  15

Phe Leu Phe Ser Ser Arg
            20

<210> SEQ ID NO 97
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 97

Cys Ala Glu Lys Trp Trp Trp Trp Ile Gln Tyr Ala Trp Gly Gly Val
1               5                  10                  15

Leu Cys

<210> SEQ ID NO 98
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 98

Cys Asp Asp Ile Asp Tyr Ile Lys Glu Ala Pro Ile Asp Ala Met Met
1               5                  10                  15

Cys Cys

<210> SEQ ID NO 99
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 99
```

```
Cys Asp Phe Phe Asn Arg His Gly Tyr Asn Ser Gly Cys Glu His Ser
1               5                   10                  15

Val Cys

<210> SEQ ID NO 100
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 100

Cys Asp Phe His Ser Asn Lys Tyr Tyr Ile Asn Gln Ile Ala Gly Ser
1               5                   10                  15

Asp Cys

<210> SEQ ID NO 101
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 101

Cys Asp Asn Gly Leu Asp Asp Cys Phe Glu Pro Cys Tyr Trp Ile Gln
1               5                   10                  15

Leu Cys

<210> SEQ ID NO 102
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 102

Cys Phe Glu Ile Ser Ser Ser Ser Thr Pro Ile Glu Leu Trp Glu Ser
1               5                   10                  15

Val Cys

<210> SEQ ID NO 103
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 103

Cys Phe Glu Ser Asp Phe Pro Asn Val Arg His His Val Leu Lys Gln
1               5                   10                  15

Ser Cys

<210> SEQ ID NO 104
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 104

Cys Phe Phe Phe Arg Arg Gln Ile Glu Ile Tyr Tyr Ala Arg Phe Gly
1               5                   10                  15

Phe Cys
```

<210> SEQ ID NO 105
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 105

Cys Phe Leu Phe Phe Ser Met Cys Asn Met Ala Cys Thr Lys Ala Lys
1               5                   10                  15

Glu Cys

<210> SEQ ID NO 106
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 106

Cys Phe Tyr Gln Asn Val Ile Ser Ser Ser Phe Ala Gly Asn Pro Trp
1               5                   10                  15

Glu Cys

<210> SEQ ID NO 107
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 107

Cys Gly Asp His Met Thr Asp Lys Asn Met Pro Asn Ser Gly Ile Ser
1               5                   10                  15

Gly Cys

<210> SEQ ID NO 108
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 108

Cys His Arg Tyr Asp Arg Arg Trp Thr Met Tyr Thr Arg Ala Arg Leu
1               5                   10                  15

Arg Cys

<210> SEQ ID NO 109
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 109

Cys Ile Met Thr Ser Asp Met Val Asn Ala Ala Ile Trp Asn Glu Val
1               5                   10                  15

Gln Cys

<210> SEQ ID NO 110
<211> LENGTH: 18
<212> TYPE: PRT

```
<213> ORGANISM: Artificial Sequence
<220> FEATURE:
<223> OTHER INFORMATION: isolated from phage display libraries

<400> SEQUENCE: 110

Cys Leu Phe Phe Phe Ser Met Ile Met Asn Phe Asp Phe Pro Asn Phe
1               5                   10                  15

Glu Cys

<210> SEQ ID NO 111
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 111

Cys Leu Pro Pro Pro Tyr Glu Pro Lys Gln Leu Ala Glu Pro Cys Asp
1               5                   10                  15

Gly Cys

<210> SEQ ID NO 112
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 112

Cys Leu Pro Trp Tyr Tyr Tyr Tyr Lys Ala Gln Gln Leu Tyr Asp His
1               5                   10                  15

Tyr Cys

<210> SEQ ID NO 113
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 113

Cys Met Arg Arg Trp Asp Arg Trp Val Arg Trp Ala Trp Ser Arg Gln
1               5                   10                  15

Lys Cys

<210> SEQ ID NO 114
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 114

Cys Met Trp Trp Trp Gln Trp Gly Ser Tyr Ile Tyr Gly Glu Leu Trp
1               5                   10                  15

Ile Cys

<210> SEQ ID NO 115
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 115
```

Cys Asn Glu Asp Val Asn Asn Phe Pro Pro Arg Met Asn Thr Glu Leu
1               5                   10                  15

Gly Cys

<210> SEQ ID NO 116
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 116

Cys Asn Met Leu Leu Asn Ser Leu Pro Leu Pro Ser Glu Asp Trp Ser
1               5                   10                  15

Ala Cys

<210> SEQ ID NO 117
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 117

Cys Asn Asn Asn His Arg Asp Val Asn Trp Asn Leu Arg Asp Asn Thr
1               5                   10                  15

Ala Cys

<210> SEQ ID NO 118
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 118

Cys Asn Asn Asn Val Asn Trp Tyr His Tyr Met Phe Ile Pro Trp Ala
1               5                   10                  15

Lys Cys

<210> SEQ ID NO 119
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 119

Cys Asn Asn Val Asn Ala Cys Gln Asn His Glu Asn Asn Met His Asn
1               5                   10                  15

Asp Cys

<210> SEQ ID NO 120
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 120

Cys Asn Pro Gly Tyr Asn Asn Met Met Asn Asp Ser Met Val Met Trp
1               5                   10                  15

Arg Cys

<210> SEQ ID NO 121
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 121

Cys Pro Phe Thr His Ser Leu Ala Leu Asn Thr Asp Arg Ala Ser Pro
1               5                   10                  15

Gly Cys

<210> SEQ ID NO 122
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 122

Cys Pro His Trp Pro Pro Pro Trp Cys Glu Trp Tyr Pro Glu Asn Trp
1               5                   10                  15

Cys Cys

<210> SEQ ID NO 123
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 123

Cys Pro Asn Pro Phe Pro Glu Pro Leu Asn His Asp Ala Ile Asp Trp
1               5                   10                  15

Cys Cys

<210> SEQ ID NO 124
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 124

Cys Pro Asn Val Pro Arg Pro Ala Gln Leu Ser Ile Cys Gly Asn Leu
1               5                   10                  15

Pro Cys

<210> SEQ ID NO 125
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 125

Cys Pro Pro Met Tyr Pro Gln Trp Glu Gly Asp Pro Asn Gln Arg Tyr
1               5                   10                  15

Asp Cys

<210> SEQ ID NO 126
<211> LENGTH: 18
<212> TYPE: PRT

<213> ORGANISM: Artificial Sequence
<220> FEATURE:
<223> OTHER INFORMATION: isolated from phage display libraries

<400> SEQUENCE: 126

Cys Pro Pro Pro Gly Gln Val Pro Pro Trp Pro Pro Ser Pro Pro Pro
1               5                   10                  15

Pro Cys

<210> SEQ ID NO 127
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 127

Cys Pro Arg Arg His Lys Arg Tyr Asn Trp Phe Ala His Asn Ala Arg
1               5                   10                  15

Met Cys

<210> SEQ ID NO 128
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 128

Cys Arg Gln Tyr Arg Phe Arg Pro Ile Val Arg Ala Arg Arg Leu Asn
1               5                   10                  15

Lys Cys

<210> SEQ ID NO 129
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 129

Cys Arg Arg Phe Arg Ser Arg Cys Pro Gly Glu Trp Arg Ser Trp Thr
1               5                   10                  15

Thr Cys

<210> SEQ ID NO 130
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 130

Cys Arg Val Gly Val Arg Arg Lys Glu Gly Gly Phe Arg Pro Trp Tyr
1               5                   10                  15

Lys Cys

<210> SEQ ID NO 131
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 131

```
Cys Arg Val Arg Arg Glu Pro Arg Met Arg Lys Ile Lys Lys Met Ala
1               5                   10                  15

Leu Cys

<210> SEQ ID NO 132
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 132

Cys Arg Tyr Ser Thr Ser Ser Trp Ser Asp Met Thr Cys Gly Cys Gly
1               5                   10                  15

Gln Cys

<210> SEQ ID NO 133
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 133

Cys Ser Gly Trp Lys Trp Trp Val Phe His Val Cys Trp Lys Gln Val
1               5                   10                  15

His Cys

<210> SEQ ID NO 134
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 134

Cys Ser Asn Ser Ser Cys Thr Ser His Thr Leu Tyr Ser Ser Val Met
1               5                   10                  15

Gly Cys

<210> SEQ ID NO 135
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 135

Cys Ser Ser Phe Met Ser Met His His Trp His Val Val Val Asp Ser
1               5                   10                  15

Cys Cys

<210> SEQ ID NO 136
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 136

Cys Ser Ser Ile Asn Ser Ser Tyr Val His Cys Leu Gly Cys Thr Glu
1               5                   10                  15

Ser Cys
```

<210> SEQ ID NO 137
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 137

Cys Ser Ser Arg Tyr Ser Thr Ala Tyr His Met Ala Ser Asn Ser Ile
1               5                   10                  15

Phe Cys

<210> SEQ ID NO 138
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 138

Cys Thr Glu Arg Arg Arg Arg Phe Asn Arg Asn Arg Pro Ala Lys Met
1               5                   10                  15

Arg Cys

<210> SEQ ID NO 139
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 139

Cys Thr Pro Arg Pro Pro Val Pro Val Tyr Ile Pro Tyr Ser Ser Ser
1               5                   10                  15

Pro Cys

<210> SEQ ID NO 140
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 140

Cys Val Asp Phe Lys Ser Lys Glu Lys Thr Glu Ile Met Leu Arg His
1               5                   10                  15

Ala Cys

<210> SEQ ID NO 141
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 141

Cys Val Phe Asp Ser Lys His Phe Ser Pro Thr His Ser Pro His Asp
1               5                   10                  15

Val Cys

<210> SEQ ID NO 142
<211> LENGTH: 18
<212> TYPE: PRT

```
<213> ORGANISM: Artificial Sequence
<220> FEATURE:
<223> OTHER INFORMATION: isolated from phage display libraries

<400> SEQUENCE: 142

Cys Val Tyr Lys Ile Tyr Tyr Leu Tyr Cys His Pro Tyr Leu Thr Phe
1               5                   10                  15

Pro Cys

<210> SEQ ID NO 143
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 143

Cys Trp Lys Ser Ser Ser Ser Met Met Thr Ile Val Trp Trp Asn Lys
1               5                   10                  15

Met Cys

<210> SEQ ID NO 144
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 144

Cys Trp Met Trp Trp Pro Glu Trp Trp Trp Gln Cys Ala Val Gln Cys
1               5                   10                  15

Asn Cys

<210> SEQ ID NO 145
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 145

Cys Trp Tyr Thr Trp Trp Cys Gln Ala Ser Thr Met Gly Gln Ile Tyr
1               5                   10                  15

Glu Cys

<210> SEQ ID NO 146
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 146

Cys Tyr Tyr Asp Ser Tyr Pro Ser Val Pro Tyr Tyr Gln Asn Pro
1               5                   10                  15

Ser Cys

<210> SEQ ID NO 147
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 147
```

Cys Tyr Tyr Phe Tyr Gln Ala Leu Gln Gly Leu Ile Lys Asn His Trp
1               5                   10                  15

Ala Cys

<210> SEQ ID NO 148
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 148

Cys Tyr Tyr Lys Pro Tyr Tyr Pro Cys Ser Ala Tyr Met Asn Phe Pro
1               5                   10                  15

Leu Cys

<210> SEQ ID NO 149
<211> LENGTH: 18
<212> TYPE: PRT
<213> ORGANISM: Artificial Sequence
<220> FEATURE:
<223> OTHER INFORMATION: isolated from phage display libraries

<400> SEQUENCE: 149

Cys Tyr Tyr Asn Gly Leu Val Val His His Ser Asn Ser Gly His Lys
1               5                   10                  15

Asp Cys

<210> SEQ ID NO 150
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 150

Cys Ala Asn Phe Leu Ser Phe Val Asn Asn Ser Tyr Cys Ile Asp Ser
1               5                   10                  15

Asn

<210> SEQ ID NO 151
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 151

Cys Ala Arg Arg Arg His His His His Pro Pro Met Pro His Phe Arg
1               5                   10                  15

Arg

<210> SEQ ID NO 152
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 152

Cys Cys Asp Gly Leu Ile Thr Ser Ser Trp Leu Asn Trp Phe Ala Arg
1               5                   10                  15

Gly

<210> SEQ ID NO 153
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 153

Cys Cys Glu Trp Trp Trp Cys Trp Lys Trp Trp Gln Cys Leu Trp Trp
1               5                   10                  15

Cys

<210> SEQ ID NO 154
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 154

Cys Cys Phe Asn Phe Phe Thr Ser Phe Asn Gln Gly Lys Asp Asn Phe
1               5                   10                  15

Val

<210> SEQ ID NO 155
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 155

Cys Cys Ser Ser Cys Glu Ser His Trp Lys Lys Phe Glu His Asn Arg
1               5                   10                  15

Gln

<210> SEQ ID NO 156
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 156

Cys Asp Asp Phe Val Leu Asp Tyr Asp Glu Tyr Met Val Met Asn
1               5                   10                  15

His

<210> SEQ ID NO 157
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 157

Cys Asp Asp Met Gly Asp Asp Val Lys Asp Pro Glu Asp Tyr Ile Asp
1               5                   10                  15

Gln

<210> SEQ ID NO 158
<211> LENGTH: 17
<212> TYPE: PRT

```
<213> ORGANISM: Artificial Sequence
<220> FEATURE:
<223> OTHER INFORMATION: isolated from phage display libraries

<400> SEQUENCE: 158

Cys Asp Phe Cys Phe Thr Asn Val Leu Phe Asp Ala Phe Gly Ser His
1               5                   10                  15

Val

<210> SEQ ID NO 159
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 159

Cys Asp Tyr Phe Ser Phe Leu Glu Cys Phe Ser Asn Gly Trp Ser Gly
1               5                   10                  15

Ala

<210> SEQ ID NO 160
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 160

Cys Phe Phe Phe Gly Gln Gly Asp Phe Met Cys Trp Ile Cys Leu Thr
1               5                   10                  15

Val

<210> SEQ ID NO 161
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 161

Cys Phe Phe Asn Ser Phe Asn Cys Thr Pro Asn Glu Met Trp Tyr Trp
1               5                   10                  15

Phe

<210> SEQ ID NO 162
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 162

Cys Phe Phe Ser Tyr Cys Phe Ser His Asp Val Ser Thr Tyr Asn Thr
1               5                   10                  15

Ala

<210> SEQ ID NO 163
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 163
```

Cys Phe Phe Ser Tyr Trp Asn Cys Leu Thr Asn Asn Ala Phe Val Lys
1               5                   10                  15

Pro

<210> SEQ ID NO 164
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 164

Cys Phe Gly Phe Ser Asp Cys Leu Ser Trp Phe Val Gln Pro Ser Thr
1               5                   10                  15

Ala

<210> SEQ ID NO 165
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 165

Cys Phe Gly Asn Phe Leu Ser Phe Gly Phe Asn Cys Glu Ser Ala Leu
1               5                   10                  15

Gly

<210> SEQ ID NO 166
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 166

Cys Phe Gly Asn Leu Gly Asn Leu Ile Tyr Thr Cys Asp Arg Leu Met
1               5                   10                  15

Pro

<210> SEQ ID NO 167
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 167

Cys Phe Gly Asn Val Phe Cys Val Tyr Asn Gln Phe Ala Ala Gly Leu
1               5                   10                  15

Phe

<210> SEQ ID NO 168
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 168

Cys Phe Thr Cys Phe Ser Phe Ala Phe Asn Phe Cys Phe Met Cys Trp
1               5                   10                  15

Met

```
<210> SEQ ID NO 169
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 169

Cys Phe Thr Phe Phe Lys Ala Ser Trp Ser Trp His His Ala Met
1               5                   10                  15

Met

<210> SEQ ID NO 170
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 170

Cys Phe Val His Asn Phe Phe Trp Phe Leu Gly Lys Asn Ser Asn Cys
1               5                   10                  15

Arg

<210> SEQ ID NO 171
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 171

Cys Phe Trp Tyr Ser Trp Leu Cys Ser Ala Ser Ser Ser Asp Ala Leu
1               5                   10                  15

Ile

<210> SEQ ID NO 172
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 172

Cys Gly Tyr Phe Cys Ser Phe Tyr Asn Tyr Leu Asp Ile Gly Thr Ala
1               5                   10                  15

Ser

<210> SEQ ID NO 173
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 173

Cys His Arg Cys Lys Arg Arg His Leu Leu Arg Arg Lys Gln Ala Asn
1               5                   10                  15

Arg

<210> SEQ ID NO 174
<211> LENGTH: 17
<212> TYPE: PRT
```

<213> ORGANISM: Artificial Sequence
<220> FEATURE:
<223> OTHER INFORMATION: isolated from phage display libraries

<400> SEQUENCE: 174

Cys Ile Phe Asn Ser Tyr Phe Cys Ser Phe Gln Leu Thr Ser Tyr Gly
1               5                   10                  15

Ser

<210> SEQ ID NO 175
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 175

Cys Lys Ala Phe Phe Phe Asn Phe Gln Cys Phe Val Phe Val Phe His
1               5                   10                  15

Phe

<210> SEQ ID NO 176
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 176

Cys Lys Phe Ser Phe Asp Phe Phe Ala Arg Phe Asn Arg His Phe Tyr
1               5                   10                  15

His

<210> SEQ ID NO 177
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 177

Cys Lys Ser Lys Lys Ser Ser His Ser Glu Ser Glu His Lys Lys Ser
1               5                   10                  15

Ser

<210> SEQ ID NO 178
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 178

Cys Leu Phe Asn Cys Ser Gly Glu Ser Trp Pro Met Ser Ile Val Pro
1               5                   10                  15

Ser

<210> SEQ ID NO 179
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 179

Cys Leu Lys Asp Tyr Tyr Tyr Ser Pro Cys Ser Tyr Ser Cys Asp Gln
1               5                   10                  15

His

<210> SEQ ID NO 180
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 180

Cys Leu Leu Lys Tyr Cys Tyr Ser Asp Leu Ala Ser Ser Ser Leu Ser
1               5                   10                  15

Ile

<210> SEQ ID NO 181
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 181

Cys Leu Val Phe Met Arg Pro Tyr Phe Leu Leu Val Phe Leu Met Cys
1               5                   10                  15

Trp

<210> SEQ ID NO 182
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 182

Cys Leu Tyr Cys His Leu Asn Asn Gln Phe Leu Ser Trp Val Ser Gly
1               5                   10                  15

Asn

<210> SEQ ID NO 183
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 183

Cys Leu Tyr Cys Leu Asn Tyr Ala Asn Phe Ser Asp Pro Met Thr Met
1               5                   10                  15

Phe

<210> SEQ ID NO 184
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 184

Cys Asn His Leu Gly Phe Phe Ser Ser Phe Cys Asp Arg Leu Val Glu
1               5                   10                  15

Asn

-continued

```
<210> SEQ ID NO 185
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 185

Cys Asn Ser Phe Met Phe Ile Asn Gly Ser Phe Lys Glu Thr Gly Gly
1               5                   10                  15

Cys

<210> SEQ ID NO 186
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 186

Cys Asn Ser Ser Ser Tyr Ser Trp Tyr Cys Trp Phe Gly Gly Ser Ser
1               5                   10                  15

Pro

<210> SEQ ID NO 187
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 187

Cys Arg Asp Arg Gln Arg Trp Val Arg Ile Phe Asn Arg Arg Cys Val
1               5                   10                  15

Thr

<210> SEQ ID NO 188
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 188

Cys Arg Met Lys Lys Arg Arg Arg Ala His Pro Pro Arg Asn Cys Met
1               5                   10                  15

Glu

<210> SEQ ID NO 189
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 189

Cys Arg Arg Met Arg Cys Arg Asp His Thr Gln Lys Trp Arg Arg Glu
1               5                   10                  15

Arg

<210> SEQ ID NO 190
<211> LENGTH: 17
<212> TYPE: PRT
```

```
<213> ORGANISM: Artificial Sequence
<220> FEATURE:
<223> OTHER INFORMATION: isolated from phage display libraries

<400> SEQUENCE: 190

Cys Arg Arg Arg Lys Asn Phe Gln Arg Cys Phe Arg Pro Leu Leu Tyr
1               5                   10                  15

Pro

<210> SEQ ID NO 191
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 191

Cys Arg Arg Arg Ser Gln Arg Asn Arg Arg Gly Asn Asp Asp Ser
1               5                   10                  15

Ala

<210> SEQ ID NO 192
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 192

Cys Ser Phe Phe Met Pro Trp Cys Asn Phe Leu Asn Gly Glu Met Ala
1               5                   10                  15

Val

<210> SEQ ID NO 193
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 193

Cys Ser Phe Ser Val Ser Lys Ser Ser Gln Ile Phe Ala Val Ser Tyr
1               5                   10                  15

Ser

<210> SEQ ID NO 194
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 194

Cys Ser Leu Thr Gly Cys Leu Tyr Asp Tyr Val Ser Phe Gly Trp Gly
1               5                   10                  15

Ala

<210> SEQ ID NO 195
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 195
```

```
Cys Ser Ser Ser Met Thr Tyr Arg Thr Ser Ser Ser Trp His Leu Lys
1               5                   10                  15
Ile

<210> SEQ ID NO 196
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 196

Cys Ser Thr Ser Tyr Ser Trp Asn Lys Trp Gln Ile Ser Ile Ser Ser
1               5                   10                  15
Tyr

<210> SEQ ID NO 197
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 197

Cys Thr Cys Phe Asn Leu Phe Asp Met Lys Thr Cys Pro Ser Phe Cys
1               5                   10                  15
Thr

<210> SEQ ID NO 198
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 198

Cys Thr Phe Gly Phe Pro Cys Val Met Ser Leu Val Asn His Val Pro
1               5                   10                  15
Ser

<210> SEQ ID NO 199
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 199

Cys Thr Asn Ser Asn Leu Asn Ser Ser Ser Trp His Thr Met Val Asp
1               5                   10                  15
Arg

<210> SEQ ID NO 200
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 200

Cys Thr Trp Trp Trp Trp Trp Val Val Asn Arg Glu Pro Tyr Val Ala
1               5                   10                  15
Cys
```

<210> SEQ ID NO 201
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 201

Cys Trp Asp Trp Met Thr Trp Gly Asn Asp Val Leu Val Asn Thr Asp
1               5                   10                  15

Trp

<210> SEQ ID NO 202
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 202

Cys Trp Leu Asp Asp Ser Asp Asp Tyr Asp Asp Asp Asp Met Met
1               5                   10                  15

Ala

<210> SEQ ID NO 203
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 203

Cys Trp Met Gly Leu Phe Glu Cys Pro Asp Ala Trp Leu His Asp Trp
1               5                   10                  15

Asp

<210> SEQ ID NO 204
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 204

Cys Trp Asn Ile Ser Cys Met Phe Gly Phe Gly Trp Gly Gly Gly Gly
1               5                   10                  15

Leu

<210> SEQ ID NO 205
<211> LENGTH: 17
<212> TYPE: PRT
<213> ORGANISM: Artificial Sequence
<220> FEATURE:
<223> OTHER INFORMATION: isolated from phage display libraries

<400> SEQUENCE: 205

Cys Tyr Ala Tyr Tyr Phe Phe Phe Tyr Ser Ser Gly Arg Gly Tyr His
1               5                   10                  15

Gln

<210> SEQ ID NO 206
<211> LENGTH: 17
<212> TYPE: PRT

<213> ORGANISM: Artificial Sequence
<220> FEATURE:
<223> OTHER INFORMATION: isolated from phage display libraries

<400> SEQUENCE: 206

Cys Tyr Phe Pro Phe Tyr Cys Tyr Asn Thr Ser Ser Leu Ser Leu Asp
1               5                   10                  15

Phe

<210> SEQ ID NO 207
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 207

Ala Asp Arg Val Trp Pro Arg His Thr Ser Ser Pro Tyr His Arg His
1               5                   10                  15

<210> SEQ ID NO 208
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 208

Ala Phe Ile Ser Asn Leu His Ala Ala Cys Ser Val Gly Ser Cys Lys
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 209

Cys His Thr Pro Trp Pro Pro Met Asn Arg Tyr Ala Ser Val Leu Ile
1               5                   10                  15

<210> SEQ ID NO 210
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 210

Cys Thr Arg Arg Arg Arg Phe Cys Val Ile Ile Phe Arg Arg Glu Met
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 211

Cys Thr Ser Ser Ser Gln Lys His Cys Tyr His Gly His Ser Ser Asp
1               5                   10                  15

<210> SEQ ID NO 212
<211> LENGTH: 16
<212> TYPE: PRT

```
<213> ORGANISM: Artificial Sequence
<220> FEATURE:
<223> OTHER INFORMATION: isolated from phage display libraries

<400> SEQUENCE: 212

Asp Cys Cys Cys Met Trp Asp Asp Gly Val Gly Asp Asp Val Asp Met
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 213

Asp Phe Cys Phe Met Met Met Asn Cys Thr Met Asn Ala His Tyr Phe
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 214

Asp Val Asn Ser Ile Trp Met Ser Arg Val Ile Glu Trp Thr Tyr Asp
1               5                   10                  15

<210> SEQ ID NO 215
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 215

Asp Trp Cys Asn Asn Ala Trp Asp Thr Tyr Ala Ile His Asn Asp Cys
1               5                   10                  15

<210> SEQ ID NO 216
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 216

Phe Leu Phe Phe Thr Asn Met Val Trp Tyr Phe Phe Ile Met Gly Ala
1               5                   10                  15

<210> SEQ ID NO 217
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 217

Phe Thr Val Ser Ser His Ile Ile Glu Trp Ser Ala Asp Ser Val Val
1               5                   10                  15

<210> SEQ ID NO 218
<211> LENGTH: 16
<212> TYPE: PRT
<213> ORGANISM: Artificial Sequence
<220> FEATURE:
```

```
<223> OTHER INFORMATION: isolated from phage display libraries

<400> SEQUENCE: 218

Gly Ala Gly Gly Phe Phe Leu Pro Cys Leu Trp Asn Pro Asp Arg Thr
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 219

Gly Lys Cys Val Phe Arg Arg Glu Asp Cys Phe Trp Tyr Tyr Met His
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 220

Gly Ser Ser Ser Cys Gln Gly Val Ser Gly Ser Asp Tyr Val Met Lys
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 221

His Ala Ser Ile His His Cys Ser Tyr Gln Gly Tyr Gly Gln Ser Gly
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 222

His Cys Asn Asn Glu Asn Arg Trp His His Asn Gly Ala Ile Gly Val
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 223

His Ile Ser Ser Cys Gln Met Val Gln Ser Trp Ser Arg Pro Ala His
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: isolated from phage display libraries
```

```
<400> SEQUENCE: 224

Ile Trp Glu Trp Phe Glu Leu Glu Met Leu Tyr Val Asn Arg Tyr Cys
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 225

Leu Ile His Arg Tyr Cys Arg Arg Val Pro Cys Arg Arg Glu Leu Lys
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 226

Met Ser Asn Phe Leu Ile Glu Phe Thr Tyr Asp Asn Val Gly Val Arg
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 227

Asn Phe Phe Val Glu Trp Ala Phe Asp Thr Gln Asp Arg Glu Glu Leu
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 228

Asn Gly Asn Glu Asn Asp Thr Ile Asn Asp Asn Asp Ile Asn Ala Ser
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 229

Asn Ile Asn Ile Val Glu Glu Arg Phe Met Val Glu Trp Asp Val Gln
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 230
```

```
Asn Pro Trp Ala Ser Ser Leu Val Ala Ala Cys Tyr Leu Asp Glu Ser
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 231

Asn Trp Trp Met Val Asn Leu Ile Pro Asp Glu Trp Cys Trp Asn Ser
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 232

Pro Phe Leu Phe Glu Ala Ser Asp Arg His Pro Ala Phe Asn His Met
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 233

Pro Gly Ser Ser Thr Phe Tyr Ser Ile Thr Met Thr Trp Asp Leu Pro
1               5                   10                  15

<210> SEQ ID NO 234
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 234

Pro Pro Ser Ser Asn Ser Asn Phe Met Leu Glu Phe Ser Trp Asp Ser
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 235

Pro Gln Ser Glu His Ser Lys Ser Tyr Met Ser Trp Ala Arg Ser Ser
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 236

Pro Ser Ala Cys Ser Arg Arg Ile Ile Gln Asp Thr Phe Phe Phe Met
1               5                   10                  15
```

```
<210> SEQ ID NO 237
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 237

Gln Glu Leu Arg Val Arg Lys Arg Arg Arg Pro Lys Asp His Glu Arg
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 238

Gln Glu Met Leu Asn Phe Phe Phe His Asn Gly Asn Phe Phe Phe Val
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 239

Gln His Arg Gln His His Asn Val Ile Tyr Ser Ala Val Cys Val Ala
1               5                   10                  15

<210> SEQ ID NO 240
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 240

Gln Met Asp Thr Ile Asp Asp Met Thr Trp Thr Gly Asp Asp Asp Cys
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 241

Arg Gly Pro Tyr Ile Trp Trp Leu Glu Glu Gln Ser Arg Thr Trp Glu
1               5                   10                  15

<210> SEQ ID NO 242
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 242

Arg Arg Arg Asn Lys Leu Ala Arg Thr Leu Val Tyr Arg Arg Arg Val
1               5                   10                  15
```

```
<210> SEQ ID NO 243
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 243

Arg Arg Arg Pro Lys Pro Gly Pro His Ile Ile Phe Thr Ala Ile Asn
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 244

Arg Arg Tyr Ala Thr Trp Ser Val Ala Ser Ile Gln Glu Cys Pro Arg
1               5                   10                  15

<210> SEQ ID NO 245
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 245

Arg Tyr Pro Tyr Asp Met Asp Trp Asp Trp His His Gln Glu Arg Asp
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 246

Ser Phe Phe Phe Trp Asp Thr Phe Gly Glu Ser Asn Lys Phe Phe Met
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 247

Ser Phe Met Phe Asn Asp Ser Ile Asp Asp Asp Asp Val Ser Glu
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 248

Ser Pro Gln Ala Arg Ser His Glu Asp Gln Val Met Gln Trp Trp Ile
1               5                   10                  15

<210> SEQ ID NO 249
<211> LENGTH: 16
```

```
<212> TYPE: PRT
<213> ORGANISM: Artificial Sequence
<220> FEATURE:
<223> OTHER INFORMATION: isolated from phage display libraries

<400> SEQUENCE: 249

Thr Phe Asp Asp Ala Met Leu Glu Trp Ser Leu Val Glu Trp Asp Ile
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 250

Thr Gly Gln Ser Ser Met Val Asn His Met Val Ser Glu Asn Gly Gly
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 251

Thr Met Gln Asp Phe Ser Ser Asp Glu Phe Tyr Thr Trp Thr Trp Asp
1               5                   10                  15

<210> SEQ ID NO 252
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 252

Val Phe Gly Phe Ser Cys Phe Glu Lys Asp Lys Arg Phe Asp Glu Leu
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 253

Val Leu Gly Trp Lys Ser Trp Lys Ile Tyr Trp Ala Trp Leu Val Glu
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 254

Trp Leu Trp Thr Trp Gln Glu Thr Ala Glu His Pro Ile Trp Asn Ser
1               5                   10                  15

<210> SEQ ID NO 255
<211> LENGTH: 16
<212> TYPE: PRT
<213> ORGANISM: Artificial Sequence
```

```
<220> FEATURE:
<223> OTHER INFORMATION: isolated from phage display libraries

<400> SEQUENCE: 255

Trp Met Trp Gln Ile Cys Pro Cys Met Met His Trp Val Leu Asn Trp
1               5                   10                  15

<210> SEQ ID NO 256
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 256

Trp Asn Cys Asp Tyr Glu Thr Gly Ala Gly Trp Arg Cys Ser Glu Ala
1               5                   10                  15

<210> SEQ ID NO 257
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 257

Trp Asn Phe Tyr Phe Val Ala Phe Ile Ala Leu Pro Met Glu Phe Val
1               5                   10                  15

<210> SEQ ID NO 258
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 258

Trp Trp Phe Arg Phe Lys Arg Arg Arg Trp Met Lys Ser Val Arg
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 259

Tyr Asp Met Met Met Asp Met Leu Lys Asn Asp Asp Lys Gly Phe Phe
1               5                   10                  15

<210> SEQ ID NO 260
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 260

Tyr Arg Met Ala Asp Arg Asp Val His Arg Trp Asp Lys Glu Tyr Glu
1               5                   10                  15

<210> SEQ ID NO 261
<211> LENGTH: 16
<212> TYPE: PRT
<213> ORGANISM: Artificial Sequence
<220> FEATURE:
<223> OTHER INFORMATION: isolated from phage display libraries
```

```
<400> SEQUENCE: 261

Tyr Arg Asn Met Glu Arg Ser Asn Met Ala Glu Thr Asn Ile Leu Ala
1               5                   10                  15

<210> SEQ ID NO 262
<211> LENGTH: 16
<212> TYPE: PRT
<213> ORGANISM: Artificial Sequence
<220> FEATURE:
<223> OTHER INFORMATION: isolated from phage display libraries

<400> SEQUENCE: 262

Tyr Tyr Phe Thr Glu Trp Ser Glu Asp Thr Ser Gly Gly Ser Ser Gly
1               5                   10                  15

<210> SEQ ID NO 263
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 263

Ala Lys Ile Leu Tyr Tyr Tyr Asp Met Gln Trp His Ile
1               5                   10

<210> SEQ ID NO 264
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 264

Ala Pro Phe Leu Val Trp Tyr Ala Ser Thr Ser Asp Thr
1               5                   10

<210> SEQ ID NO 265
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 265

Ala Val Ser Thr Ala Leu Tyr Asn Thr Trp Gln Val Leu
1               5                   10

<210> SEQ ID NO 266
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 266

Cys Ala His Pro Pro Tyr Lys Glu Asn Tyr Leu Tyr
1               5                   10

<210> SEQ ID NO 267
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 267
```

```
Cys Cys Trp Thr Glu Ala Tyr Asp Ala His Pro Trp Arg
1               5                   10

<210> SEQ ID NO 268
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 268

Cys Lys Phe Phe Phe His Tyr His Ile Gly Phe Ala Thr
1               5                   10

<210> SEQ ID NO 269
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 269

Cys Val Trp Cys Ser Glu Tyr Phe Arg Glu Asp Pro Pro
1               5                   10

<210> SEQ ID NO 270
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 270

Cys Tyr Thr Ser Lys Tyr Tyr Arg Glu Lys Tyr Glu Leu
1               5                   10

<210> SEQ ID NO 271
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 271

Asp Thr Ile Trp Trp Trp Tyr Met Trp Cys Trp His Tyr
1               5                   10

<210> SEQ ID NO 272
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 272

Glu His Gly Pro Phe Val Asp Ser Glu Tyr Pro Gln Pro
1               5                   10

<210> SEQ ID NO 273
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 273

Phe Ala Asp Asn Leu Gly Tyr Val Gly Ser Asp Val Ile
```

```
<210> SEQ ID NO 274
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 274

Phe Ala Pro Met Lys Ser Tyr Gly Val Ser Leu Pro Pro
1               5                   10

<210> SEQ ID NO 275
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 275

Phe Glu Leu Ala Thr Gly Tyr Val Pro Ala Leu Leu Lys
1               5                   10

<210> SEQ ID NO 276
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 276

Phe Phe Phe Ser Met Ser Tyr Phe Phe Phe Arg Ala Ala
1               5                   10

<210> SEQ ID NO 277
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 277

Phe Phe Gly Phe Asp Val Tyr Asp Met Ser Asn Ala Leu
1               5                   10

<210> SEQ ID NO 278
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 278

Phe Phe His Phe Cys Phe Tyr Thr Cys Met Phe His Leu
1               5                   10

<210> SEQ ID NO 279
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 279

Phe Phe Leu Ser Pro Phe Tyr Phe Phe Asn Glu Phe Phe
1               5                   10
```

```
<210> SEQ ID NO 280
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 280

Phe Phe Met Ala Ser Ser Tyr Ser Tyr Pro Val Ala Gly
1               5                   10

<210> SEQ ID NO 281
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 281

Phe Phe Pro Ser Ser Trp Tyr Ser His Leu Gly Val Leu
1               5                   10

<210> SEQ ID NO 282
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 282

Phe Phe Val Leu Phe Leu Tyr Leu Trp Leu Gly Val Ser
1               5                   10

<210> SEQ ID NO 283
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 283

Phe Gly Cys Glu Leu Pro Tyr Ser Gly Val Cys Ser Val
1               5                   10

<210> SEQ ID NO 284
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 284

Phe Gly Ser Asp Val Phe Tyr Leu Arg Ser Ala Pro His
1               5                   10

<210> SEQ ID NO 285
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 285

Phe His Glu Ala Pro Val Tyr Glu Thr Ser Glu Pro Pro
1               5                   10

<210> SEQ ID NO 286
```

-continued

```
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 286

Phe Leu Gly Phe Gln Asp Tyr Lys Ser Ala Ala Met Met
1               5                   10

<210> SEQ ID NO 287
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 287

Phe Leu Leu Thr Gly Glu Tyr Val Asp Val Val Ala Ala
1               5                   10

<210> SEQ ID NO 288
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 288

Phe Leu Ser Phe Ala Asn Tyr Glu Asp Glu Leu Leu Arg
1               5                   10

<210> SEQ ID NO 289
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 289

Phe Met Phe Ile Phe Phe Tyr Pro Val Phe Cys Phe Gln
1               5                   10

<210> SEQ ID NO 290
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 290

Phe Arg Phe Phe Asn His Tyr Arg Tyr Pro Ser Gly Gln
1               5                   10

<210> SEQ ID NO 291
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 291

Phe Arg Met Asp Phe Asp Tyr Leu Tyr Pro Ser Leu Pro
1               5                   10

<210> SEQ ID NO 292
<211> LENGTH: 13
<212> TYPE: PRT
```

<213> ORGANISM: Artificial Sequence
<220> FEATURE:
<223> OTHER INFORMATION: isolated from phage display libraries

<400> SEQUENCE: 292

Phe Arg Tyr Phe Tyr Phe Tyr Ser His Gly Phe Lys Phe
1               5                   10

<210> SEQ ID NO 293
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 293

Phe Ser Ala Leu Pro Thr Tyr Glu Val Asn Ser Tyr Lys
1               5                   10

<210> SEQ ID NO 294
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 294

Phe Ser Asp Ser Ser Phe Tyr Ser Asp Leu Ser Val Val
1               5                   10

<210> SEQ ID NO 295
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 295

Phe Ser Ser Val Asp Ser Tyr Ser Gly Pro Arg Pro Asp
1               5                   10

<210> SEQ ID NO 296
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 296

Phe Ser Tyr Ser Val Ser Tyr Ala His Pro Glu Gly Leu
1               5                   10

<210> SEQ ID NO 297
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 297

Phe Val Gly Phe Phe Leu Tyr Leu Thr Leu Leu Leu Pro
1               5                   10

<210> SEQ ID NO 298
<211> LENGTH: 13
<212> TYPE: PRT
<213> ORGANISM: Artificial Sequence
<220> FEATURE:

```
<223> OTHER INFORMATION: isolated from phage display libraries

<400> SEQUENCE: 298

Gly Glu Asn Phe Cys Pro Tyr Ser Phe Phe Gly Cys Gly
1               5                   10

<210> SEQ ID NO 299
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 299

Gly Phe Ala Trp Ser Ser Tyr Leu Gly Thr Thr Val His
1               5                   10

<210> SEQ ID NO 300
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 300

Gly Phe Pro Phe Ile Phe Tyr Val Val Asp Trp Met Arg
1               5                   10

<210> SEQ ID NO 301
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 301

Gly Phe Ser Glu Phe Leu Tyr Asp Leu Glu Val Gly Ile
1               5                   10

<210> SEQ ID NO 302
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 302

Gly Phe Val Ala Tyr Asn Tyr Asp Lys Tyr Ser Gly Ala
1               5                   10

<210> SEQ ID NO 303
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 303

Gly Val Ser Gln Phe Leu Tyr Asp Trp Val Lys Gly Gly
1               5                   10

<210> SEQ ID NO 304
<211> LENGTH: 13
<212> TYPE: PRT
<213> ORGANISM: Artificial Sequence
<220> FEATURE:
<223> OTHER INFORMATION: isolated from phage display libraries
```

-continued

<400> SEQUENCE: 304

Gly Tyr Asn Ile Tyr Trp Tyr Ile Asn Asn Val Glu Tyr
1               5                   10

<210> SEQ ID NO 305
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 305

His Tyr Lys Tyr Asn Val Tyr Cys Lys Tyr Asn Gly Tyr
1               5                   10

<210> SEQ ID NO 306
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 306

Ile Phe Leu Pro Trp His Tyr Asp Gly Tyr Thr Phe Ala
1               5                   10

<210> SEQ ID NO 307
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 307

Ile Phe Ser Phe Leu Ser Tyr Val Pro Val Asp Lys Val
1               5                   10

<210> SEQ ID NO 308
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 308

Ile Tyr Ala Ala Leu Tyr Tyr Arg Phe Pro Thr Met Asp
1               5                   10

<210> SEQ ID NO 309
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 309

Lys Phe Phe Phe Trp Phe Tyr Ile Asn Phe Val Met Met
1               5                   10

<210> SEQ ID NO 310
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 310

```
Leu Asp Pro Leu Val Pro Tyr Leu Tyr Glu Asn Leu Phe
1               5                   10

<210> SEQ ID NO 311
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 311

Leu Phe Asp Ala Tyr Trp Tyr Ser Asp Thr Ala Met Ser
1               5                   10

<210> SEQ ID NO 312
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 312

Leu Leu Phe Phe Asp Asp Tyr Phe Lys Ser Ala Gly Arg
1               5                   10

<210> SEQ ID NO 313
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 313

Leu Asn Phe Met Ile Phe Tyr Leu Ser Leu Asn Pro Trp
1               5                   10

<210> SEQ ID NO 314
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 314

Leu Pro His Leu Ile Gln Tyr Arg Val Leu Leu Val Ser
1               5                   10

<210> SEQ ID NO 315
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 315

Leu Pro Ser Gln Phe Gly Tyr Gly Ser Val Pro Thr Asp
1               5                   10

<210> SEQ ID NO 316
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 316

Leu Pro Ser Gln Phe Gly Tyr Gly Ser Val Pro Thr Asp
1               5                   10
```

```
<210> SEQ ID NO 317
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 317

Leu Ser Phe Ser Asp Phe Tyr Phe Ser Glu Gly Ser Glu
1               5                   10

<210> SEQ ID NO 318
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 318

Leu Thr Asn Ser Gly Val Tyr Asp Gly Thr Pro Leu Pro
1               5                   10

<210> SEQ ID NO 319
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 319

Leu Val Leu Leu Ile Leu Tyr Leu Phe Leu Ser Trp Pro
1               5                   10

<210> SEQ ID NO 320
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 320

Leu Val Leu Leu Leu Phe Tyr Phe Leu Met Leu Ser Pro
1               5                   10

<210> SEQ ID NO 321
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 321

Leu Tyr Leu Phe Tyr Pro Tyr Pro Asn Tyr Tyr Met Val
1               5                   10

<210> SEQ ID NO 322
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 322

Asn Phe Ser Ser Ser Phe Tyr Ser Leu Val Ser Glu Gly
1               5                   10
```

```
<210> SEQ ID NO 323
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 323

Asn Trp Tyr Ala Glu Tyr Tyr Tyr Val Tyr Asp Lys Gly
1               5                   10

<210> SEQ ID NO 324
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 324

Asn Tyr Phe Ser Ala Met Tyr Tyr Asp Gly Trp Met Ser
1               5                   10

<210> SEQ ID NO 325
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 325

Pro Ala Ser Leu Glu Leu Tyr Glu Asn Leu Val Ala Gly
1               5                   10

<210> SEQ ID NO 326
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 326

Pro Cys Trp Tyr Arg Tyr Tyr His Glu Phe Trp Ile Trp
1               5                   10

<210> SEQ ID NO 327
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 327

Pro Leu Tyr Tyr Glu Ser Tyr Arg Met Arg Thr Tyr Gln
1               5                   10

<210> SEQ ID NO 328
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 328

Gln Tyr Ala Ser Tyr Met Tyr Tyr Cys Phe Pro Lys Tyr
1               5                   10

<210> SEQ ID NO 329
<211> LENGTH: 13
```

```
<212> TYPE: PRT
<213> ORGANISM: Artificial Sequence
<220> FEATURE:
<223> OTHER INFORMATION: isolated from phage display libraries

<400> SEQUENCE: 329

Arg Ala Trp Trp Trp Trp Tyr Leu Asp Met Tyr Trp Thr
1               5                   10

<210> SEQ ID NO 330
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 330

Arg Ala Tyr Asn Tyr Tyr Tyr Val Met Tyr Ala Cys
1               5                   10

<210> SEQ ID NO 331
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 331

Arg Trp Ile Trp Trp Pro Tyr Val Asn Met Ile Trp Thr
1               5                   10

<210> SEQ ID NO 332
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 332

Ser Asp Phe Leu Ser Pro Tyr Leu Ala Tyr Glu Arg Ser
1               5                   10

<210> SEQ ID NO 333
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 333

Ser Phe Asp Val Arg Ser Tyr Val Leu Ala Gly Thr Glu
1               5                   10

<210> SEQ ID NO 334
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 334

Ser Leu Phe Leu Asp Asp Tyr Ala Leu Gly Pro Arg Val
1               5                   10

<210> SEQ ID NO 335
<211> LENGTH: 13
<212> TYPE: PRT
<213> ORGANISM: Artificial Sequence
```

```
<220> FEATURE:
<223> OTHER INFORMATION: isolated from phage display libraries

<400> SEQUENCE: 335

Ser Ser Val Leu Gly Phe Tyr Asp Pro Val Glu Val Ser
1               5                   10

<210> SEQ ID NO 336
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 336

Ser Val Ala Phe Tyr Asp Tyr Leu Pro Thr Asp Leu Pro
1               5                   10

<210> SEQ ID NO 337
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 337

Ser Val Leu Asp Phe Asn Tyr Gly His Asp Val Asn Val
1               5                   10

<210> SEQ ID NO 338
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 338

Ser Val Ser Asp Phe Leu Tyr Arg Ser Ile Tyr Ser Leu
1               5                   10

<210> SEQ ID NO 339
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 339

Ser Val Ser Asp Phe Leu Tyr Arg Ser Ile Tyr Ser Leu
1               5                   10

<210> SEQ ID NO 340
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 340

Ser Val Ser Asp Phe Leu Tyr Arg Ser Ile Tyr Ser Leu
1               5                   10

<210> SEQ ID NO 341
<211> LENGTH: 13
<212> TYPE: PRT
<213> ORGANISM: Artificial Sequence
<220> FEATURE:
<223> OTHER INFORMATION: isolated from phage display libraries
```

```
<400> SEQUENCE: 341

Ser Trp Ser Trp Trp Arg Tyr Gly Pro Gln Asn Thr Val
1               5                   10

<210> SEQ ID NO 342
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 342

Ser Tyr Gly Phe Pro Ile Tyr Asp Ala Leu Leu Glu Gln
1               5                   10

<210> SEQ ID NO 343
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 343

Val Phe Asp Val Gly Leu Tyr Trp His Ala Ala Pro Pro
1               5                   10

<210> SEQ ID NO 344
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 344

Val Gly Phe Trp Val Asp Tyr Asp Asn Ser Ser Val Met
1               5                   10

<210> SEQ ID NO 345
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 345

Val Leu Asp Leu Pro Tyr Tyr Trp Pro Val Lys Tyr Thr
1               5                   10

<210> SEQ ID NO 346
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 346

Val Leu Leu Ala Asp Ser Tyr Gln Arg Asp Glu His Met
1               5                   10

<210> SEQ ID NO 347
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 347
```

Val Leu Leu Phe Asp Asp Tyr Gly Tyr Ala Glu Ser Ala
1               5                   10

<210> SEQ ID NO 348
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 348

Val Ser Ala Ser Gly Met Tyr Asp Gly Val Asp Leu Met
1               5                   10

<210> SEQ ID NO 349
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 349

Val Ser Leu Leu Phe Ser Tyr Ser Pro Ala Gly Tyr Asp
1               5                   10

<210> SEQ ID NO 350
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 350

Val Ser Ser Glu Trp Thr Tyr Gly Ala Val Ala Asp Leu
1               5                   10

<210> SEQ ID NO 351
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 351

Val Ser Val Leu Ser Asp Tyr Ser Ile Lys Ala Leu Leu
1               5                   10

<210> SEQ ID NO 352
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 352

Trp Ala Asp Met Tyr Tyr Tyr Asp Trp Tyr Thr Met
1               5                   10

<210> SEQ ID NO 353
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 353

Trp Asp Trp Trp Gln Phe Tyr Glu Lys Met Trp Leu Phe

```
<210> SEQ ID NO 354
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 354

Trp Asn Trp Trp Gly Val Tyr Leu Gly Ile Cys Trp Leu
1               5                   10

<210> SEQ ID NO 355
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 355

Trp Trp Gln Thr Trp Trp Tyr Arg Thr Tyr Trp Glu Ile
1               5                   10

<210> SEQ ID NO 356
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 356

Tyr Ala Gly Val Tyr Ser Tyr Phe Thr Gly Ser Thr Leu
1               5                   10

<210> SEQ ID NO 357
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 357

Tyr Cys Gln Tyr Arg Glu Tyr Tyr Thr Met Tyr Val Cys
1               5                   10

<210> SEQ ID NO 358
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 358

Tyr Phe Val Glu Thr Tyr Tyr Asn Arg Tyr His Val Ser
1               5                   10

<210> SEQ ID NO 359
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 359

Tyr Leu Ser Leu His Ala Tyr Glu Ser Phe Gly Gly Ser
1               5                   10
```

```
<210> SEQ ID NO 360
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 360

Tyr Arg Tyr Gln Met Ser Tyr Tyr Ala Tyr Gln Tyr His
1               5                   10

<210> SEQ ID NO 361
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 361

Tyr Ser Met Tyr Pro Ile Tyr Asn Lys Cys Ser Gln His
1               5                   10

<210> SEQ ID NO 362
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 362

Tyr Trp Ile Tyr Asn Asn Tyr Thr Tyr Tyr Tyr Cys Gly
1               5                   10

<210> SEQ ID NO 363
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 363

Tyr Trp Trp Glu Gln Trp Tyr Ser Trp Trp Ile Glu His
1               5                   10

<210> SEQ ID NO 364
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 364

Tyr Tyr Arg Asp Ala Ser Tyr Thr Tyr Pro Tyr Met Tyr
1               5                   10

<210> SEQ ID NO 365
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 365

Tyr Tyr Tyr Ile Pro Val Tyr Ser Ala Gln Cys Tyr Thr
1               5                   10

<210> SEQ ID NO 366
```

```
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 366

Ala Cys Pro Trp Pro Ile Pro Pro Trp Pro Leu Arg Val
1               5                   10

<210> SEQ ID NO 367
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 367

Ala Arg Arg Trp Pro Leu Pro Arg Arg Asp Gln Phe Ser
1               5                   10

<210> SEQ ID NO 368
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 368

Cys Arg Arg Ile Gln Gln Pro Cys Val Phe Arg Arg His
1               5                   10

<210> SEQ ID NO 369
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 369

Asp Glu Pro Pro Cys Ala Pro Glu Cys Asn Gly Asp Gly
1               5                   10

<210> SEQ ID NO 370
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 370

Asp Phe Gln Phe Pro Lys Pro Ala Phe Cys Ser Thr Cys
1               5                   10

<210> SEQ ID NO 371
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 371

Glu Leu Tyr Phe Phe Phe Pro Cys Gly Ser Phe Cys Gln
1               5                   10

<210> SEQ ID NO 372
<211> LENGTH: 13
<212> TYPE: PRT
```

<213> ORGANISM: Artificial Sequence
<220> FEATURE:
<223> OTHER INFORMATION: isolated from phage display libraries

<400> SEQUENCE: 372

Phe Phe Gly Phe Asn His Pro Phe Leu Phe Ser Cys Trp
1               5                   10

<210> SEQ ID NO 373
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 373

Phe Phe Gln Ser Ile Gln Pro Ile Phe Ala Arg Ser Met
1               5                   10

<210> SEQ ID NO 374
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 374

Phe Phe Trp Val Lys Asp Pro Ser Pro Cys Phe Asp His
1               5                   10

<210> SEQ ID NO 375
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 375

Phe Gly Lys Phe Phe Asp Pro Leu Arg Arg Ala Lys Asp
1               5                   10

<210> SEQ ID NO 376
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 376

Phe Lys Gly Glu Phe Trp Pro Ala Phe Gly Val Gln Val
1               5                   10

<210> SEQ ID NO 377
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 377

Phe Lys Leu His Trp Phe Pro Thr Cys Pro Phe Ile Gln
1               5                   10

<210> SEQ ID NO 378
<211> LENGTH: 13
<212> TYPE: PRT
<213> ORGANISM: Artificial Sequence
<220> FEATURE:

<223> OTHER INFORMATION: isolated from phage display libraries

<400> SEQUENCE: 378

Phe Leu Ser Phe Val Phe Pro Ala Ser Ala Trp Gly Gly
1               5                   10

<210> SEQ ID NO 379
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 379

Phe Met Asp Ile Trp Ser Pro Trp His Leu Leu Gly Thr
1               5                   10

<210> SEQ ID NO 380
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 380

Phe Asn Pro Pro Glu Pro Pro Cys Pro Glu Phe Ser Lys
1               5                   10

<210> SEQ ID NO 381
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 381

Phe Gln Phe Phe Asp Pro Pro Ser Phe Phe Gly Phe Lys
1               5                   10

<210> SEQ ID NO 382
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 382

Phe Gln Phe Ser Phe Gln Pro Asp Gly Val Glu Arg Arg
1               5                   10

<210> SEQ ID NO 383
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 383

Phe Gln Asn Cys Phe Trp Pro Ile Phe Glu Ala Met Glu
1               5                   10

<210> SEQ ID NO 384
<211> LENGTH: 13
<212> TYPE: PRT
<213> ORGANISM: Artificial Sequence
<220> FEATURE:
<223> OTHER INFORMATION: isolated from phage display libraries

```
<400> SEQUENCE: 384

Phe Ser Phe Phe Ala Asp Pro Ile Glu Leu Glu Trp Asp
1               5                   10

<210> SEQ ID NO 385
<211> LENGTH: 12
<212> TYPE: PRT
<213> ORGANISM: Artificial Sequence
<220> FEATURE:
<223> OTHER INFORMATION: isolated from phage display libraries

<400> SEQUENCE: 385

Phe Ser Ser Leu Phe Phe Pro His Trp Ala Gln Leu
1               5                   10

<210> SEQ ID NO 386
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 386

Phe Tyr Met Pro Phe Gly Pro Thr Trp Trp Gln His Val
1               5                   10

<210> SEQ ID NO 387
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 387

Phe Tyr Tyr Phe Gly Phe Pro Gln Cys Leu Ile Leu Phe
1               5                   10

<210> SEQ ID NO 388
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 388

Gly Phe Glu Glu Phe Gln Pro Val Asp Phe Ile Ile Arg
1               5                   10

<210> SEQ ID NO 389
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 389

Gly Leu Thr Arg Phe Phe Pro Val Ser Phe Ser Phe Phe
1               5                   10

<210> SEQ ID NO 390
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 390
```

```
His Ala Arg Pro Pro Cys Pro Phe Val Asn Glu Lys Pro
1               5                   10
```

<210> SEQ ID NO 391
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 391

```
His Glu Phe Met Trp Phe Pro Val His Trp Glu Phe His
1               5                   10
```

<210> SEQ ID NO 392
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 392

```
His Arg Asn Pro Arg Arg Pro Gln Ile Glu Gly Val Arg
1               5                   10
```

<210> SEQ ID NO 393
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 393

```
Ile Ser Gly His Cys Phe Pro Cys Ile Glu Val Ser Asp
1               5                   10
```

<210> SEQ ID NO 394
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 394

```
Lys Phe Gln Asp Phe Met Pro Gln Met Phe His Gly Ile
1               5                   10
```

<210> SEQ ID NO 395
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 395

```
Leu Phe Phe Met Pro Phe Pro Phe Phe Phe Phe Pro Tyr
1               5                   10
```

<210> SEQ ID NO 396
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 396

```
Leu Phe Ser Trp Phe Leu Pro Thr Asp Asn Tyr Pro Val
1               5                   10
```

```
<210> SEQ ID NO 397
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 397

Leu Val Cys Ile Arg Arg Pro Arg Arg Arg Cys Phe Cys
1               5                   10

<210> SEQ ID NO 398
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 398

Met Pro Arg Arg Glu Arg Pro Leu Trp Met Leu Thr Arg
1               5                   10

<210> SEQ ID NO 399
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 399

Met Arg Arg His Arg Ala Pro Arg Ser Gln Cys Met Glu
1               5                   10

<210> SEQ ID NO 400
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 400

Asn Phe Phe Gly Pro Ile Pro Met Asn Phe Ala Phe Thr
1               5                   10

<210> SEQ ID NO 401
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 401

Asn Phe Phe Ser Ile Asp Pro Phe Cys Gln Ala Ile Tyr
1               5                   10

<210> SEQ ID NO 402
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 402

Asn Asn Gly Ala Arg Arg Pro Tyr Val Ala Ser Asn Pro
1               5                   10
```

```
<210> SEQ ID NO 403
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 403

Asn Arg Arg Arg Tyr Arg Pro Arg Phe Tyr Arg Arg Cys
1               5                   10

<210> SEQ ID NO 404
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 404

Pro Phe Phe Trp Met Phe Pro Ile Cys Phe Pro Pro Asn
1               5                   10

<210> SEQ ID NO 405
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 405

Pro Phe Gly Leu Phe Pro Pro Gln Val Tyr Tyr Phe Leu
1               5                   10

<210> SEQ ID NO 406
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 406

Pro Gly Ala Ala Pro Pro Pro Cys Asn Asn Ser Asp Asn
1               5                   10

<210> SEQ ID NO 407
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 407

Pro Pro Cys Pro Trp Arg Pro Ser Ala Thr His Leu Pro
1               5                   10

<210> SEQ ID NO 408
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 408

Pro Pro Lys Phe Leu Ala Pro His Thr Ser Ala Met Leu
1               5                   10

<210> SEQ ID NO 409
<211> LENGTH: 13
```

```
<212> TYPE: PRT
<213> ORGANISM: Artificial Sequence
<220> FEATURE:
<223> OTHER INFORMATION: isolated from phage display libraries

<400> SEQUENCE: 409

Pro Pro Arg Val Ala Phe Pro Ile Arg Gln Arg Arg Val
1               5                   10

<210> SEQ ID NO 410
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 410

Pro Thr Arg Pro Asn Gly Pro Glu Ser Glu Asp Leu Phe
1               5                   10

<210> SEQ ID NO 411
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 411

Gln Cys Pro Asp Pro Ser Pro Ser Lys Cys Pro Phe Gly
1               5                   10

<210> SEQ ID NO 412
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 412

Gln Arg Arg Ala Pro Arg Pro Ser Glu His Arg Arg Glu
1               5                   10

<210> SEQ ID NO 413
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 413

Arg Ala Arg Arg Ala Gly Pro Leu Gly Asp Arg Lys Leu
1               5                   10

<210> SEQ ID NO 414
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 414

Arg Glu Gly Arg Thr Arg Pro Arg Tyr Pro Arg Trp Phe
1               5                   10

<210> SEQ ID NO 415
<211> LENGTH: 13
<212> TYPE: PRT
<213> ORGANISM: Artificial Sequence
```

```
<220> FEATURE:
<223> OTHER INFORMATION: isolated from phage display libraries

<400> SEQUENCE: 415

Arg Glu Pro Asn Pro Pro Pro Leu Gln Ser Pro Met Ser
1               5                   10

<210> SEQ ID NO 416
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 416

Arg Gly Phe Gln Phe Gly Pro Ser Thr Phe Glu Tyr Phe
1               5                   10

<210> SEQ ID NO 417
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 417

Arg Gly Pro Arg Arg Thr Pro Thr Ile His Arg Pro Trp
1               5                   10

<210> SEQ ID NO 418
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 418

Arg His Phe His Val Arg Pro Val Asn Trp Trp Ser Lys
1               5                   10

<210> SEQ ID NO 419
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 419

Arg Ile Asn Arg Ser Arg Pro Ile Met Trp Gln Arg Thr
1               5                   10

<210> SEQ ID NO 420
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 420

Arg Asn Asp Arg Val Arg Pro Trp Lys Val Lys His Gln
1               5                   10

<210> SEQ ID NO 421
<211> LENGTH: 13
<212> TYPE: PRT
<213> ORGANISM: Artificial Sequence
<220> FEATURE:
<223> OTHER INFORMATION: isolated from phage display libraries
```

```
<400> SEQUENCE: 421

Arg Asn Met Arg Tyr Arg Pro Gln Tyr Ala Asp Leu Cys
1               5                   10

<210> SEQ ID NO 422
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 422

Arg Asn Asn Arg Pro Lys Pro Thr Gln Ser His Arg Val
1               5                   10

<210> SEQ ID NO 423
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 423

Arg Arg His Arg Trp Trp Pro Gln Glu Phe Ser Arg His
1               5                   10

<210> SEQ ID NO 424
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 424

Arg Arg Arg Leu Phe Thr Pro Asn Ser Arg Ala Arg His
1               5                   10

<210> SEQ ID NO 425
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 425

Arg Arg Ser Arg Phe Val Pro Glu Tyr Leu Phe Arg Pro
1               5                   10

<210> SEQ ID NO 426
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 426

Arg Trp His Pro Arg Tyr Pro Val Met Lys Lys Asn Ser
1               5                   10

<210> SEQ ID NO 427
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 427
```

```
Arg Trp Ile Pro Arg Pro Pro Arg Arg Ala Cys Arg Arg
1               5                   10

<210> SEQ ID NO 428
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 428

Ser Phe Trp Pro Phe Cys Pro Thr Thr Trp Ala Asn Tyr
1               5                   10

<210> SEQ ID NO 429
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 429

Ser Ile Phe Gln Phe Asn Pro Phe Pro Glu Gly Phe Phe
1               5                   10

<210> SEQ ID NO 430
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 430

Ser Leu Phe Phe Met Pro Pro Glu Arg Leu Asp His Arg
1               5                   10

<210> SEQ ID NO 431
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 431

Ser Asn Arg His Arg Arg Pro Arg Arg Arg Trp Arg Met
1               5                   10

<210> SEQ ID NO 432
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 432

Thr Phe Phe Thr Asn Lys Pro Phe Ser Tyr His Phe Glu
1               5                   10

<210> SEQ ID NO 433
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 433

Thr Thr Pro Val Gln Pro Pro Gly Glu Val Ser Gln Val
```

```
1               5                   10

<210> SEQ ID NO 434
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 434

Thr Tyr Asn Ser Phe Phe Pro Phe Arg His Phe Ala Glu
1               5                   10

<210> SEQ ID NO 435
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 435

Val Lys Ile Arg Arg Arg Pro Arg Arg Met Arg Leu Met
1               5                   10

<210> SEQ ID NO 436
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 436

Trp Lys His Pro Pro Arg Pro Tyr Cys Trp Lys Pro Leu
1               5                   10

<210> SEQ ID NO 437
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 437

Tyr Ile Tyr Thr Val Tyr Pro Arg Asn Ser Ser Trp Phe
1               5                   10

<210> SEQ ID NO 438
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 438

Tyr Gln Pro Trp Gly Pro Pro Pro Pro Pro Leu Val Leu
1               5                   10

<210> SEQ ID NO 439
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 439

Ala Arg Asp Tyr Asp Asn Asn Met Lys Tyr Tyr Leu Asp
1               5                   10
```

<210> SEQ ID NO 440
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 440

Ala Arg Ile Asn Asn Lys Asn Val Ile Thr Phe Gln Pro
1               5                   10

<210> SEQ ID NO 441
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 441

Ala Ser Arg Ser Ser Asp Asn Ile Ser Tyr Ser Ser Thr
1               5                   10

<210> SEQ ID NO 442
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 442

Ala Ser Ser Asp Ala Gly Asn Tyr Glu Ile Ala Gly Pro
1               5                   10

<210> SEQ ID NO 443
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 443

Ala Thr Asp Asp Glu Asn Asn Glu Met Asn Val Gly Met
1               5                   10

<210> SEQ ID NO 444
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 444

Cys Ser Ser Phe Ser Leu Asn Trp Ser Leu Ser Lys Ser
1               5                   10

<210> SEQ ID NO 445
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 445

Asp Cys Asp His Leu Phe Asn Met Glu Gln Thr Leu Arg
1               5                   10

<210> SEQ ID NO 446

```
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 446

Asp Cys Val Ser Ser Asn Asn His Asp Ile Thr Arg Gly
1               5                   10

<210> SEQ ID NO 447
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 447

Asp Asp Glu Arg Val Ile Asn Ser Asp Tyr Ser Glu Tyr
1               5                   10

<210> SEQ ID NO 448
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 448

Asp Asp Lys Asn Glu Asp Asn Asp Ile Pro Lys Thr Pro
1               5                   10

<210> SEQ ID NO 449
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 449

Asp Asp Thr Asn Asp Met Asn Asn Ser Glu Glu Lys Phe
1               5                   10

<210> SEQ ID NO 450
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 450

Asp Asp Val Gln Asp Asp Asn Asp Gln Pro Tyr Asn Thr
1               5                   10

<210> SEQ ID NO 451
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 451

Asp Lys Gly Asn Asp Gln Asn Asn Ser Pro Leu Trp Ala
1               5                   10

<210> SEQ ID NO 452
<211> LENGTH: 13
<212> TYPE: PRT
```

```
<213> ORGANISM: Artificial Sequence
<220> FEATURE:
<223> OTHER INFORMATION: isolated from phage display libraries

<400> SEQUENCE: 452

Asp Leu Val Cys Asn Asn Cys Arg Asn Leu Phe Asn
1               5                   10

<210> SEQ ID NO 453
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 453

Asp Asn His Asp Lys Phe Asn Gln Ala Ile Gln Asp Trp
1               5                   10

<210> SEQ ID NO 454
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 454

Asp Arg Cys Asn Gly Asp Asn Trp Cys Asn Gln Gly Asp
1               5                   10

<210> SEQ ID NO 455
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 455

Asp Ser Glu Tyr Leu Ser Asn Lys Ser Val Asn Asp Phe
1               5                   10

<210> SEQ ID NO 456
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 456

Asp Thr Met Thr Asp Asn Asn Gln Gly Asp Asp Gln Trp
1               5                   10

<210> SEQ ID NO 457
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 457

Glu Lys Asn Trp Asn Tyr Asn Pro Val Met Leu Ala Asn
1               5                   10

<210> SEQ ID NO 458
<211> LENGTH: 13
<212> TYPE: PRT
<213> ORGANISM: Artificial Sequence
<220> FEATURE:
```

<223> OTHER INFORMATION: isolated from phage display libraries

<400> SEQUENCE: 458

Phe Phe Ser Phe Leu Pro Asn Ser Asp Arg Phe Gln Trp
1               5                   10

<210> SEQ ID NO 459
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 459

Phe Phe Ser Tyr Trp Ser Asn Phe Asp Ala Ser Trp His
1               5                   10

<210> SEQ ID NO 460
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 460

Phe His Ile Asp Asp Asp Asn Asp Phe Asp Thr Thr Ser
1               5                   10

<210> SEQ ID NO 461
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 461

Phe Asn Asn Phe Asn Asp Asn Glu His Asn Val Asn Lys
1               5                   10

<210> SEQ ID NO 462
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 462

Phe Tyr Asn Ile Val Asn Asn Ile Phe Ile Cys Cys Ile
1               5                   10

<210> SEQ ID NO 463
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 463

Phe Tyr Trp Asp Arg Leu Asn Val Gly Trp Gly Leu Leu
1               5                   10

<210> SEQ ID NO 464
<211> LENGTH: 13
<212> TYPE: PRT
<213> ORGANISM: Artificial Sequence
<220> FEATURE:
<223> OTHER INFORMATION: isolated from phage display libraries

```
<400> SEQUENCE: 464

Gly Asp Asn His Asn His Asn Thr Asn Thr Ile Glu Pro
1               5                   10

<210> SEQ ID NO 465
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 465

His Ala Asp Gln Asp Asp Asn Cys Arg Gly Lys Asp Asp
1               5                   10

<210> SEQ ID NO 466
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 466

His Asp Trp Asp Asp Trp Asn Ile Glu Ala Glu Asp Gly
1               5                   10

<210> SEQ ID NO 467
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 467

His Gly Ser Ser Asp Thr Asn Gly Gln Ile Leu Phe Glu
1               5                   10

<210> SEQ ID NO 468
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 468

His Asn Trp Asn His Asn Asn Asn Leu Ile Asp Arg Phe
1               5                   10

<210> SEQ ID NO 469
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 469

Ile Cys Asp Asp Asp Asn Asn Met His Leu Tyr Glu Pro
1               5                   10

<210> SEQ ID NO 470
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 470
```

```
Ile Asp Ser His Leu Asn Asp Gln Cys Arg Asp Asp
1               5                   10

<210> SEQ ID NO 471
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 471

Ile Asn Cys Asn Asn Asn Ser Leu Asn Asn Asn Asn
1               5                   10

<210> SEQ ID NO 472
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 472

Ile Asn Asn Val Val Tyr Asn Leu His Asp Arg Asn Asn
1               5                   10

<210> SEQ ID NO 473
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 473

Ile Ser Asn Cys Asn Ile Asn Asn Gly Asn Asn Asp Ser
1               5                   10

<210> SEQ ID NO 474
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 474

Ile Ser Asn Arg Gln Ser Asn Thr Ser Asn Gly Met Ser
1               5                   10

<210> SEQ ID NO 475
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 475

Lys Phe Ser Ser Leu His Asn Ile Ser Gly Pro Lys Ser
1               5                   10

<210> SEQ ID NO 476
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 476

Lys Asn Leu Asn Gln Asn Asn Asn Asn His Phe Asn Asn
1               5                   10
```

```
<210> SEQ ID NO 477
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 477

Lys Asn Arg Val Asn Lys Asn Thr Asn Val His Cys Phe
1               5                   10

<210> SEQ ID NO 478
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 478

Leu Ser Asn Leu Asn Tyr Asn Pro Asn His His Asp Met
1               5                   10

<210> SEQ ID NO 479
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 479

Met Arg Ser Ser Ser Phe Asn Phe Gly Ser Phe Asp Gln
1               5                   10

<210> SEQ ID NO 480
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 480

Met Ser Asn Ser Ser Ser Asn Ser Ser Ser Ser Ser Gly
1               5                   10

<210> SEQ ID NO 481
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 481

Met Tyr Ser Asn Tyr Tyr Asn Phe Leu Gln Lys Ser Trp
1               5                   10

<210> SEQ ID NO 482
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 482

Asn Asp Arg Asn Asp His Asn Gln His Arg Tyr Asp His
1               5                   10
```

```
<210> SEQ ID NO 483
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 483

Asn Glu Met Trp Asn Asn Asn Val Met Asn His His
1               5                   10

<210> SEQ ID NO 484
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 484

Asn Glu Asn Glu Asn Asp Asn Asn Met Asn Met Glu Ile
1               5                   10

<210> SEQ ID NO 485
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 485

Asn Asn Asn Ser Asn His Asn Asp Pro Thr Asn Ala Glu
1               5                   10

<210> SEQ ID NO 486
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 486

Asn Asn Val Leu Asn His Asn Cys Asn Met Phe Leu Asn
1               5                   10

<210> SEQ ID NO 487
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 487

Asn Pro Thr Lys Asn Arg Asn Thr His Leu Gly Gly Arg
1               5                   10

<210> SEQ ID NO 488
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 488

Asn Arg Glu Val Lys Asn Asn Arg Gln Lys Val Phe Lys
1               5                   10

<210> SEQ ID NO 489
<211> LENGTH: 13
```

```
<212> TYPE: PRT
<213> ORGANISM: Artificial Sequence
<220> FEATURE:
<223> OTHER INFORMATION: isolated from phage display libraries

<400> SEQUENCE: 489

Asn Arg Asn Asn His Phe Asn Asn Glu Tyr Glu Trp Asn
1               5                   10

<210> SEQ ID NO 490
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 490

Asn Thr Asp Leu Asn Asn Asn Gln Thr Val Ser Asn Arg
1               5                   10

<210> SEQ ID NO 491
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 491

Pro Asp Asp Ala Pro His Asn Tyr Cys Thr Asp Pro Leu
1               5                   10

<210> SEQ ID NO 492
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 492

Pro Lys Asp Asp Arg Asn Asn Thr Val Ala Ser Cys Glu
1               5                   10

<210> SEQ ID NO 493
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 493

Pro Val Asn Tyr Ala Asn Asn Pro Glu Arg Val Gly His
1               5                   10

<210> SEQ ID NO 494
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 494

Pro Tyr Asn Gly Ser Asn Asn Asn Ala Thr Val Pro
1               5                   10

<210> SEQ ID NO 495
<211> LENGTH: 13
<212> TYPE: PRT
<213> ORGANISM: Artificial Sequence
```

```
<220> FEATURE:
<223> OTHER INFORMATION: isolated from phage display libraries

<400> SEQUENCE: 495

Gln Asn Ser Gln His Asn Asn His His Cys Val Leu Gly
1               5                   10

<210> SEQ ID NO 496
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 496

Arg Ser Ser Ser Ser Gly Asn Ser Ser His His His Met
1               5                   10

<210> SEQ ID NO 497
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 497

Ser Glu Ser Asn Ser Asn Asn Pro Gly His Asn Leu Pro
1               5                   10

<210> SEQ ID NO 498
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 498

Ser Phe Leu Asn Asn Cys Asn His Asn Lys Leu Met Ser
1               5                   10

<210> SEQ ID NO 499
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 499

Ser Ile Phe Asn Ser Ser Asn His Thr His Gln Ser Met
1               5                   10

<210> SEQ ID NO 500
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 500

Ser Asn Met Asp Ser Ser Asn Ala Pro Gln Ser Trp Val
1               5                   10

<210> SEQ ID NO 501
<211> LENGTH: 13
<212> TYPE: PRT
<213> ORGANISM: Artificial Sequence
<220> FEATURE:
<223> OTHER INFORMATION: isolated from phage display libraries
```

```
<400> SEQUENCE: 501

Ser Asn Ser Trp Asn Asn Asn Glu Asp Lys His Ile Leu
1               5                   10

<210> SEQ ID NO 502
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 502

Ser Arg Ser Gly Trp Ser Asn Tyr Phe Cys Ser Arg Gln
1               5                   10

<210> SEQ ID NO 503
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 503

Ser Ser Met Leu His Asn Asn Pro Trp Ser Lys Trp Ser
1               5                   10

<210> SEQ ID NO 504
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 504

Ser Ser Asn Gln Val Ile Asn Thr Phe Glu Asp Leu Gln
1               5                   10

<210> SEQ ID NO 505
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 505

Ser Ser Gln Ser Met Pro Asn Gly Ser Gly Lys Glu Thr
1               5                   10

<210> SEQ ID NO 506
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 506

Ser Val Ser Cys Ser Cys Asn Thr Ser Arg Gly Cys Ser
1               5                   10

<210> SEQ ID NO 507
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 507
```

```
Ser Val Ser Ser Lys Ser Asn Glu Ile Ser Phe Cys Thr
1               5                   10
```

<210> SEQ ID NO 508
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 508

```
Thr Asp Ser Gly Ser Ser Asn Ser Ala Lys Ala Ile Cys
1               5                   10
```

<210> SEQ ID NO 509
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 509

```
Thr Asn Trp Cys Ser Ser Asn Val Gly Ser Asn Thr Ser
1               5                   10
```

<210> SEQ ID NO 510
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 510

```
Thr Ser Ser Trp Ser Phe Asn Gly Thr Asn Gly Ser Ala
1               5                   10
```

<210> SEQ ID NO 511
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 511

```
Val Ala Asp Ser Phe Asp Asn Ala Asn Tyr Thr Leu Asp
1               5                   10
```

<210> SEQ ID NO 512
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 512

```
Val Asp Asp Gln Tyr Asp Asn Trp Asp Ile Arg Asp Cys
1               5                   10
```

<210> SEQ ID NO 513
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 513

```
Tyr Asn Gly Asn Tyr His Asn His Gly Leu Asn Ile Arg
```

```
<210> SEQ ID NO 514
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 514

Cys Phe Val Leu Asn Cys His Leu Val Leu Asp Arg Pro
1               5                   10

<210> SEQ ID NO 515
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 515

Cys Arg Arg Pro Phe Glu His Ala Leu Phe Tyr Ala Ser
1               5                   10

<210> SEQ ID NO 516
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 516

Asp Ser Trp Leu Leu Ser His Ser Arg Ser Lys Ser Met
1               5                   10

<210> SEQ ID NO 517
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 517

Asp Ser Trp Trp Thr Gln His Ser Gln Ala His Ser Asp
1               5                   10

<210> SEQ ID NO 518
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 518

Asp Thr Asn Met Leu Asn His Gly Met Tyr Gly His Cys
1               5                   10

<210> SEQ ID NO 519
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 519

Glu Asn Ile Asn Ala Ser His Cys Leu Ser Thr Val Asp
1               5                   10
```

```
<210> SEQ ID NO 520
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 520

Phe Phe Ser Tyr Ser Gly His Leu Val Gln Lys Val Trp
1               5                   10

<210> SEQ ID NO 521
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 521

Phe Met Phe Ala Val Trp His Asp Gly His Ile Lys Asn
1               5                   10

<210> SEQ ID NO 522
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 522

Phe Met Ser Gln His Phe His Asn Pro Met Met Ile Arg
1               5                   10

<210> SEQ ID NO 523
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 523

Phe Val Phe Tyr Ile Met His Tyr Cys Gly His Phe Met
1               5                   10

<210> SEQ ID NO 524
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 524

His Phe Lys Asp Asp Asp His Met Met Leu Tyr Gly Pro
1               5                   10

<210> SEQ ID NO 525
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 525

His Thr Gln His Arg Leu His Val Gly Gln Ser Ser Ser
1               5                   10

<210> SEQ ID NO 526
```

```
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 526

Ile Ser Asn Ser Trp Tyr His Trp Ser Trp Glu Met Trp
1               5                   10

<210> SEQ ID NO 527
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 527

Leu Cys Phe Tyr Glu Tyr His Phe Met Gln Cys Ala Met
1               5                   10

<210> SEQ ID NO 528
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 528

Leu Gly Leu Ser Asp Ser His Tyr Glu Cys Ser Phe Arg
1               5                   10

<210> SEQ ID NO 529
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 529

Leu Arg Ser Thr Ser Phe His Phe Arg Cys Ala Lys Cys
1               5                   10

<210> SEQ ID NO 530
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 530

Leu Ser Val Phe Ser His His Lys Trp Val Tyr Thr Ser
1               5                   10

<210> SEQ ID NO 531
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 531

Met Ala Met His His Met His His Met Ala Asn Asn Leu
1               5                   10

<210> SEQ ID NO 532
<211> LENGTH: 13
<212> TYPE: PRT
```

<213> ORGANISM: Artificial Sequence
<220> FEATURE:
<223> OTHER INFORMATION: isolated from phage display libraries

<400> SEQUENCE: 532

Met Ser Ser Phe Asp Val His Arg Ser His Thr Asn Ser
1               5                   10

<210> SEQ ID NO 533
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 533

Pro Gly Ser Leu Ser Glu His Ile Tyr Gln Ala Trp Ser
1               5                   10

<210> SEQ ID NO 534
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 534

Pro Ser Ser Ala Ser Met His Ile Ala Ser Ser Cys Ile
1               5                   10

<210> SEQ ID NO 535
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 535

Gln Tyr Trp Trp Ile Trp His Lys Ser Asp Ser Gly Ser
1               5                   10

<210> SEQ ID NO 536
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 536

Ser Gly Gln Ser Asn Ser His His Asp Lys Thr Ile Cys
1               5                   10

<210> SEQ ID NO 537
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 537

Ser Gly Gln Ser Val Phe His His Phe Phe Pro Asn Asp
1               5                   10

<210> SEQ ID NO 538
<211> LENGTH: 13
<212> TYPE: PRT
<213> ORGANISM: Artificial Sequence
<220> FEATURE:

-continued

<223> OTHER INFORMATION: isolated from phage display libraries

<400> SEQUENCE: 538

Ser His Val Ser Leu Tyr His Ala Ser Thr Asp Ser Asp
1               5                   10

<210> SEQ ID NO 539
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 539

Ser Met Ser Ser Ser Lys His Met Asp Met Asp Cys Phe
1               5                   10

<210> SEQ ID NO 540
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 540

Ser Ser Cys Leu Pro Ser His Val Arg Ser Asp Thr Lys
1               5                   10

<210> SEQ ID NO 541
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 541

Ser Ser Gly Met Ser Glu His Thr Pro Leu Cys Ser Glu
1               5                   10

<210> SEQ ID NO 542
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 542

Ser Ser Pro Ser Phe Pro His Met Trp Ser Glu Asp Glu
1               5                   10

<210> SEQ ID NO 543
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 543

Val His Ser Glu Ser Trp His Ser Tyr Ser Ile His Ala
1               5                   10

<210> SEQ ID NO 544
<211> LENGTH: 13
<212> TYPE: PRT
<213> ORGANISM: Artificial Sequence
<220> FEATURE:
<223> OTHER INFORMATION: isolated from phage display libraries

```
<400> SEQUENCE: 544

Val Asn Asn Ala Met Gly His Met Gly Met Met Trp Cys
1               5                   10

<210> SEQ ID NO 545
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 545

Val Ser Cys Ser Ser Arg His Tyr Ser Ile Ser Trp Ser
1               5                   10

<210> SEQ ID NO 546
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 546

Trp Thr Trp Lys Arg Gln His His Arg Ser Ser Leu Tyr
1               5                   10

<210> SEQ ID NO 547
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 547

Tyr Ile Ser Phe Phe Glu His Gly Gln Ile Val Asp Ser
1               5                   10

<210> SEQ ID NO 548
<211> LENGTH: 19
<212> TYPE: PRT
<213> ORGANISM: Artificial Sequence
<220> FEATURE:
<223> OTHER INFORMATION: isolated from phage display libraries

<400> SEQUENCE: 548

Ser Cys Leu Val Phe Met Arg Pro Tyr Phe Leu Leu Val Phe Leu Met
1               5                   10                  15

Cys Trp Ser

<210> SEQ ID NO 549
<211> LENGTH: 19
<212> TYPE: PRT
<213> ORGANISM: Artificial Sequence
<220> FEATURE:
<223> OTHER INFORMATION: isolated from phage display libraries

<400> SEQUENCE: 549

Ser Cys Thr Phe Gly Phe Pro Cys Val Met Ser Leu Val Asn His Val
1               5                   10                  15

Pro Ser Ser

<210> SEQ ID NO 550
<211> LENGTH: 19
<212> TYPE: PRT
<213> ORGANISM: Artificial Sequence
<220> FEATURE:
```

<223> OTHER INFORMATION: isolated from phage display libraries

<400> SEQUENCE: 550

Ser Cys Leu Tyr Cys Leu Asn Tyr Ala Asn Phe Ser Asp Pro Met Thr
1               5                   10                  15

Met Phe Ser

<210> SEQ ID NO 551
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 551

Gly Phe Ala Trp Ser Ser Tyr Leu Gly Thr Thr Val His
1               5                   10

<210> SEQ ID NO 552
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 552

Leu Phe Gly Pro Ile Glu Tyr Thr Gln Phe Leu Ala Asn
1               5                   10

<210> SEQ ID NO 553
<211> LENGTH: 13
<212> TYPE: PRT
<213> ORGANISM: Artificial Sequence
<220> FEATURE:
<223> OTHER INFORMATION: isolated from phage display libraries

<400> SEQUENCE: 553

Phe Phe Ser Phe Phe Phe Pro Ala Ser Ala Trp Gly Ser
1               5                   10

<210> SEQ ID NO 554
<211> LENGTH: 20
<212> TYPE: PRT
<213> ORGANISM: Artificial Sequence
<220> FEATURE:
<223> OTHER INFORMATION: isolated from phage display libraries

<400> SEQUENCE: 554

Phe Phe Ser Phe Phe Phe Pro Ala Ser Ala Trp Gly Ser Ser Gly Ser
1               5                   10                  15

Ser Arg Gly Asp
            20

<210> SEQ ID NO 555
<211> LENGTH: 12
<212> TYPE: PRT
<213> ORGANISM: Artificial Sequence
<220> FEATURE:
<223> OTHER INFORMATION: isolated from phage display libraries

<400> SEQUENCE: 555

Leu Leu Ser Leu Leu Leu Pro Gly Ser Ser Gly Lys
1               5                   10

<210> SEQ ID NO 556
<211> LENGTH: 12

-continued

```
<212> TYPE: PRT
<213> ORGANISM: Artificial Sequence
<220> FEATURE:
<223> OTHER INFORMATION: isolated from phage display libraries

<400> SEQUENCE: 556

Ile Ile Ser Ile Ile Ile Pro Gly Ser Ser Gly Lys
1               5                   10

<210> SEQ ID NO 557
<211> LENGTH: 12
<212> TYPE: PRT
<213> ORGANISM: Artificial Sequence
<220> FEATURE:
<223> OTHER INFORMATION: isolated from phage display libraries

<400> SEQUENCE: 557

Phe Trp Ser Phe Trp Phe Pro Gly Ser Ser Gly Lys
1               5                   10

<210> SEQ ID NO 558
<211> LENGTH: 32
<212> TYPE: PRT
<213> ORGANISM: Artificial Sequence
<220> FEATURE:
<223> OTHER INFORMATION: isolated from phage display libraries

<400> SEQUENCE: 558

Ser Cys Ser Asp Cys Leu Lys Ser Val Asp Phe Ile Pro Ser Ser Leu
1               5                   10                  15

Ala Ser Ser Ser Ser Gly Arg Gly Asp Ser Pro Gly Arg Gly Asp Ser
            20                  25                  30
```